(12) United States Patent
Nagar

(10) Patent No.: US 10,973,996 B2
(45) Date of Patent: Apr. 13, 2021

(54) DEVICES, SYSTEMS AND METHODS FOR CONTROLLING CONDITIONS AND DELIVERY OF SUBSTANCES

(71) Applicant: Ron Nagar, Tel Aviv (IL)

(72) Inventor: Ron Nagar, Tel Aviv (IL)

( * ) Notice: Subject to any disclaimer, the term of this patent is extended or adjusted under 35 U.S.C. 154(b) by 271 days.

(21) Appl. No.: 15/327,000

(22) PCT Filed: Jul. 15, 2015

(86) PCT No.: PCT/US2015/040655
§ 371 (c)(1),
(2) Date: Jan. 17, 2017

(87) PCT Pub. No.: WO2016/011207
PCT Pub. Date: Jan. 21, 2016

(65) Prior Publication Data
US 2018/0207368 A1     Jul. 26, 2018

Related U.S. Application Data

(60) Provisional application No. 62/024,481, filed on Jul. 15, 2014, provisional application No. 62/044,258, (Continued)

(51) Int. Cl.
*A61M 5/44* (2006.01)
*A61J 1/16* (2006.01)
*F25B 21/04* (2006.01)

(52) U.S. Cl.
CPC .............. *A61M 5/445* (2013.01); *A61J 1/16* (2013.01); *A61J 1/165* (2013.01); *F25B 21/04* (2013.01);
(Continued)

(58) Field of Classification Search
CPC .................................................. A61M 5/445
See application file for complete search history.

(56) References Cited

U.S. PATENT DOCUMENTS

| 5,695,090 A | 12/1997 | Burdick |
| 6,454,746 B1 | 9/2002 | Bydlon et al. |

(Continued)

FOREIGN PATENT DOCUMENTS

| EP | 2361203 A1 | 8/2011 |
| WO | WO 2013/034458 A1 | 3/2013 |

(Continued)

OTHER PUBLICATIONS

International Search Report and Written Opinion, dated Oct. 7, 2015, for International Application No. PCT/US2015/040655.
(Continued)

*Primary Examiner* — Jenna Zhang
(74) *Attorney, Agent, or Firm* — Cooley LLP; Brian P. Hopkins

(57) ABSTRACT

Embodiments of the present disclosure are directed to devices, systems, and methods for controlling environmental conditions for a volume of material. In some embodiments, a handheld, portable environmental control sleeve (ECS) is disclosed which is configured for controlling at least one environmental condition of a drug contained within a drug delivery or storage device (DDSD). The ECS includes an environmental control mechanism (ECM), thermal insulation material, at least one of a power source, a processor, at least one electrical contact, at least one indicator, at least one switch, at least one environmental condition sensor, a wireless transceiver, a phase change material and at least one heat dissipater. Upon the ECS receiving at least a portion of the DDSD, the at least one environmental condition of a drug contained within the DDSD is controlled by the ECM to be within a predetermined range.

12 Claims, 30 Drawing Sheets

Related U.S. Application Data filed on Aug. 31, 2014, provisional application No. 62/053,823, filed on Sep. 23, 2014, provisional application No. 62/077,918, filed on Nov. 11, 2014, provisional application No. 62/080,366, filed on Nov. 16, 2014, provisional application No. 62/083,275, filed on Nov. 23, 2014, provisional application No. 62/086,689, filed on Dec. 2, 2014, provisional application No. 62/097,087, filed on Dec. 28, 2014, provisional application No. 62/127,008, filed on Mar. 2, 2015, provisional application No. 62/146,307, filed on Apr. 12, 2015, provisional application No. 62/150,567, filed on Apr. 21, 2015, provisional application No. 62/161,272, filed on May 14, 2015.

(52) U.S. Cl.
CPC ....... *A61M 5/44* (2013.01); *A61M 2205/3368* (2013.01); *A61M 2205/3584* (2013.01); *A61M 2205/3606* (2013.01); *A61M 2205/3633* (2013.01); *A61M 2205/3673* (2013.01); *A61M 2205/8206* (2013.01)

(56) References Cited

U.S. PATENT DOCUMENTS

| | | | |
|---|---|---|---|
| 7,861,538 B2 † | 1/2011 | Welle | |
| 8,398,602 B2 † | 3/2013 | Iio | |
| 8,646,282 B2 † | 2/2014 | Ilercil | |
| 8,663,167 B2 | 3/2014 | Bartha | |
| 8,887,512 B2 † | 11/2014 | Olsen | |
| 9,447,995 B2 † | 9/2016 | Bloedow | |
| 9,791,184 B2 † | 10/2017 | Novisoff | |
| 10,254,499 B1 * | 4/2019 | Cohen | G02B 6/4463 |
| 2006/0271014 A1 * | 11/2006 | Hynes | A61M 5/445 604/507 |
| 2008/0022696 A1 | 1/2008 | Welle et al. | |
| 2009/0049845 A1 | 2/2009 | McStravick et al. | |
| 2011/0155621 A1 | 6/2011 | Lindquist et al. | |
| 2011/0218502 A1 * | 9/2011 | Iio | H02J 7/0042 604/264 |
| 2012/0312031 A1 * | 12/2012 | Olsen | A47J 41/0044 62/3.62 |
| 2014/0090737 A1 | 4/2014 | Reid | |
| 2014/0165607 A1 † | 6/2014 | Alexander | |
| 2014/0216485 A1 * | 8/2014 | Egoyants | A24F 47/008 131/329 |
| 2015/0151893 A1 * | 6/2015 | Wengreen | F25D 3/00 206/571 |
| 2015/0229267 A1 * | 8/2015 | Hilliard | H02S 40/44 136/248 |

FOREIGN PATENT DOCUMENTS

| | | |
|---|---|---|
| WO | WO 2014/064691 A2 | 5/2014 |
| WO | WO-2015/055836 A1 | 4/2015 |

OTHER PUBLICATIONS

Screenshots from Website: www.insulinsafe.com.cn/en/category/product; Sep. 13, 2014; Beijing Insulinsafe Healthcare Limited.
Screenshots from Website: www.insulinsafe.com.cn/en/; May 10, 2013; Beijing Insulinsafe Healthcare Limited.
Extended European Search Report dated Jul. 2, 2019 for EP Application No. 16868134.4, 7 pages.

\* cited by examiner
† cited by third party

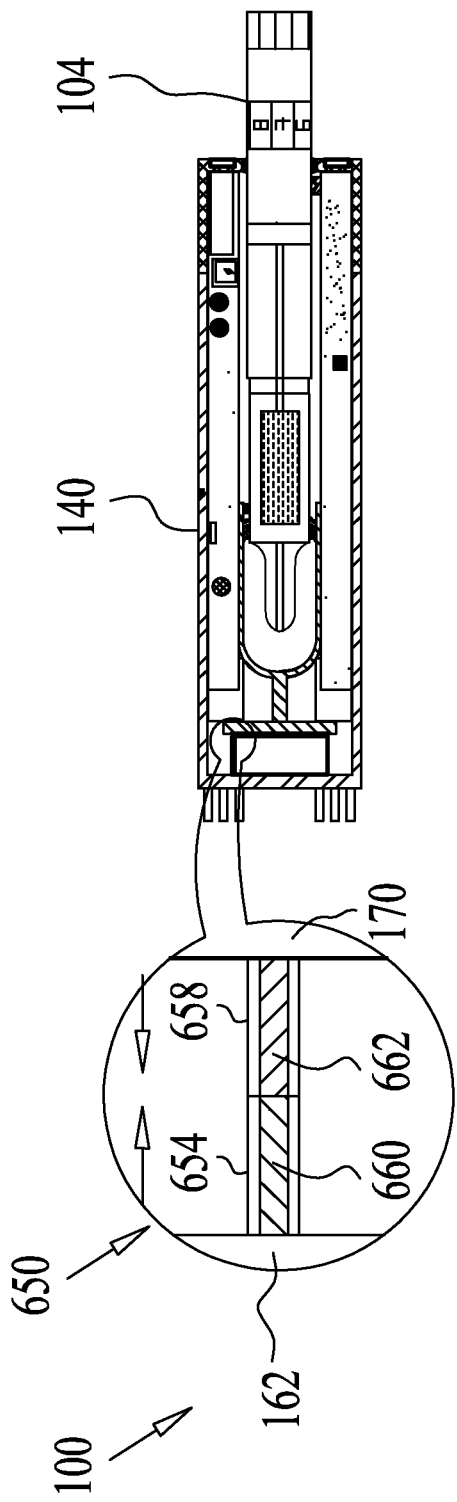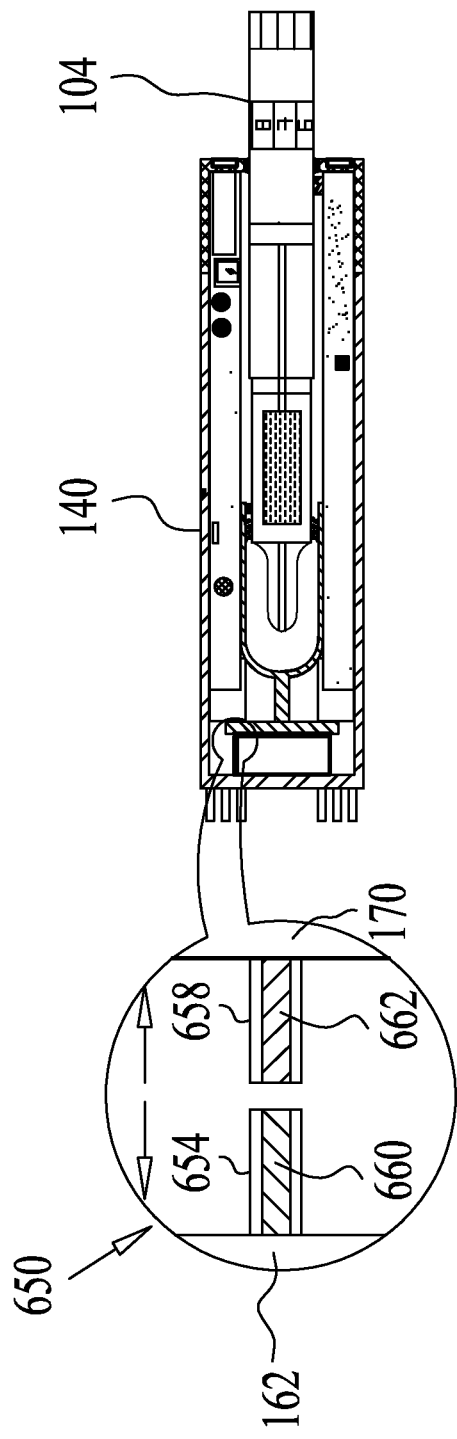
FIGURE 18A
FIGURE 18B

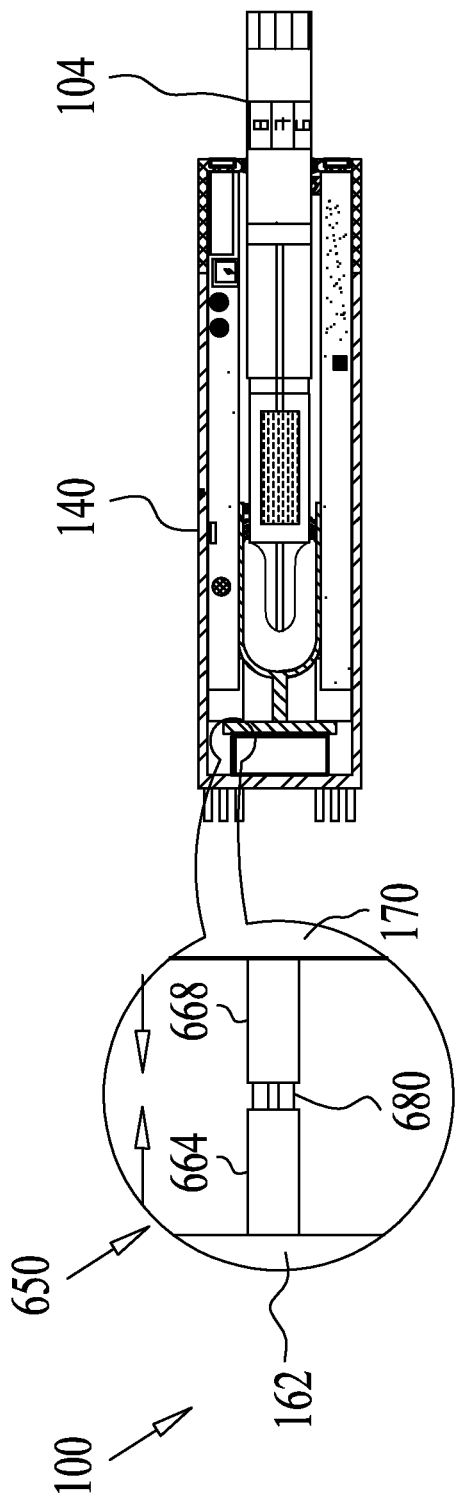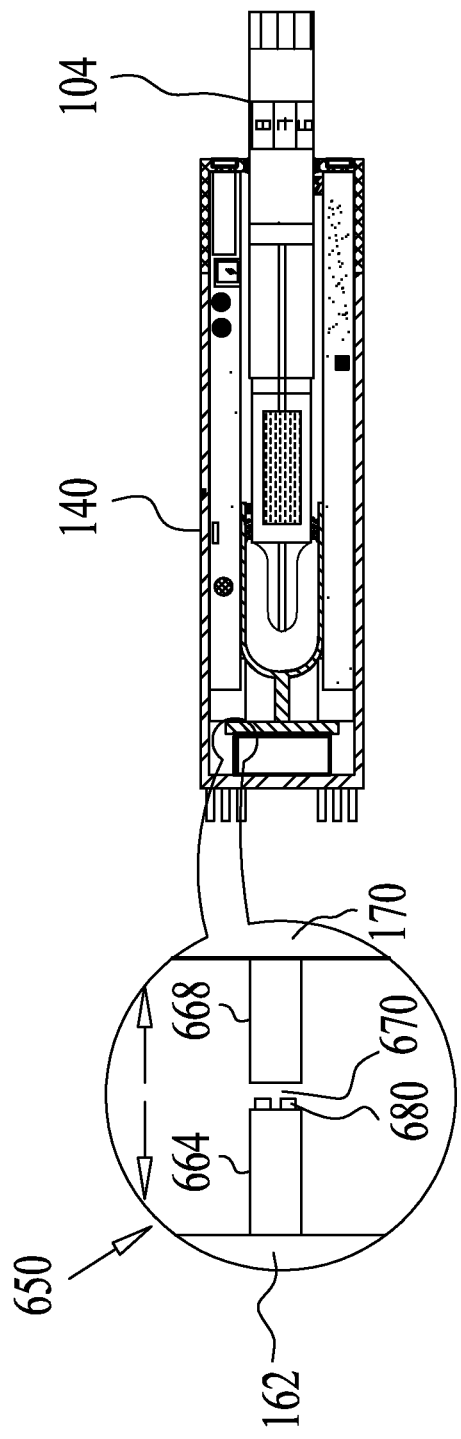
FIGURE 19A
FIGURE 19B

DEVICES, SYSTEMS AND METHODS FOR CONTROLLING CONDITIONS AND DELIVERY OF SUBSTANCES

CROSS REFERENCE TO RELATED APPLICATIONS

This application claims benefit of and priority to International Patent Application No. PCT/US2015/040655, filed Jul. 15, 2015, which in turn claims benefit of and priority to U.S. Provisional Patent Application Nos. 62/024,481 filed Jul. 15, 2014; 62/044,258 filed Aug. 31, 2014; 62/053,823 filed Sep. 23, 2014; 62/077,918 filed Nov. 11, 2014; 62/080,366 filed Nov. 16, 2014; 62/083,275 filed Nov. 23, 2014; 62/086,689 filed Dec. 2, 2014; 62/097,087 filed Dec. 28, 2014; 62/127,008 filed Mar. 2, 2015; 62/146,307 filed Apr. 12, 2015; 62/150,567 filed Apr. 21, 2015; and 62/161,272 filed May 14, 2015. The present application incorporates herein by reference the disclosures of each of the above-referenced applications in their entireties.

TECHNICAL FIELD

Some embodiments of the present disclosure generally relate to the controlling of substance environmental conditions and substance delivery.

BACKGROUND

Drugs can be sensitive to environmental conditions such as light, humidity, temperature, pressure, atmosphere and other conditions. Many drugs have limited boundaries to such conditions that if exceeded, can degrade the drug activity. Drugs that are exposed to environmental conditions, which exceed certain limits, might lose their potency. Drugs that are exposed to extreme environmental conditions might even turn to be harmful, if used. For example, life maintaining drugs (e.g., insulin) can be exposed to extreme environmental conditions if left within a vehicle, where temperatures can rise as high as 130 degree F. on a summer day. Similarly, upon a disaster situation (e.g., power outage, storm, and the like), drug delivery devices and pharmaceuticals may be exposed to harsh environmental conditions. In addition, drug delivery devices and pharmaceuticals used for emergency events (e.g. earthquakes, hurricanes, wars) may require storage for extended periods of time, sometimes for over a year, without maintenance.

While devices exist that can maintain drugs and drug-containing delivery devices under controlled environmental conditions, such current devices are quite large and typically require a regular AC power supply for their operation, or large batteries of limited duration.

For example there are today mini-refrigerators used to keep drugs in a cooled environment such as the Dison BC-170A mini insulin fridge from Zhengzhou Dison Electric Co. (http://www.medincn.com/sell_offers/104901/diabetic-portable-refrigerator-medicine-refrigerator-insulin-cooler.html). There are also other packs containing ice or devices which can cool the drug based on water evaporation such as the FRIO® cooling wallet.

However these cooling packs do not control or stabilize the temperature, rather provide cooling to the entire pen injection device or drug vial or drug cartridge.

Injection devices similar to existing insulin pen injection devices for single use (such as the prefilled NovoLog FlexPen http://www.novolog.com/insulindiabetes/novolog-flexpen.aspx), or reusable devices (such as the NovoPen http://www.novonordisk.com/diabetes_care/insulin_pens_and_needles/novopen_4/default.asp), have means to set the desired amount of drug to be injected. Such devices do not have means to control the environmental conditions of the drug within the pen. When a drug is inside the pen, the drug must be kept in a refrigerator or in devices (e.g., Dison BC-170A mini insulin refrigerator) for maintaining the drug under stable temperature conditions.

SUMMARY OF SOME OF THE EMBODIMENTS

In some embodiments of the present disclosure, the environmental conditions of any substance may be controlled and/or maintained. The substance may comprise in a non-limiting example, a drug, a protein based substance, such as a protein based drug, a biological substance, such as hormones, a growth hormone, blood, body fluids, sperms, or eggs. The substance may comprise cosmetics, such as lipsticks, perfumes, toiletries, hair or skin care products, sprays, mousses, emulsions and gels, for example. The substance may comprise, resins, adhesives, glues, epoxy or cyanoacrylate glue. The substance may be configured in any suitable form, such as a solid, liquid, emulsion, gas, gel, granule, and powder, for example. Wherein the substance comprises a drug, the drug may comprise any suitable form such as a solid, powder, tablet, pill, capsule, gas, gel, cream, emulsion, spray or a suppository, and may be delivered in any suitable manner.

The substance may include more than one substance at the same or different phase, such as, for example, a liquid mixed with another liquid or a liquid mixed with a powder. In some embodiments, keeping one component of the mixture at a particular environmental condition requires a smaller amount of power than both components (e.g., keeping a small amount of powder at a specific temperature).

In some embodiments, an environmental control apparatus is provided and includes means to control the environmental conditions of a substance, such as a drug, contained in a container. Such apparatuses enable the control of the environmental conditions of a small volume of a substance, such as a drug with a volume, in a non-limiting example, of a few microliters and up to 10 milliliters, while requiring far less energy than having to maintain environmental control over a substance container. This enables the maintenance of a substance in a substance container for a substantially long time with little power requirements. For example, in some embodiments, environmental conditions required to properly store the substance may be maintained as long as hours, days, weeks, months or even more than a year.

With many substances the long term storage environmental conditions (e.g., temperature) and short-term use environmental conditions, may differ. With respect to the latter, in some embodiments, the container may be configured for switching between conditions. In use conditions, the conditions may be maintained for a shorter period of time than the long term storage conditions.

In some embodiments, the environmental control apparatus may be configured to be relatively small, handheld and/or portable.

In some embodiments of the present disclosure there is provided a handheld, portable environmental control sleeve (ECS) configured for controlling at least one environmental condition of a drug contained within a drug delivery or storage device (DDSD), the ECS includes an environmental control mechanism (ECM), thermal insulation material, and any two or more of: a power source, a controller, at least one electrical contact, at least one indicator, at least one switch, at least one environmental condition sensor, a wireless transceiver, a phase change material and at least one heat dissipater. When the ECS receives at least a portion of the DDSD, at least one environmental condition of a drug contained within the DDSD is controlled by the ECM to be within a predetermined range.

In some embodiments, the ECS is selected from the group consisting of: a cylinder, a tube, a cap, and an oblong enclosure. The ECS may encapsulate the DDSD or partially enclose a portion of the DDSD.

In some embodiments, the ECS shape is a cap and the interior of the cap is configured to enclose at least a substantial portion of a drug reservoir of the DDSD. The cap may be reusable or disposable.

In some embodiments, the ECS is a tube configured to open and close such that the DDSD is contained therein.

In some embodiments, the ECS is configured for controlling at least two predetermined ranges of the environmental condition. The ECS may be configured to switch from controlling a first predetermined range to the second predetermined range. The ECS may be configured to control at least one environmental condition of a volume of less than or equal to about 10 ml. The environmental condition may be automatically or manually controlled.

In some embodiments, The ECS may further comprise at least one temperature sensor configured to sense a temperature inside the ECS and/or at least one temperature sensor configured to sense a temperature external to the ECS.

In some embodiments, the readings of a temperature sensor configured to sense a temperature inside the ECS and a temperature sensor configured to sense a temperature external to the ECS, is used to determine the amount of drug in the DDSD or the amount of drug removed from the DDSD.

In some embodiments, the ECM may comprise a thermoelectric element (TEC) or a refrigerant-based heat pump or a heating and/or cooling element.

In some embodiments, the environmental condition is temperature and the ECS may further include the power source and a temperature sensor configured to sense the temperature of the interior of the ECS. The flow of power from the power source to the ECM may be determined based upon a temperature of the interior of the ECS sensed by the temperature sensor. The temperature sensor may comprise a thermistor.

In some embodiments, the ECM may be configured to control the environmental condition of the drug contained in the DDSD upon the environmental condition being at least one of above and below a predetermined range. The environmental condition may comprise temperature, and the ECM may be configured to perform at least one of: cooling the drug when the temperature inside the ECS is above the predetermined range to a temperature within the predetermined range, and heating the drug when the temperature inside the ECS is below the predetermined range, to a temperature within the predetermined range.

In some embodiments, the ECS may be configured to control the at least one environmental condition according to at least one of: a first storage state configured to retain the drug contained in the DDSD at the environmental condition within a first range, and a use state configured to retain the drug contained in the DDSD at the environmental condition within a second range. Prior to first use of the DDSD, the environmental condition of the drug may be maintained at the storage state. After first use of the DDSD, the environmental condition of the drug may be maintained at the use state. The ECS may include a first switch. The use state may be activated via the switch or automatically upon first use of the DDSD.

In some embodiments, the ECS may include at least one of a port and the wireless transceiver for communicating with at least a first device. The ECS may be configured to communicate with a remote device. The ECS may comprise a phase-change material configured to aid in control of the environmental condition of a drug contained in the DDSD.

In some embodiments, the environmental condition is temperature and wherein the ECS may comprise a processor for controlling the ECM. The processor may include computer instructions including an algorithm operating thereon and configured to control the ECM. The algorithm may be configured to automatically control the temperature of a drug stored within the DDSD and/or within the chamber within a predetermined range. The algorithm may control the temperature while minimizing a thermal load created by the operation of the ECM.

In some embodiments, the thermal insulation comprises INSULON® or similar constructed material. The phase-change material may be arranged within the INSULON® material or external to the INSULON® material.

In some embodiments, the ECM is configured with a first side in thermal contact with the interior of the ECS and a second side in thermal contact with the heat dissipater. The ECM may be placed within any one of the following: an aperture formed within the thermal insulation material; or a thermal conducting area formed within the thermal insulation material, the thermal insulation material may be formed of walls and an evacuated gap between the walls, wherein walls of the thermal insulation material are adjoined at an area of the thermal insulation material to form the thermal conducting area.

The ECS may be configured to mechanically fit the DDSD.

In some embodiments of the present disclosure there is provided a handheld, portable environmental control sleeve (ECS) configured for housing at least a substantial portion of a drug delivery or storage device (DDSD), the ECS may comprise a thermal insulation material and may be configured to control at least one environmental condition of a drug stored in the DDSD.

In some embodiments of the present disclosure there is provided a pen injection system for delivering a drug into tissue of a user. The system may comprise a drug injection pen having a drug reservoir containing a drug. The ECS may be configured as a cap for receiving at least a substantial portion of the drug reservoir and controlling the environmental condition thereof. The ECS may further include at least one of a port and a wireless transceiver for communicating with at least a first device.

In some embodiments, the ECS includes the wireless transceiver and is configured to communicate with a remote device. The ECS may comprise a phase-change material configured to aid in control of the environmental condition of a drug contained in the DDSD.

In some embodiments, at least a portion of the DDSD comprises the drug reservoir configured to be in thermal contact with the ECM. The ECM may be housed in the DDSD and is activated by a controller in the cap. In some embodiments, the ECM is housed in the cap.

In some embodiments the ECM may be embedded within the injection pen or within the cap. In some embodiments, an activation element may be provided and configured to activate the ECM which is part of the cap. The activation element may be housed in the injection pen or housed in the cap.

In some embodiments of the present disclosure there is provided a handheld, portable drug delivery device comprising an enclosure, a drug chamber for storing a drug, the chamber being arranged in proximity to the enclosure and configured to be thermally shielded from the enclosure, an environmental control mechanism (ECM) configured to control at least one environmental condition of the drug and optionally monitor the environmental condition and a dispensing assembly. The dispensing assembly may be configured to deliver the drug, retained in the chamber, into a patient.

The dispensing assembly may comprise a needle and/or cannula configured to be in fluid communication with the drug within the chamber and deliver the drug into the patient. The dispensing assembly may comprise an opening configured for allowing removal of the drug from the chamber and delivering thereof to the patient via an orifice provided with the patient. The chamber may be configured to retain a volume of less than or equal to about 10 milliliters.

The device may comprise at least one of: a power source, a cannula or needle for delivering the drug into the tissue, an optional transparent section in the enclosure between the chamber and the needle, a setting mechanism for setting the drug amount for delivery to the tissue, and the dispensing assembly for dispensing the drug from the chamber into the tissue via the needle or cannula. The needle or cannula may be configured as an integral part of the delivery device.

In some embodiments, the chamber may be configured for insertion into the delivery device prior to use. In some embodiments, the chamber may be pre-loaded with the drug prior to use. The chamber may be configured to reside within the enclosure, or may be configured for insertion into the enclosure before use.

In some embodiments, the device may comprise a second chamber and a mixing element. The second chamber may be thermally isolated from the enclosure or may be not thermally isolated from the enclosure. The second chamber may contain a liquid portion of the drug.

In some embodiments, at least one environmental condition is automatically controlled.

At least one temperature sensor may be configured to sense a temperature of at least one of the inside of the chamber and the inside of the enclosure.

In some embodiments, the ECM comprises a thermoelectric cooler (TEC) or a refrigerant-based heat pump. In some embodiments, the environmental condition is a temperature of the drug. The device may further comprises a power source for powering the ECM and a temperature sensor configured to sense the temperature of at least one of the chamber and the enclosure. The flow of power from the power source to the ECM is determined based upon a temperature of at least one of the chamber and the enclosure sensed by the temperature sensor. The ECM may be configured to control the environmental condition of the drug upon the environmental condition being at least one of above and below a predetermined range. For example, the environmental condition may comprise temperature, and the ECM may cool the drug when the temperature is above the range to a temperature within the range, and the ECM may heat the drug when the temperature is below the range to a temperature within the range.

In some embodiments, control of at least one environmental condition is according to at least one of: a first storage state configured to retain the drug at the environmental condition within a first range, and a use state configured to retain the drug at the environmental condition within a second range.

In some embodiments, prior to first use of the device, the environmental condition of the drug is maintained at the storage state. After first use of the device, the environmental condition of the drug may be maintained at the use state. The use state may be activated via a switch or automatically upon first use of the device.

In some embodiments, the device may comprise a drug-delivery pen. The device may comprise insulation and may further comprise a phase-change material configured to aid in control of the at least one environmental condition of a drug stored in the chamber. The insulation may comprise a phase-change material configured to aid in control of the environmental condition of a drug stored in the chamber. The phase change material may be configured to aid in the heating or cooling of a drug contained within the chamber and/or DDSD.

In some embodiments, at least one of the chamber and the enclosure comprise INSULON® or similarly constructed material.

In some embodiments of the present invention there is provided a method for maintaining the efficacy of a drug over a period of time in a portable drug delivery device, the method comprising: providing a device such as the ECS or the drug delivery device; and controlling the at least one environmental condition via the ECM so as to maintain the drug at the at least one environmental condition.

In some embodiments, at least one environmental condition is temperature, and controlling of the temperature comprises either cooling or heating at least one of the drug and the area enclosing the drug. Controlling the environmental condition may be automatic or may be manual.

The method may further comprise sensing a temperature of at least one of the drug and an area enclosing the drug via at least one temperature sensor. The device may further comprise providing power from a power source to the ECM based upon a temperature of at least one of the drug and the area enclosing the drug.

The method may further comprise controlling at least one environmental condition of the drug upon the environmental condition being above or below a predetermined range. Controlling the temperature may comprise cooling the drug via the ECM when the temperature is above the range to a temperature within the range and/or heating the drug via the ECM when the temperature is below the range to a temperature within the range.

Control of the environmental condition may be according to at least one of: a first storage state configured to retain the drug at the environmental condition within a first range, and a use state configured to retain the drug at the environmental condition within a second range. Prior to first use of the device, control of at least one environmental condition may comprise maintaining at least one environmental condition of the drug at a storage state. After first use of the device, control of the environmental condition comprises maintaining the environmental condition of the drug at a use state.

In some embodiments, the method may further comprise generating energy from the temperature gradient between at least one of the chamber, the enclosure and an outside environment external to the device. The energy may be generated via a thermoelectric element. The generated energy may be stored in a battery for supplying power to the ECM.

In some embodiments, the method may further comprise communicating information from the provided device to another device via at least one of a port and a wireless transceiver. The device may comprise a remote device.

In some embodiments there is provided a handheld, portable environmental control apparatus configured for controlling at least one environmental condition of a substance contained within a substance container comprising a substance chamber for containing the substance therein, the apparatus including an environmental control element comprising any one of: thermal insulation material, or an active control element and thermal insulation material. When the apparatus is engaged with the container at least one environmental condition of the substance contained within the chamber is controlled by the environmental control element to be within a predetermined range. In some embodiments the environmental control element may be configured to perform both of: shifting the environmental condition of the substance, when the environmental condition inside the chamber is above the predetermined range, to an environmental condition within the predetermined range, and shifting the environmental condition of the substance, when the environmental condition inside the chamber is below the predetermined range, to the environmental condition within the predetermined range.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein and are considered only some of the numerous embodiments disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

The principles and operations of the systems, apparatuses and methods according to some embodiments of the present disclosure may be better understood with reference to the drawings, and the following description. The drawings are given for illustrative purposes only and are not meant to be limiting.

FIGS. 18A and 18B are a schematic illustration of an exemplary thermal switch operative with a substance control system, shown in an active mode (FIG. 18A) and an inactive mode (FIG. 18B), according to some embodiments of the present disclosure;

FIGS. 19A and 19B are a schematic illustration of an exemplary thermal switch operative with a substance control system, shown in an active mode (FIG. 19A) and an inactive mode (FIG. 19B), according to some embodiments of the present disclosure;

DETAILED DESCRIPTION

FIGS. 1A-6 illustrate an exemplary substance control system 100 according to some embodiments of the present disclosure. The substance control system 100 may include a substance container 104, for containing a substance within a substance chamber 106.

The substance may comprise in a non-limiting example, a drug, such as insulin, a protein based substance, such as a protein based drug, a biological substance, such as hormones, a growth hormone, blood, body fluids, sperms, or eggs. The substance may comprise cosmetics, such as lipsticks, perfumes, toiletries, hair or skin care products, sprays, mousses, emulsions or gels, for example. The substance may comprise, resins, adhesives, glues, epoxy or cyanoacrylate glue. The substance may be configured in any suitable form, such as a solid, liquid, emulsion, gas, gel, granules, or powder, for example. The substance may include more than one substance at the same or different phase, such as, for example, a liquid mixed with another liquid or a liquid mixed with a powder. Wherein the substance comprises a drug, the drug may include any suitable forms such as a solid, powder, tablet, pill, capsule, gas, gel, cream, emulsion, spray or a suppository and may be delivered in any suitable manner.

Figure 1A:
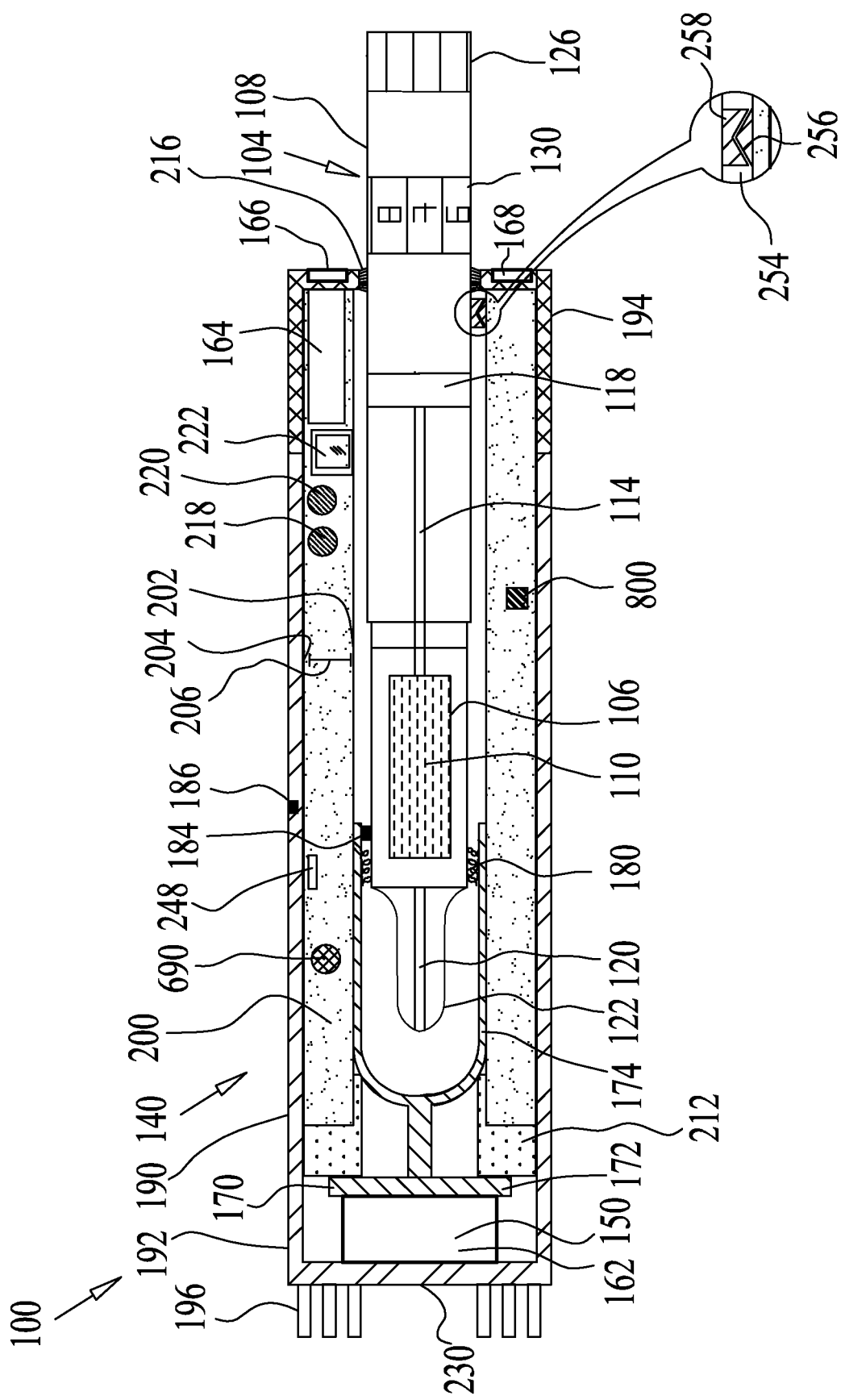
FIGS. 1A and 1B are a schematic illustration of an exemplary substance control system, at an assembled state (1A) and disassembled state (1B) according to some embodiments of the present disclosure.
Figure 1B:
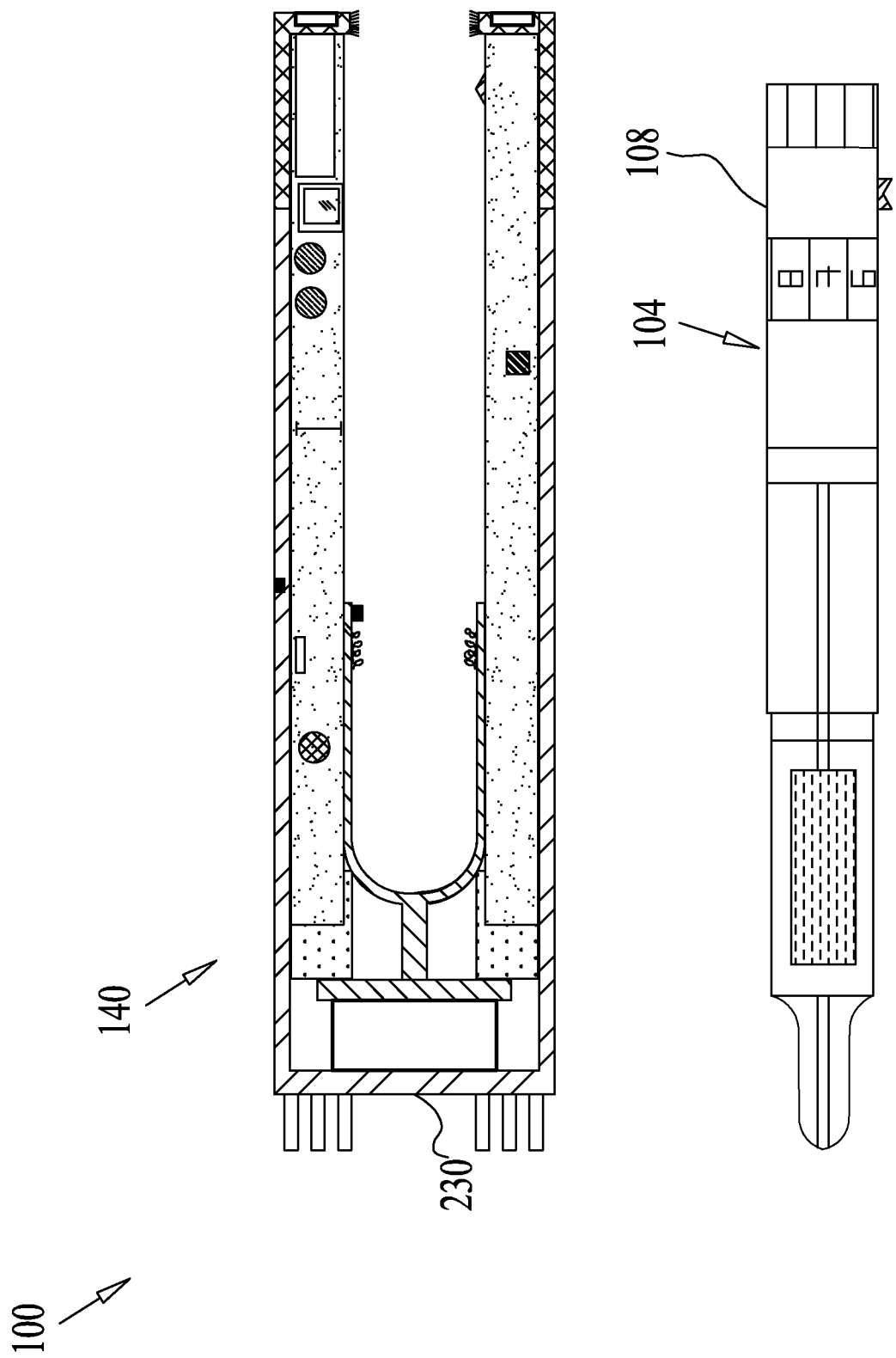

In some embodiments, the container 104 may comprise a drug delivery device or a drug storage device (DDSD), such as an injection pen 108 shown in FIGS. 1A and 1B. In some embodiments, the injection pen 108 may be a reusable injection pen configured for housing a replaceable drug cartridge comprising a drug 110, which is retained within the substance chamber 106. In some embodiments, the injection pen 108 may be a prefilled (or pre-loaded), disposable injection pen.

In a non-limiting example, the substance chamber 106 of the injection pen 108 or any other container 104 may comprise a drug reservoir and encompass a volume of few microliters and up to 10 milliliters. In some embodiments the volume is up to about 1 milliliter. In some embodiments, the volume is about 10 milliliters or more than 10 milliliters. In some embodiments, the volume is less than 1 milliliter.

The container 104 may be configured in any suitable configuration for containing a substance therein. Some further exemplary containers and DDSDs for containing drugs may include a syringe, a drug vial (e.g. the vial shown in FIGS. 9-12), a drug cartridge (e.g. drug cartridge shown in FIGS. 13-15), an ampule (e.g. ampule shown in FIGS. 16-17), a pump (e.g. pump shown in FIG. 23), a pill box (e.g. pill box shown in FIG. 24), and an inhalator, (e.g. inhalator shown in FIG. 25).

The injection pen 108 may include a drug dispensing assembly 114 configured to deliver the drug 110 retained in the chamber 106 into a user (e.g. a human or animal patient). The drug dispensing assembly 114 may comprise a plunger of a piston 118 or any suitable means to advance the drug 110 to be delivered via a needle 120, which may be protected by a needle cover 122.

The piston movement may be adjusted in any suitable manner, such as by a unit injection setting knob 126. In another embodiment, piston movement may be adjusted by manually applying pressure on the top of the piston 118, such as in syringes, or pressure may be applied on the knob 126, such as in a jet injector.

In some embodiments, setting the desired drug dose in the injection pen 108 may be performed by knob 126. Examples of such pens can be found in U.S. Pat. Nos. 6,454,746 and 8,663,167, each disclosure of which is incorporated herein by reference in its entirety. In some embodiments, the setting may be provided by a switch or any other electronic format allowing a user to set a desired number, wherein the desired number corresponds to the amount of drug units to be injected.

The selected drug dose may be displayed by numerical display 130.

At least part of the injection pen 108 around the chamber 106 may be transparent to allow visual inspection of the drug solution in the chamber 106.

The substance, such as drug 110, may be required to be stored and/or delivered at selected environmental conditions or at a range thereof. A non-limiting example of the environmental conditions may include temperature, light, humidity, and/or pressure.

The substance control system 100 may comprise an environmental control apparatus 140 comprising an environmental control element 150 for controlling at least one environmental condition of the substance, including at least one of a temperature, light, humidity, and pressure. The environmental control element 150 may be configured to maintain or change one or more such conditions of the substance to reach a predetermined selected condition. The environmental control element 150 may additionally be configured to monitor the environmental condition.

The environmental control element 150 may comprise any suitable functionality for controlling and affecting one or more environmental conditions of the substance, such as drug 110. For example, wherein the condition is temperature, the environmental control element 150 may include temperature controlling elements for maintaining a desired temperature, and/or for heating and cooling. The environmental control element 150 may include passive control elements and/or active control elements. Non-limiting examples of active temperature controlling elements may include an environmental control mechanism (ECM) 162. The ECM 162 may comprise a micro-heat-pump/refrigerator configuration, such as a magnetic configuration utilizing the Joule-Thomson expansion functionality or a mechanical configuration using a cooling gas, such as Freon, for example. Further active elements may include a thermoelectric cooling/heating element, a thermoelectric cooling element (TEC) or a thermoelectric heat pump used for cooling and/or heating by utilizing the Peltier effect, such as by controlling the flow of current/voltage to chamber 106.

Additional methods for removing/adding heat from/to the chamber 106 may be used, including, for example, micro-fans and/or heat sink elements.

The active temperature controlling elements may be in communication with a power source, such as a battery 164, a controller and electronics 166, such as a thermistor, a transistor, boards, wires or circuitry, e.g. a control circuit for controlling the temperature controlling elements. Electrical connections (not shown) between the battery 164, and the controller and electronics 166 and the ECM 162 and any other electrical component, may be provided.

In some embodiments, the environmental condition may be automatically controlled via controller 166 or the environmental condition may be manually controlled by the user.

In some embodiments, the battery 164 may be rechargeable. Recharging may be performed via a recharging port 168, or via inductance or other means which allow electrical charge generation.

In some embodiments, the ECM 162 (e.g. a TEC) may be in thermal communication with the chamber 106 or in proximity thereto, via a thermal transmitter 170, formed in any suitable configuration. As seen in FIG. 1A, the ECM 162 is in thermal and/or mechanical contact with a base portion 172 of the thermal transmitter 170. The thermal transmitter 170 may comprise a protruding portion 174 protruding from the base portion 172. The protruding portion 174 may be engaged with the chamber 106 and may be shaped as an elliptic paraboloid or any other suitable shape. The thermal transmitter 170 may be formed of any suitable thermally conducting material, such as aluminum, for example.

To further enhance thermal and/or mechanical contact between the thermal transmitter 170 and the chamber 106, there may be provided thermal conductors 180 therebetween along at least a portion of the chamber 106 or the container 104. The thermal conductor 180 may be formed of any suitable material, such as a flexible thermally conducting material, e.g. a sponge thermal conductor, configured, when pressed by the thermal transmitter 170, to facilitated thermal communication with the chamber 106.

The environmental control apparatus 140 and/or the container 104 may include at least one or more temperature sensitive elements comprising substance temperature sensors 184, designed to monitor the temperature of the chamber 106. In some embodiments, the chamber 106 may be made of a material that is thermally conducting, such that the temperature of the chamber 106 is substantially similar to the temperature of the substance inside the chamber 106.

In some embodiments, the temperature sensor 184 may be configured to sense the temperature of the interior of the environmental control apparatus 140 (e.g. the environmental control sleeve (ECS)) such that the temperature of the drug 110 contained in the container 104 comprising the DDSD can be determined based on the temperature of the interior of the ECS.

An additional ambient temperature sensor 186 or a plurality of sensors 186 may be provided to monitor the ambient temperature outside the environmental control apparatus 140. In some embodiments, the ambient temperature sensor 186 may be placed away from the environmental control apparatus 140 and the container 104. The ambient temperature sensor 186 may be configured to communicate with a tracking device or communication device 250 and/or a central database 252, as will be further described in reference to FIG. 2.

In a non-limiting example, the substance temperature sensor 184 and/or ambient temperature sensor 186 may comprise a thermistor.

In an exemplary, non-limiting embodiment, a thermogenerator chip may be positioned at one side thereof adjacent to chamber 106 for operating as the substance temperature sensor 184, while the opposite side can be used to detect the temperature external to the container 104, thereby operating as the ambient temperature sensor 186.

The ECM 162, such as the TEC, may generate heat during its operation. A heat dissipater 190 may be provided and may be formed in any suitable configuration. In some embodiments, the heat dissipater 190 may comprise a heat sink or an active heat dissipater, such as a micro-fan.

In some embodiments, a cover 192 of the environmental control apparatus 140 may at least partially or fully comprise the heat dissipater 190. As seen in FIG. 1A, the cover 192 is formed partially of the heat dissipater 190 and partially of a plastic portion 194. The heat dissipater portion 190 may terminate at any suitable location along the cover 192, such as at a location overlying the ECM 162, or a location overlying thermal transmitter 170, a location overlying the chamber 106 or any other section of the container 104. The remaining cover may be formed of the plastic portion 194 or any other suitable materiel.

The heat dissipater 190 may be formed of any suitable material, such as aluminum for dissipating heat from the ECM 162 to the ambient environment. The cover 192 may be formed with a smooth surface. The cover 192 may additionally or alternatively be configured with formations thereon, such as knurls, notches, fins or corrugations for example, so as to performing as miniature heat sinks thereon.

In some embodiments, the cover 192 may comprise recesses for allowing heat to dissipate to the ambient environment therethrough. In some embodiments, heat dissipating fins 196 or any other heat dissipating element may be provided on cover 192 or any other suitable location on the environmental control apparatus 140.

It is appreciated that any embodiment of the environmental control apparatus 140 of FIGS. 1A-25 may comprise the heat dissipating fins 196 or any other heat dissipating elements.

The cover 192 may be formed of an opaque material for preventing penetration of light therein.

A non-limiting example of a passive temperature controlling element includes thermal insulation 200, also referred to as thermal isolation, formed of any suitable insulating material. The thermal insulation 200 may be placed intermediate the cover 192 and the chamber 106 for preventing uncontrolled changes in the substance temperature.

In some embodiments, thermal insulation 200 may be realized by a multi-layered material, formed of walls 202 and 204. A gap 206 defined by a space between the walls 202 and 204 may be, at least partially, evacuated. In a non-limiting example, such a thermal insulation configuration including the multi-layered material formed of walls 202 and 204 and evacuated gap 206, may be commercially available as INSULON®, made by Concept Group, Inc. (www.conceptgroupinc.com), as well as similar constructions disclosed in U.S. Publication No. 20140090737, incorporated herein by reference in its entirety. The walls 202 and 204 may be formed of stainless steel, such as stainless steel 340. Walls 202 and 204 may be vacuum brazed at both edges with the gap 206 in between the layers. In some embodiments, this gap 206 may be formed with a width of about 0.6 mm, however the gap 206 may be smaller or larger. In some embodiments, the gap width may range from about 0.3-5 mm. In some embodiments, the gap width may range from about 0.6-3 mm.

In some embodiments, the vacuum within the gap 206 may be relatively high, such as about $10^{-9}$ torr, in a non-limiting example.

Further insulating materials, such as a thermal insulating foam 212 may be provided intermediate the cover 192 and the chamber 106.

Air tight encapsulation of the container 104 within the environmental control apparatus 140 may be provided for preventing exposure to humidity. In some embodiments, a brush 216 or any other flexible material may be placed at least partially intermediate the environmental control apparatus 140 and the container 104. The brush 216 may prevent formation of air pockets during insertion and removal of the container 104 into and from the environmental control apparatus 140.

In some embodiments, a thin layer of a phase change material may be provided around the container 104. The phase change material may be configured to change from a liquid phase to a solid phase for creating an air gap that allows removal of the container 104 from the environmental control apparatus 140. After insertion of the container 104 back into the environmental control apparatus 140, the phase is changed to a liquid phase for removal of the air gap.

Figure 2:
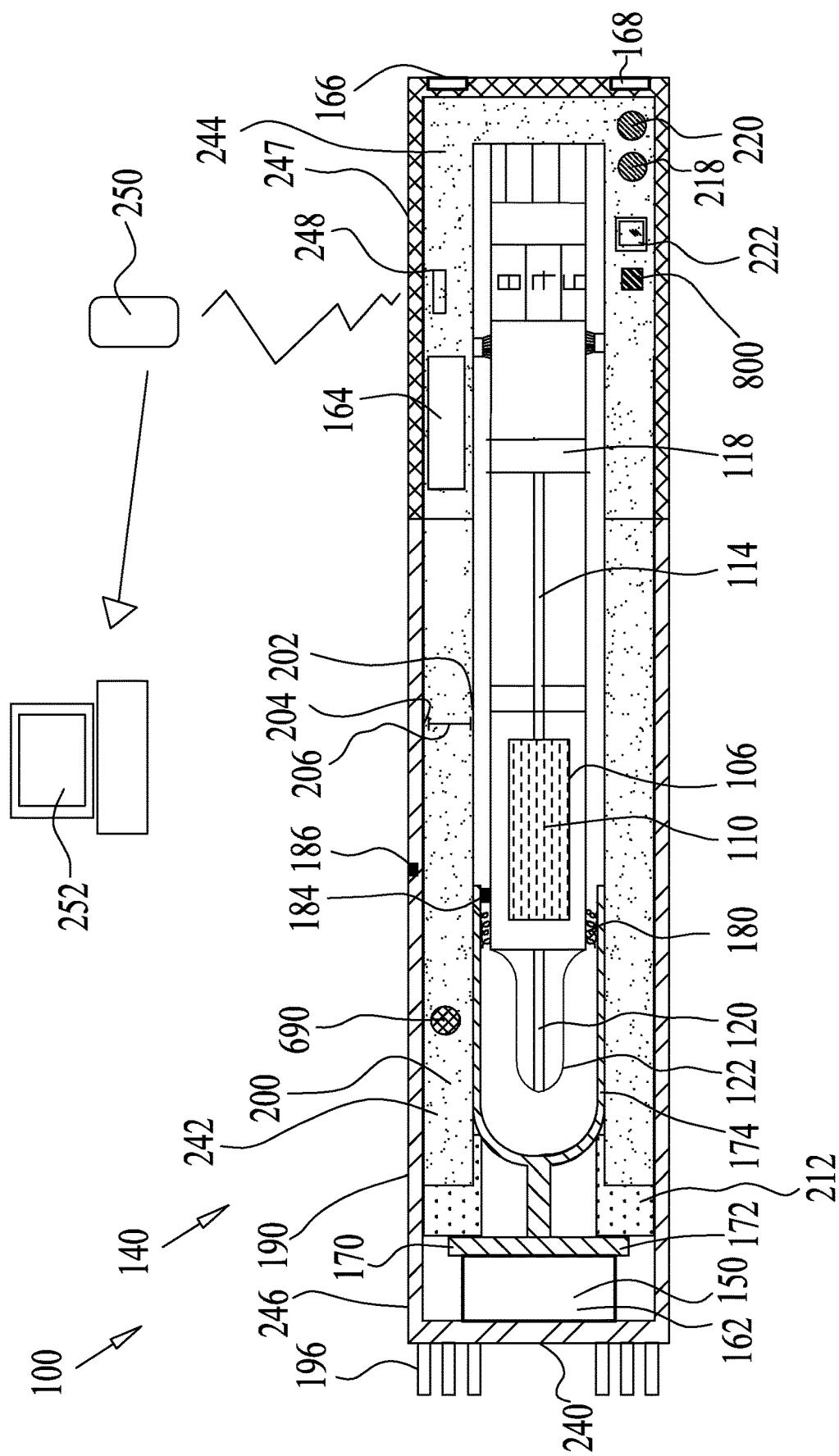
FIG. 2 is a schematic illustration of an exemplary substance control system according to some embodiments of the present disclosure.

In some embodiments, the environmental control apparatus 140 may comprise additional layers of a phase change material as will be further described in reference to FIG. 2. The phase-change material (PCM) may include a substance with relatively high heat of fusion which, by melting and solidifying at a specific temperature, is capable of absorbing, storing and releasing relatively large amounts of energy.

The environmental control apparatus 140 and/or the container 104 may comprise one or more detectors 218 for detecting one or more environmental conditions of the substance (e.g. drug 110), such as the drug temperature, as described above, or any other parameter of the drug 110, such as color, clarity or transparency, for example.

In some embodiments, the clarity of the substance may be detected, by transmitting light through the chamber 106 and detecting the light attenuation by detector 218. The clarity of a drug may be indicative of the drug efficacy. For example, the efficacy of insulin may be reduced when the drug is cloudy.

The detector 218 may be configured to detect use of the substance (e.g. drug 110), such as the last time the drug was dispensed from the container 104 and/or the last time the container 104 was opened. The detection of use of the substance may be performed in any suitable manner by detecting any change in the container 104 associated with dispensing the substance. In a non-limiting example, the release of the needle cover 122 prior to delivery of the drug 110 may be detected and indicate use of the drug 110. In some embodiments, wherein the pen injector 108 is configured with a removable cartridge, the removal of an existing cartridge and/or insertion of a new cartridge may be detected and indicative of use of the drug 110.

In some embodiments, the movement (e.g. pressing or turning) of the setting knob 126 may be detected by detector 218 and may be indicative of preparation of the substance for use.

In some embodiments, during removal of the container 104 from the environmental control apparatus 140 the detachment of the protrusion 256 (see insert in FIG. 1A) of environmental control apparatus 140 from the matching recess 258 of container 104 may be detected by detector 218 and may be indicative of preparation the substance for use.

In some embodiments, the detector 218 may be configured to detect reflection of light from the container and/or the environmental control apparatus 140, such that the changes in the reflection may be indicative of use of the substance. For example, during the storage state, the cap 230 (FIG. 1A) or tube 240 (FIG. 2) may cover the chamber 106 and therefore there is no reflection of light from the substance. In shifting to the use state, the cap 230 or tube 240 may be removed, thereby exposing the substance to light, which reflection may be detected.

In some embodiments, the environmental control apparatus 140 and/or the container 104 may comprise a counter or timer 220 for detecting the duration of time since previous use of the substance, such as the previous delivery of the drug, for example.

The quantity of used substance, such as the dose of the delivered drug 110, as well as the quantity of substance remaining in the container 104 following use, may be detected in any suitable manner, such as by methods described in reference to FIGS. 26-30.

The environmental control apparatus 140 and/or the container 104 may comprise one or more indicators 222, such as LED indicators or a small electronic display for example. The indicators 222 may indicate one or more environmental conditions of the substance (e.g. drug 110), such as the drug temperature, or any other parameter of the drug 110, such as color, clarity or transparency, for example.

The indicator 222 may be configured to indicate use of the substance, the quantity of the used substance, the time the substance was last used, the last time the container 104 was opened and/or past occurrences of use of the substance. The indicator 222 may be configured to indicate the history of the substance, such as to indicate past deviations from the required temperature range. The indicator 222 may also be configured to indicate other parameters related to the container 104 or the environmental control apparatus 140, such as the remaining battery power.

In some embodiments, the environmental control apparatus 140 may comprise the ECS configured for controlling at least one environmental condition of a drug contained within the DDSD. The ECS may include the ECM 162. In some embodiments, the ECS may include one or more of a power source (e.g. battery 164), a controller 166, at least one electrical contact, at least one indicator 222, at least one switch (e.g. state switch 800 or thermal switch 650 of FIGS. 18A-19B), at least one environmental condition sensor (e.g. sensor 184), a wireless transceiver (e.g. communication means 248), a phase change material (e.g. phase change material layer 260 of FIG. 3) and at least one heat dissipater (e.g. heat dissipater 190).

The ECS may be configured to receive at least a portion of the DDSD. At least one environmental condition of the drug 110 contained within the DDSD may be controlled by the ECM 162 to be within the predetermined range.

In some embodiments, the ECS may be shaped to mechanically fit the DDSD. For example, the ECS may be formed as a cap, (e.g. cap 230 of FIGS. 1A and 1B) insertable on a DDSD. The ECS may be formed as a tube (e.g. tube 240 of FIG. 2) for receiving the DDSD. In some embodiments, the ECS may be shaped to mechanically fit the chamber 106 within the DDSD (e.g. the enclosure 356 of FIG. 7). In some embodiments The ECS may be shaped to mechanically fit the DDSD and to be at least partially inserted therein (e.g. the ECM 162 and base 610 mechanically fitting the ampule 580 of FIG. 16).

Figure 7:
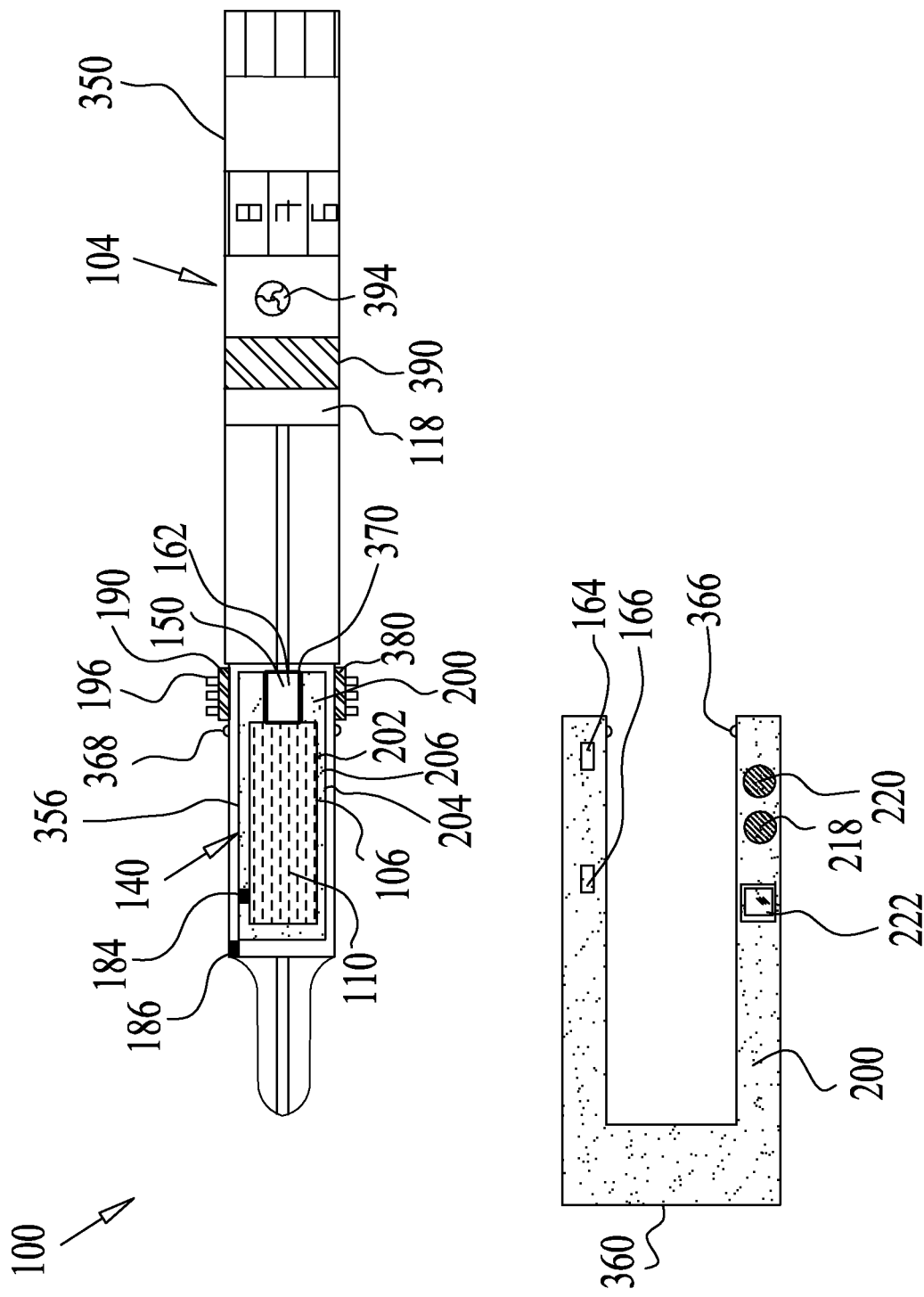
FIG. 7 is a schematic illustration of an exemplary substance control system according to some embodiments of the present disclosure.

In some embodiments, the ECS may be configured to encapsulate the DDSD, e.g. tube 240 of FIG. 2, or may be configured to at least partially enclose a portion of the DDSD, e.g. cap 230 of FIGS. 1A and 1B, wherein the interior of the cap is configured to enclose at least a portion of a drug reservoir of the DDSD or enclosure 356 of FIG. 7 enclosing the chamber 106 of the DDSD.

The ECS may be configured in any suitable shape or form such as a cylinder, a tube, a cap, an oblong enclosure, or an enclosure, for example.

As seen in FIGS. 1A and 1B, the environmental control apparatus 140 comprising the ECS may be formed in any suitable configuration, such as a cap 230 insertable on at least a portion of the container 104, as seen in FIGS. 1A and 1B or as a ring or jacket enclosing the container 104.

In some embodiments, the cap 230 may be configured to replace an existing, conventional cap of a conventional container, such as the injection pen 108. In some embodiments, the cap 230 may be configured to be inserted over an existing, conventional cap of the container 104.

Turning to FIG. 2, it is seen that the environmental control apparatus 140 of FIGS. 1A and 1B may be formed as a tube 240. The tube comprises a detachable first portion 242 and second portion 244 formed for insertion of the environmental control apparatus 140 therein and removal therefrom. In the embodiment of FIG. 2, the first portion 242 may comprise the ECM 162, such as the TEC or any other active temperature controlling element, as well as the thermal transmitter 170 and thermal conductors 180. The second portion 244 may comprise the battery 164 and the controller and electronics 166, it being appreciated that the components of the environmental control apparatus 140 may be placed at any suitable location. In some embodiments, the first portion 242 and second portion 244 comprise the thermal insulation 200.

Heat may be dissipated by heat dissipater 190 forming at least a portion of a cover 246 of tube first portion 242. In some embodiments, cover 246 may further comprise heat dissipating fins 196 or any other heat dissipating element. A cover 247 of the second portion 244 may be formed of plastic or any other suitable material. The first portion 242 may terminate at any suitable location parallel to the container 104, such as at a location overlying the chamber 106 or any other section of the container 104.

The first portion 242 may be engaged with second portion 244 in any suitable manner, such as by a threaded engagement or a snap-fit engagement, for example.

In some embodiments, the first portion 242 may be configured to replace an existing, conventional cap of a conventional container, such as the injection pen 108, and second portion 244 may be engaged with the first portion 242. In some embodiments, the first portion 242 may be configured to be inserted over an existing, conventional cap of the container 104 and second portion 244 may be engaged with the first portion 242.

As seen in FIG. 2, the environmental control apparatus 140 and/or the container 104 may be configured for transmitting information from components thereof by wireless or wired communication means 248. The information may be related to the environmental condition of the substance or any other information related to the substance control system 100. In a non-limiting example, sensors or detectors (e.g. sensors 184 and/or 186) may be configured to detect a signal and/or any data relating to the operation or use of the substance control system 100. Such signal/data may be transmitted via the wireless or wired communication means 248 to a tracking or communication device 250, to a central database 252, and/or from the device 250 to the central database 252. The transmission may be performed in any suitable manner, such as wirelessly, via an analog short range communication mode, or a digital communication mode including WIFI or Bluetooth or cellular means, or via a wired connection or to any remote device to forward the collected data. Additional examples for transmission may be via a network. The network may comprise, the cloud, a local area network (LAN), a wide area network (WAN), or a global network, for example. The network may be part of, or comprise any suitable networking system, such as the Internet, for example, or Intranet. Generally, the term "Internet" may refer to the worldwide collection of networks, gateways, routers, and computers that use Transmission Control Protocol/Internet Protocol ("TCP/IP") and other packet based protocols to communicate therebetween.

In some embodiments, the device 250 may comprise at least one of a remote device, a computer, a cellular phone, smartphone, a tablet, and/or desktop mobile device. In some embodiments, the device 250 may pair with the environmental control apparatus 140 by imaging a LED indicator formed on the environmental control apparatus 140 or by any other identification mechanism.

The central database 252 may comprise any suitable device or function for storage of the data and/or analysis thereof. The central database may comprise a processor and/or memory. In a non-limiting example, the central database 252 may comprise at least one of a computer, PC, laptop, tablet, smartphone, media player and other mobile or desktop device.

The data may be used by a physician, caretaker or the user (e.g. patient) to track the administration of the substance, e.g. drug 110. Additionally, the data may be used to alert the user upon deviation from the predetermined environmental condition range or threshold. Additionally, the data may be used to alert the user upon reduction of the efficacy of the drug 110 due to excess heat or any other relevant environmental condition and/or parameter, such as upon passage of the drug expiration date, for example. Moreover, the data may be used to inform the user the time the substance was last used, the quantity of used substance, the last time the container 104 was opened and/or past occurrences of use of the substance. Furthermore, the data may be used to inform the user the next time the substance is to be used and possibly the quantity that needs to be used. The information and alert may be provided in any suitable manner such as by an optical or audial signal.

In some embodiments, the data may be used to monitor delivery of drugs in various geographical locations. For example, whereupon drugs 110 are to be transported to a multiplicity of locations, e.g. by a global health organization, or a pharmaceutical distributor, the data may be used to monitor the location of the drug delivery device, such as by a GPS element provided in the substance control system 100.

In some embodiments, an alert may be transmitted to an appropriate entity in case of an undesired deviation from predetermined environmental conditions or the predetermined location. The alert and/or monitoring may be performed for a single environmental control apparatus 140 and/or container 104 in a single location, or for a plurality of environmental control apparatuses 140 and/or containers 104 in a single location or in a plurality of locations.

In some embodiments, the environmental control apparatus 140 may be configured to track the type of substance (e.g. drug 110) placed within the container 104. For example, the environmental control apparatus 140 may include a passive electronic ID thereon (e.g., RFID), and an ID reader. Through the communication means 248, the environmental control apparatus 140 may be connected by wire or wirelessly via a network to the device 250 and/or to central database 252 to forward the collected data indicative of the substance type.

Any one of the embodiments of the environmental control apparatus 140 of FIGS. 1A-25 may be configured for transmitting information therefrom to the device 250 and/or central database 252.

In some embodiments, the environmental control apparatus 140 and/or the container 104 may comprise an identification element. The environmental control apparatus 140 may be configured to detect the identification element placed on a container 104. In some embodiments, an environmental control apparatus 140 may be configured to operate with a selected commercial brand of container 104. The identification element may be used to allow activation of the environmental control apparatus 140 upon identification of the selected container 104.

The identification element may comprise an RFID element, an electrical element, such as a wire or a sensor and/or a mechanical element, such as an activation pin or an identification element 254. The identification element 254 (FIG. 1A) may comprise a feature shaped as a protrusion 256 protruding from the environmental control apparatus 140 and configured to match a recess 258 formed on the container 104 (or vice versa).

Figure 3:
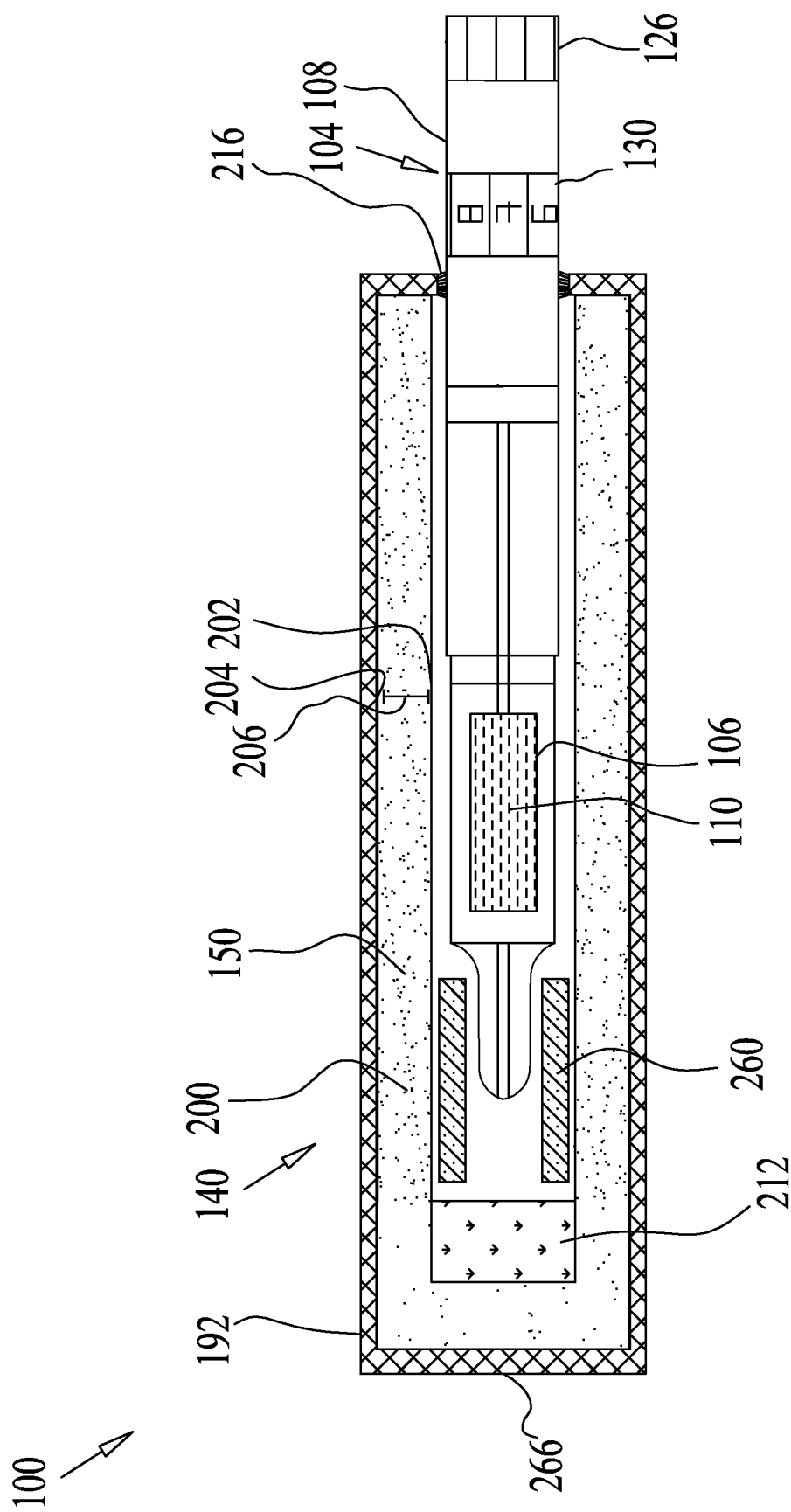
FIG. 3 is a schematic illustration of an exemplary substance control system according to some embodiments of the present disclosure.
Figure 4:
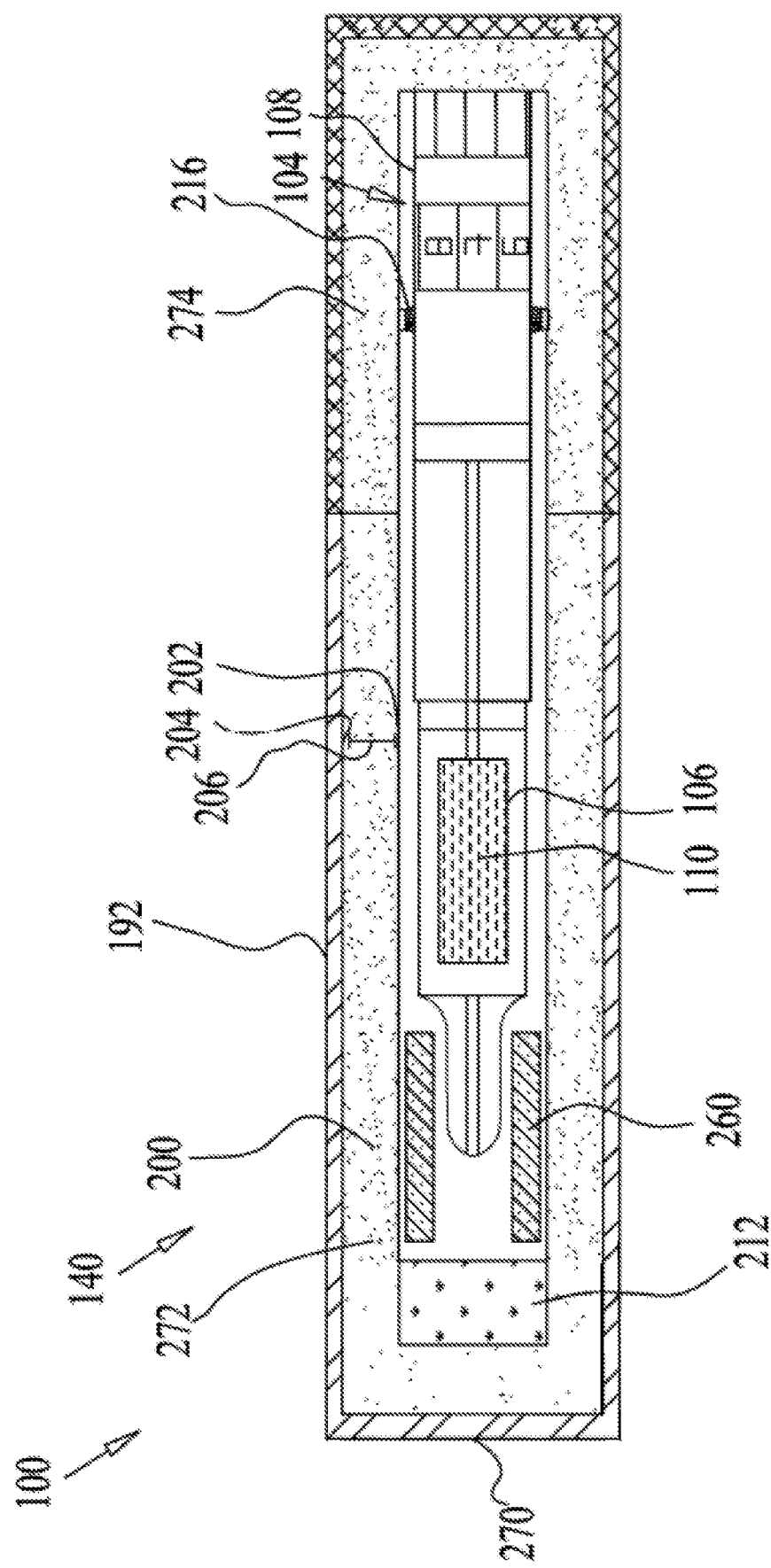
FIG. 4 is a schematic illustration of an exemplary substance control system according to some embodiments of the present disclosure.

FIGS. 3 and 4 each illustrate an exemplary substance control system 100 according to some embodiments. As seen in FIGS. 3 and 4, the environmental control element comprises passive temperature controlling elements, such as a layer of thermal insulation 200.

The cover 192 of the environmental control apparatus 140 may be formed of any suitable material, such as plastic. The cover 192 may be formed of an opaque material for preventing penetration of light therein.

In some embodiments, the environmental control apparatus 140 may comprise a phase change material formed as a layer 260 underlying, at least partially, a layer of the thermal insulation 200. The phase change material layer 260 further absorbs heat flux which may pass through the thermal insulation 200 before it reaches the substance (e.g. drug 110). The phase-change material is configured to aid in control of the environmental condition of the substance (e.g. drug 110) contained in the container (e.g. the DDSD).

In some embodiments, the phase change material layer 260, may be arranged within the thermal insulation 200, such as within the gap 206 of the INSULON® material or a similar constructed material or outside of the INSULON® material.

As seen in FIGS. 3 and 4, the container 104 comprises the injection pen 108. In FIG. 3, the environmental control apparatus 140 is formed as a cap 266 insertable on at least a portion of the container 104. In some embodiments, the environmental control apparatus 140 may be formed as a ring or jacket enclosing the container 104 or any other suitable configuration, such as a tube 270 shown in FIG. 4. In the embodiment of FIG. 4 the tube 270 comprises a first portion 272 and a second portion 274. The first portion 272 and the second portion 274 may comprise the environmental control element 150 including the layer of thermal insulation 200 and the phase change material layer 260, it being appreciated that the components of the environmental control apparatus 140 may be placed at any suitable location.

In some embodiments, the phase change material layer 260 is obviated from the environmental control apparatus 140 of FIGS. 3 and 4 and the environmental control element 150 may comprise thermal insulation 200 only.

Figure 5:
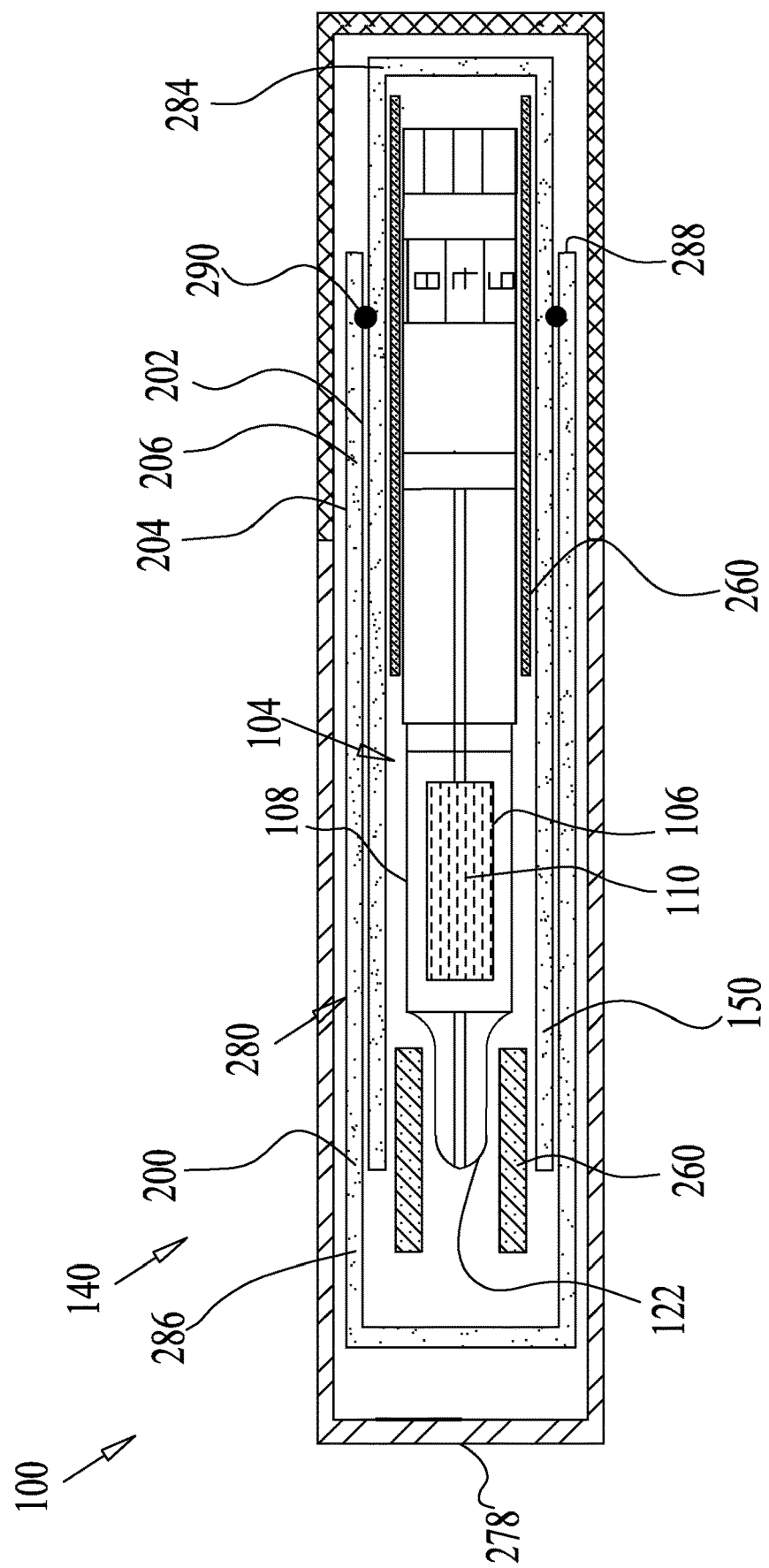
FIG. 5 is a schematic illustration of an exemplary substance control system according to some embodiments of the present disclosure.

FIG. 5 illustrates an exemplary substance control system 100 according to some embodiments of the present disclosure. As seen in FIG. 5, the environmental control apparatus 140 may comprise a tube 278 including an insulating construction 280 formed of at least two mutually insertable inner and outer insulating enclosures 284 and 286. The inner insulating enclosure 284 may be formed in a cup-like shape and inserted into the oppositely facing outer insulating enclosure 286, formed in a cup-like shape as well. Insulating enclosures 284 and 286 may each comprise a multi-layered material, formed of walls 202 and 204 wherein vacuum is established between the gap 206 formed therebetween. A sealing element 290, such as a gasket or an O-Ring, may be placed between the insulating enclosures 284 and 286 to insure an inner space enveloped between the two insulating structures 284 and 286 is sealed from the ambient environment.

In the absence of the outer insulating enclosure 286, heat may infiltrate into the environmental control apparatus 140 around an edge 288 of the inner insulating enclosure 284 and reach the container 104. The configuration of the two mutually insertable, oppositely facing inner and outer insulating enclosures 284 and 286, may prevent this infiltration of heat.

The walls 202 and 204 of inner and outer insulating enclosures 284 and 286 may extend along the container 104 to any suitable length, such as parallel to the injection pen 108 and extending over the needle cover 122, as seen in FIG. 5. In some embodiments, the walls 202 and 204 may partially overlay the entire chamber 106 or a portion thereof or may terminate prior to the chamber 106.

In some embodiments, the inner insulating enclosure 284 may be placed outwardly and the outer insulating enclosure 286 may be placed within the inner insulating enclosure 284.

In some embodiments, the environmental control apparatus 140 of FIG. 5 may further include the phase change material layer 260 shown in FIG. 3, placed at any suitable location, such as intermediate the insulating construction 280 and the container 104.

Figure 6:
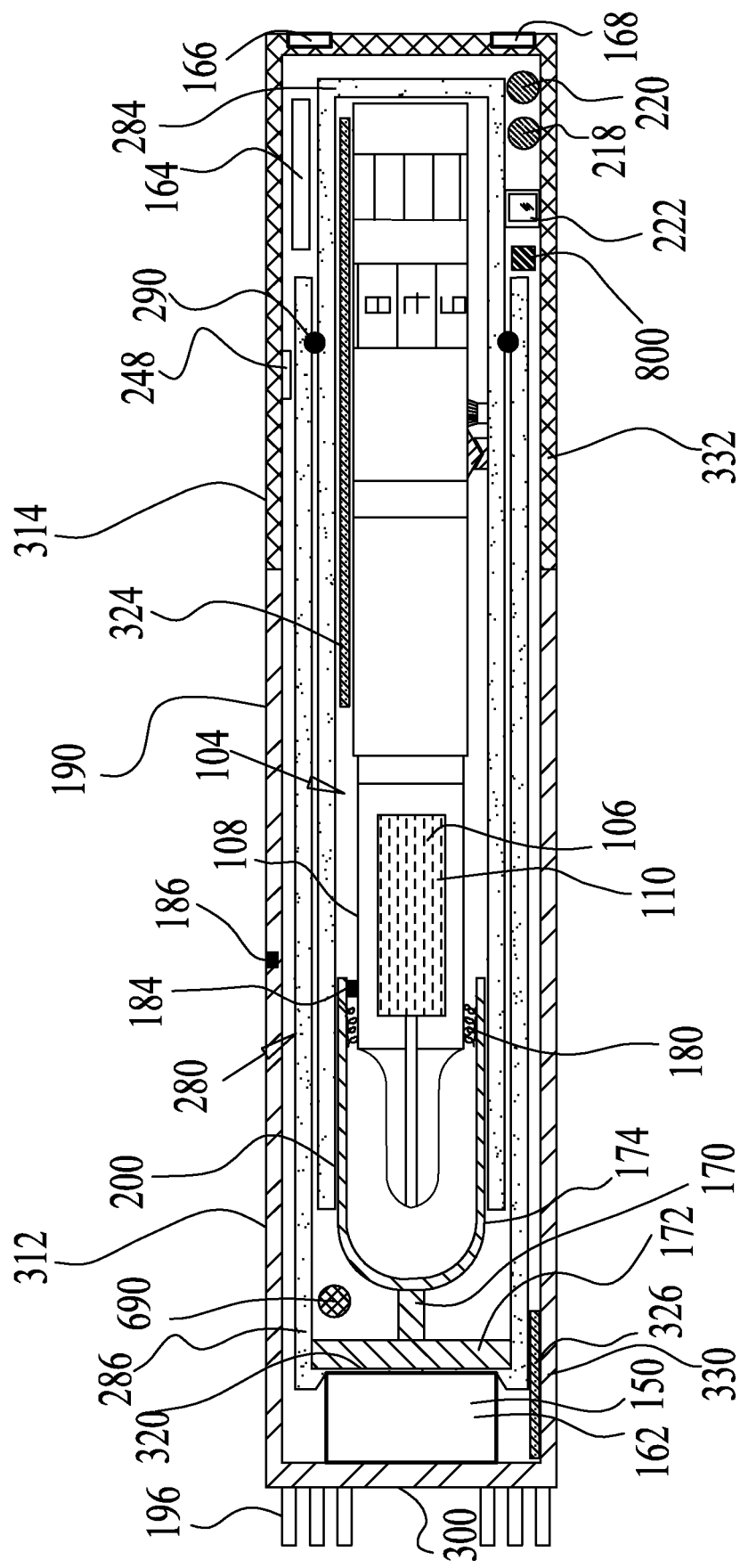
FIG. 6 is a schematic illustration of an exemplary substance control system according to some embodiments of the present disclosure.

FIG. 6 illustrates an exemplary substance control system 100 according to some embodiments of the present disclosure. As seen in FIG. 6, the environmental control apparatus 140 may be formed as a tube 300 enclosing the container 104. The tube 300 may comprise a detachable first portion 312 and a second portion 314. In the embodiment of FIG. 6 the first portion 312 may comprise the ECM 162 and the second portion 314 may comprise the battery 164 and the controller and electronics 166, it being appreciated that the components of the environmental control apparatus 140 may be placed at any suitable location. The ECM 162 may comprise the thermoelectric cooling/heating element.

The ECM 162 is in contact with the base portion 172 of the thermal transmitter 170. The protruding portion 174 is engaged with the chamber 106. The thermal conductors 180 may be provided along at least a portion of the chamber 106 or the container 104. Electrical connections (not shown) between the battery 164, and the controller and electronics 166 and the ECM 162 and any other electrical component are provided.

The environmental control apparatus 140 and/or the container 104 may include at least one or more substance temperature sensors 184 and/or at least one or more ambient temperature sensors 186.

In some embodiments, the first portion 312 and second portion 314 comprise the thermal insulation 200. The thermal insulation 200 may be formed in any suitable configuration, such as comprising the insulating construction 280 including the two mutually insertable inner and outer insulating enclosures 284 and 286, as described in reference to FIG. 5.

Thermal conductivity between the ECM 162 and the chamber 106 may be provided in any suitable manner. In the embodiment of FIG. 6, the thermal conducting walls 202 and 204 of the outer insulating enclosure 286 may be adjoined at to create thermal contact therebetween at a thermal conducting area 320 adjacent to the ECM 162. Thus the thermal insulation 200 is excluded at area 320 allowing thermal conduction from the ECM 162, via adjoined walls 202 and 204 and thermal transmitter 170, to chamber 106. In some embodiments, walls 202 and 204 may be formed with an aperture at area 320, thereby excluding the thermal insulation 200 at area 320 and allowing thermal contact between the ECM 162 and the thermal transmitter 170.

In some embodiments, the environmental control apparatus 140 may comprise the phase change material formed as an inner layer 324 underlying at least partially a layer of the thermal insulation 200 for further absorbing heat flux (e.g. from the ambient environment or from the ECM 162) which may pass through the thermal insulation 200 before it reaches the substance.

In some embodiments, an outer layer 326 of a phase change material may be provided intermediate at least a portion of the thermal insulation 200 and a cover 330 of tube first portion 312. The outer phase change material layer 326 may be provided to absorb the heat flux generated by the ECM 162. In some embodiments, the phase change material layer 326 may comprise multiple phase change materials, wherein each phase change material is configured with a different phase change temperature threshold, thereby allowing the phase change material layer 326 absorb the heat fluxes generated at different temperatures.

Heat may be dissipated by heat dissipater 190 forming at least a portion of cover 330 of tube first portion 312, which in some embodiments may further comprise heat dissipating fins 196 or any other heat dissipating element. A cover 332 of the second portion 314 may be formed of plastic or any other suitable material. The first portion 312 may terminate at any suitable location parallel the container 104, such as at a location overlying the chamber 106 or any other section of the container 104.

The first portion 312 may be engaged with second portion 314 in any suitable manner, such as by a threaded engagement or a snap-fit engagement, for example.

The environmental control apparatus 140 of any of FIGS. 1A-25, may be reusable or disposable or may comprise both a reusable and a disposable portion. The container 104 may be configured for single use, such as an ampule (FIG. 16) or for multiple use, such as a refillable injection pen.

The environmental control apparatus 140 of any of FIGS. 1A-25 may be formed as a handheld, portable device.

In any of the embodiments of FIGS. 1A-25 the power source may comprise energy harvesting devices configured to generate energy which can further be stored. Combining such energy harvesting devices in apparatuses 140 that require the battery 164 to operate, may reduce the battery size. In some embodiments, the energy harvesting device may be used to recharge the battery 164 based on the temperature gradient between the temperature within chamber 106 and the ambient environment temperature external to the environmental control apparatus 140. The energy stored in the battery 164 may be used to control the temperature. In some embodiments, a thermogenerator chip may be used for generating energy exploiting very low temperature differences (e.g. 5 C.°). Such a chip may be, for example, commercially available as a MPG-D655 chip from Micropelt (http://www.micropelt.com). Additionally, the power source may comprise an element used for energy storage and incorporated in an electrical circuit. An exemplary energy storage device may be commercially available as the NanoCap by Dais Analytic Corporation of 11552 Prosperous Drive Odessa, Fla. 33556, U.S.A (http://www-.daisanalytic.com/applications/nanocap.html).

In any of the embodiments of FIGS. 1A-25 the environmental control of the substance is targeted to the chamber 106, such that other components within the container 104 are not controlled. For example, in the injection pen 108 of FIG. 1A, the chamber 106 is heated or cooled by the ECM 162 while the piston 118 remains uncontrolled. This targeted control allows the environmental control apparatus 140 to operate using significantly less energy than would have been required if the entire container 104 were heated/cooled.

The environmental control apparatus 140 of the embodiments of FIGS. 1A-6 are configured to be inserted on the container 104. In some embodiments, the environmental control apparatus 140 may be housed within the container 104, such as shown in FIGS. 7 and 8.

Figure 8:
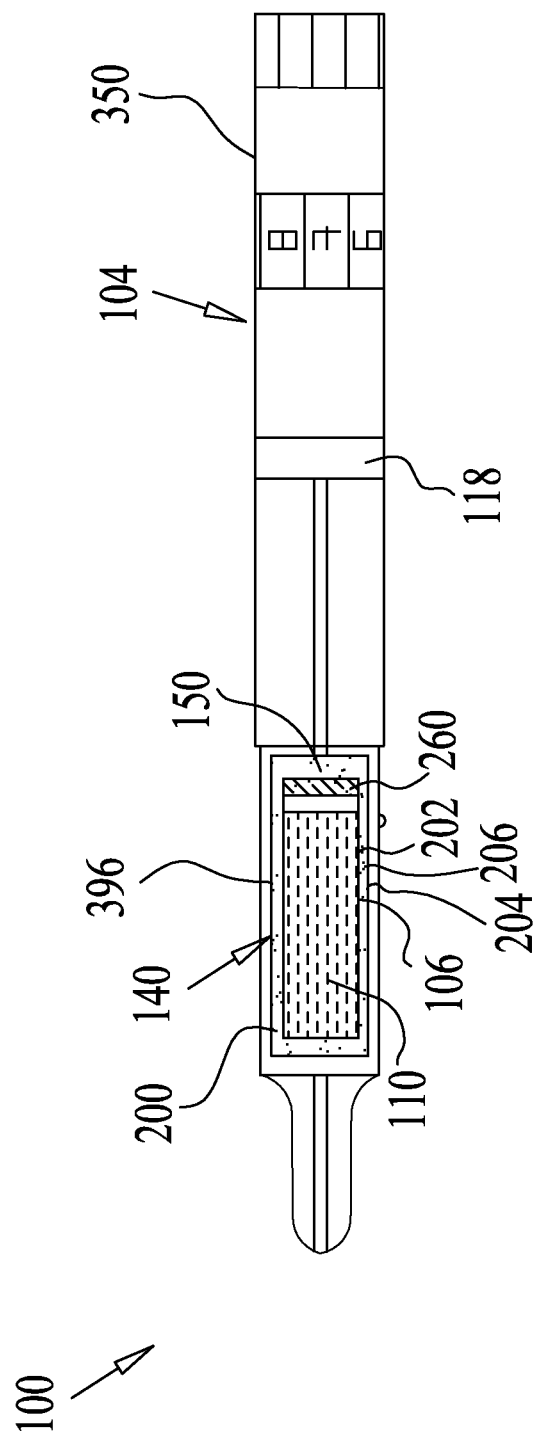
FIG. 8 is a schematic illustration of an exemplary substance control system according to some embodiments of the present disclosure.

FIGS. 7 and 8 are each a schematic illustration of an exemplary substance control system according to some embodiments of the present disclosure.

As seen in FIG. 7, the container 104 comprises an injection pen 350 including the chamber 106 containing the drug 110 therein. The injection pen 350 may be disposable or reusable. The environmental control apparatus 140 may be placed within the container 104 around the chamber 106 or in proximity thereto and may be configured to control and maintain the environmental conditions of the substance within the chamber 106.

The environmental control apparatus 140 may comprise an enclosure 356 including the ECM 162 comprising the TEC or any other active temperature controlling element. The enclosure 356 may be formed of the thermal insulation 200. In some embodiments, the thermal insulation 200 may comprise the multi-layered material, formed of walls 202 and 204 with the evacuated gap 206 therebetween. The ECM 162 may be placed at any suitable location for thermal and/or mechanical contact with the chamber 106. As seen in FIG. 7, the ECM 162 is mounted within an aperture 370 formed within the enclosure 356, thereby excluding the thermal insulation 200 at the aperture 370 and allowing thermal contact between the ECM 162 and the chamber 106.

The battery 164 and the controller and electronics 166 may be embedded, or otherwise contained, within the enclosure 356 or within the injection pen 350, or within a cap 360 covering the injection pen 350, as shown in FIG. 7. The cap 360 may comprise electrical contacts 366 for electronic communication with corresponding electrical contacts 368 of the enclosure 356.

At least one or more substance temperature sensors 184 may be provided in proximity to the chamber 106 and/or at least one or more ambient temperature sensors 186 may be provided in proximity to the ambient environment at any suitable location, such as on the injection pen 350 or cap 360.

The detectors 218, timers 220 and/or indicators 222 may be placed on cap 360, as seen in FIG. 7, or on the enclosure 356 or on the injection pen 350.

Heat may be dissipated by heat dissipater 190 forming at least a portion of a cover or ring 380 surrounding the pen injector 350. In some embodiments, heat dissipating fins 196 or any other heat dissipating element may be provided. In some embodiments, the heat dissipater 190 may comprise a heat sink 390 placed within the pen injector 350. The heat may be removed from the ECM 162 via the piston 118 configured for conducting heat to heat sink 390. Additional methods for removing/adding heat from/to the chamber 106 may be used, including, for example, micro-fans and/or heat sink elements. A micro-fan 394 may be placed within the container 104.

In some embodiments, the cap 360 is formed, at least partially, with a layer of thermal insulation 200.

As seen in FIG. 8, the container 104 comprises the injection pen 350 comprising the chamber 106 containing the drug 110 therein. The injection pen 350 may be disposable or reusable.

The environmental control apparatus 140 may be placed within the container 104 around the chamber 106, or in proximity thereto and may be configured to control and maintain the environmental conditions of the substance within the chamber 106.

The environmental control apparatus 140 may comprise an enclosure 396 including the environmental control element 150 comprising the layer of thermal insulation 200 for shielding the chamber 106 from the ambient environmental conditions. As described in reference to FIG. 1A, the thermal insulation 200 may be realized by the multi-layered material, formed of walls 202 and 204. The gap 206 defined by a space between the walls 202 and 204 may be, at least partially, evacuated. The phase change material layer 260 may be provided and, at least partially, underlie the thermal insulation 200.

In some embodiments, the phase change material layer 260 is obviated from the environmental control apparatus 140 of FIG. 8 and the environmental control element 150 may comprise the thermal insulation 200 only.

FIGS. 9-12 are each a schematic illustration of an exemplary substance control system according to some embodiments of the present disclosure.

Figure 9:
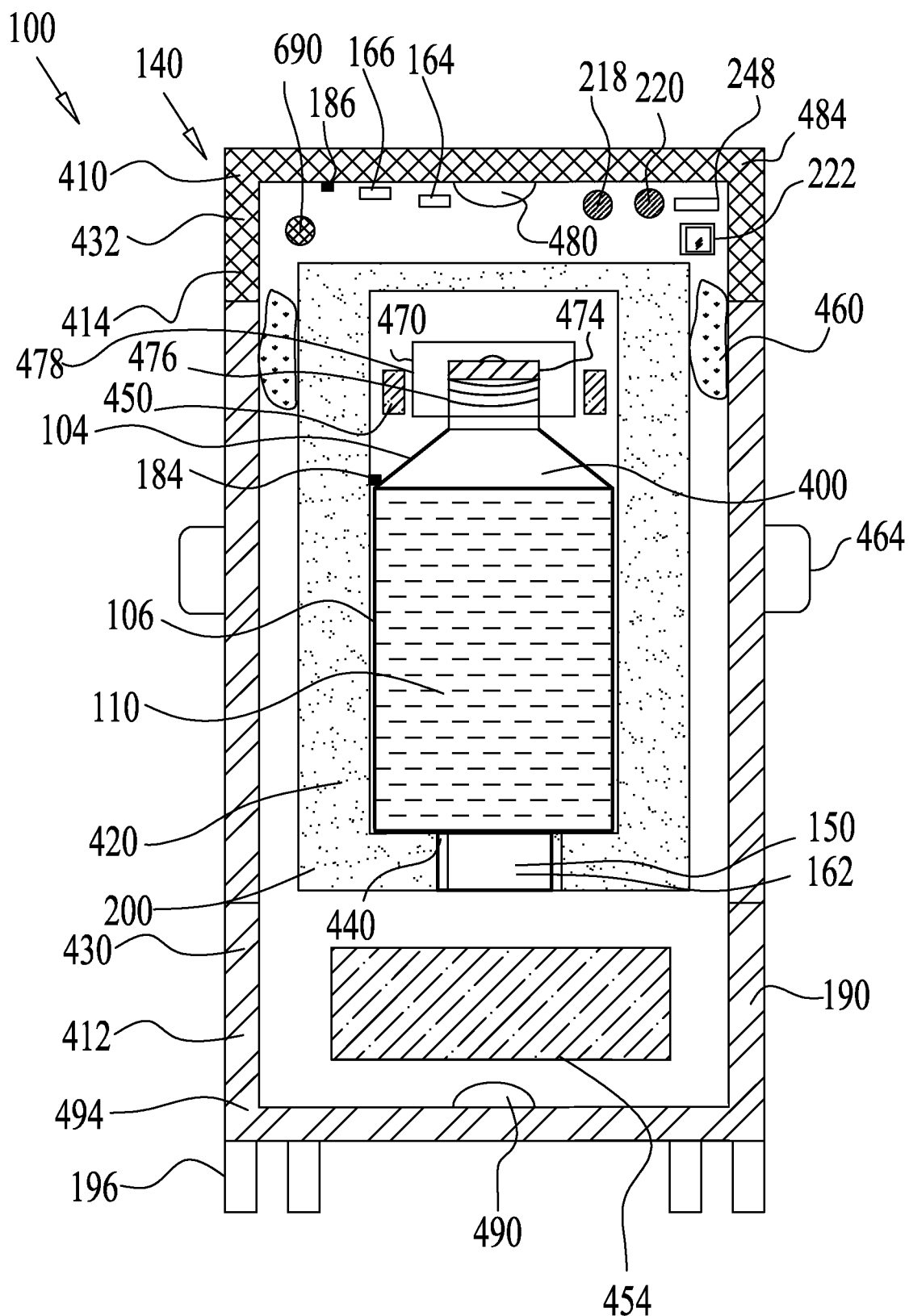
FIG. 9 is a schematic illustration of an exemplary substance control system according to some embodiments of the present disclosure.
Figure 10:
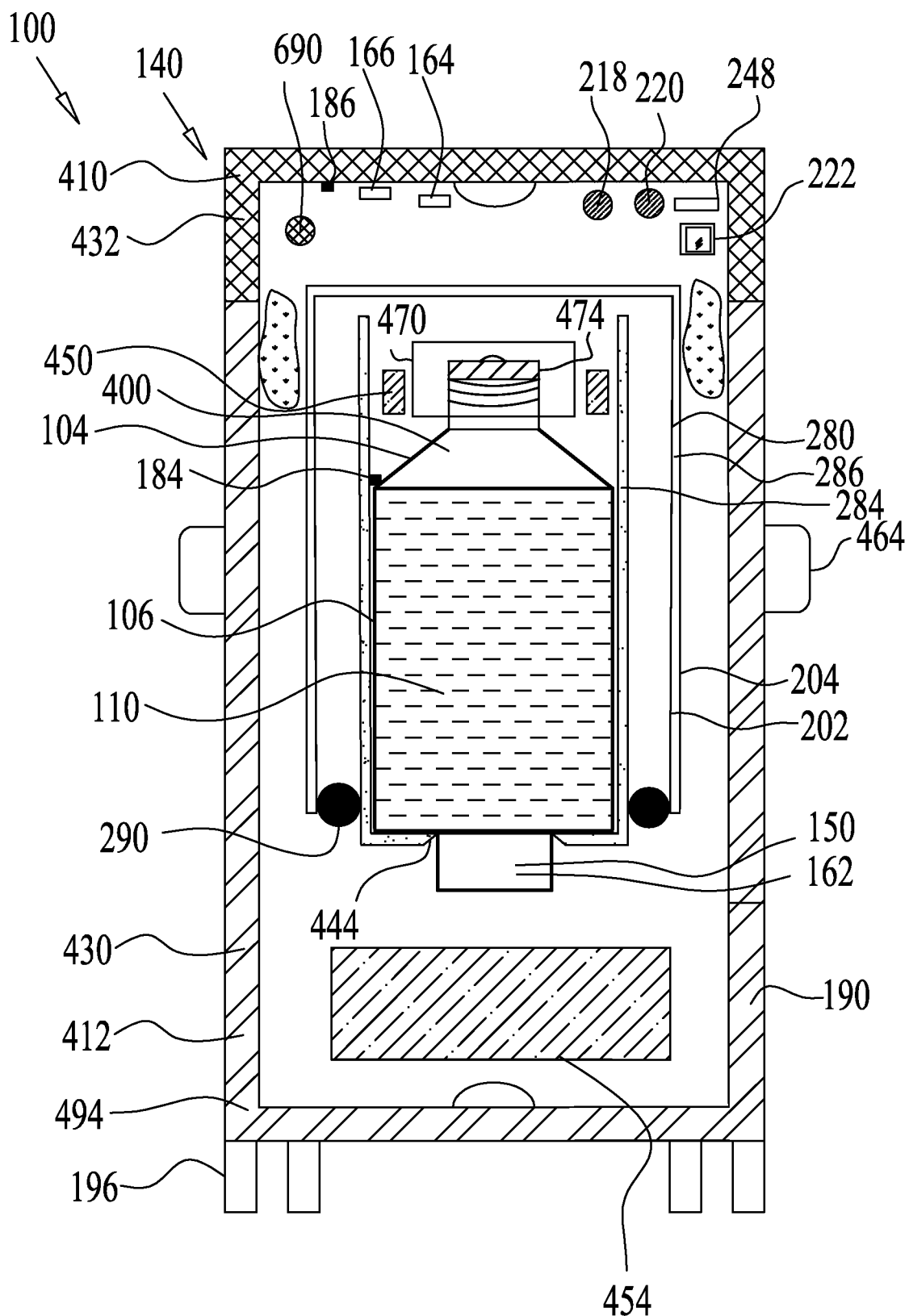
FIG. 10 is a schematic illustration of an exemplary substance control system according to some embodiments of the present disclosure.

As seen in FIGS. 9 and 10, the container 104 comprises an ampule or vial 400 including the chamber 106 containing a substance therein. The vial 400 may be a drug vial for single or multiple use and may be disposable or reusable.

In FIGS. 9 and 10, the environmental control apparatus 140 may be formed as a tube 410 comprising a detachable first portion 412 and second portion 414.

The first portion 412 may be engaged with second portion 414 in any suitable manner, such as by a threaded engagement or a snap-fit engagement, for example.

In the embodiments of FIG. 9 the first portion 412 may comprise the ECM 162 and the second portion 414 may comprise the battery 164 and the controller and electronics 166, it being appreciated that the components of the environmental control apparatus 140 may be placed at any suitable location. The ECM 162 may comprise the TEC or any other active temperature controlling elements Electrical connections (not shown) between the battery 164, and the controller and electronics 166 and the ECM 162 and any other electrical component are provided.

The thermal conductor 180 (FIG. 1A) and/or brushes 216 may be provided.

The environmental control apparatus 140 and/or the container 104 may comprise one or more detectors 218, timers 220 and/or indicators 222.

The environmental control apparatus 140 and/or the container 104 may include at least one or more substance temperature sensors 184 and/or at least one or more ambient temperature sensors 186.

In some embodiments, as seen in FIG. 9, the first portion 412 and second portion 414 comprise the thermal insulation 200. The thermal insulation 200 may be formed in any suitable configuration, such as a layer of insulating material 420 at least partially underlying a cover 430 and 432 of respective first and second portions 412 and 414. The ECM 162 is mounted within an aperture 440 formed within the insulating material 420, thereby excluding the thermal insulation 200 at the aperture 440 and allowing thermal contact between the ECM 162 and the chamber 106.

In some embodiments, as seen in FIG. 10, the thermal insulation 200 may comprise the insulating construction 280 including the two mutually insertable inner and outer insulating enclosures 284 and 286, as described in reference to FIG. 5. Thermal conductivity between the ECM 162 and the chamber 106 may be provided in any suitable manner. In the embodiment of FIG. 10, the thermal conducting walls 202 and 204 of the outer insulating enclosure 286 may be adjoined to create thermal contact therebetween at a thermal conducting area 444 adjacent to the ECM 162. Thus excluding the thermal insulation 200 at area 444 and allowing thermal conduction from the ECM 162, via adjoined walls 202 and 204 to chamber 106.

In some embodiments, the environmental control apparatus 140 may comprise the phase change material formed as an inner layer 450 underlying, at least partially, a layer of the thermal insulation 200 for further absorbing heat flux (e.g. from the ambient environment or from the ECM 162) which may pass through the thermal insulation 200 before it reaches the substance.

In some embodiments, an outer layer 454 of a phase change material may be provided intermediate at least a portion of the thermal insulation 200 and the cover 430. The outer phase change material layer 454 may be provided to absorb the heat flux generated by the ECM 162. For example, whereupon the ECM 162 comprises the TEC, the TEC generates heat during operation. The outer phase change material layer 454 is provided to assist the heat dissipater 190 to absorb heat from the TEC.

The phase change temperature threshold is the temperature whereupon the phase change material changes its phase. In some embodiments, the threshold temperature of the inner phase change material layer 450 may be selected to ensure the drug 110 will not be heated more than the predetermined temperature range. In some embodiments, the threshold temperature of the outer phase change material layer 454 may be selected such that the phase change material layer 454 will absorb the heat flux to be dissipated by the heat dissipater 190 and yet will remain unaffected by the temperature of the ambient environment.

In some embodiments, the phase change material layer 454 may comprise multiple phase change materials, wherein each phase change material is configured with a different phase change temperature threshold, thereby allowing the phase change material layer 454 to absorb the heat fluxes generated at different temperatures.

Heat may be dissipated by heat dissipater 190 forming at least a portion of the cover 430 of tube first portion 412, which in some embodiments may further comprise heat dissipating fins 196 or any other heat dissipating element. The cover 432 of the second portion 414 may be formed of plastic or any other suitable material. The first portion 412 may terminate at any suitable location parallel the container 104, such as at a location overlying the chamber 106 or any other section of the container 104.

In some embodiments of FIGS. 9 and 10 or any of FIGS. 1A-25, the environmental control apparatus 140 may comprise a shock absorber 460 for absorbing mechanical shock so as to protect the substance during accidental dropping of the container 104.

The environmental control apparatus 140 may be configured with a press-to-release mechanism 464 typically placed on cover 430 or 432 for ease of removal of the vial 400 from the environmental control apparatus 140 and insertion therein, without disturbing the substance.

In some embodiments, use detection by the detector 218 may be performed by detecting structural changes occurring in the vial 400, or any one of the containers 104, upon use thereof. For example, the vial 400 may be formed with a cap 470. The removal of the cap 470 prior to use may be detected by detector 218 and indicative of use of the substance. In some vials 400 upon removal of the cap 470, an underlying seal 474 bulges. The bulging of the seal 470 may be detected by detector 218 and indicative of use of the substance. In an additional example, underlying the cap 470 may be a threaded, external side surface 476 formed on the vial 400. Upon removal of cap 470, the transition from a smooth, external side surface 478 of the cap 470 to the threaded, external side surface 476 of the vial 400 may be detected by detector 218 and indicative of use of the substance. In yet an additional example, the tilting of the vial 400 or container 104 prior to removal of the substance may be detected by detector 218, which may comprise an accelerometer, and may be indicative of use of the substance.

In some embodiments, the environmental control apparatus 140 may comprise an upper protrusion 480 extending towards the vial 400 at a top portion 484 thereof and/or a lower protrusion 490 extending towards the vial 400 at a bottom portion 494 thereof. Upper protrusion 480 and/or lower protrusion 490 may be pressed while the vial 400 is within the environmental control apparatus 140 and may bulge upon removal of the vial 400 from the environmental control apparatus 140. The bulging of the upper protrusion 480 and/or lower protrusion 490 may be detected by detector 218 and indicative of use of the substance.

The environmental control apparatus 140 of FIGS. 9 and 10 may comprise communication means 248 for transmitting information therefrom to the device 250 and/or central database 252.

Figure 11:
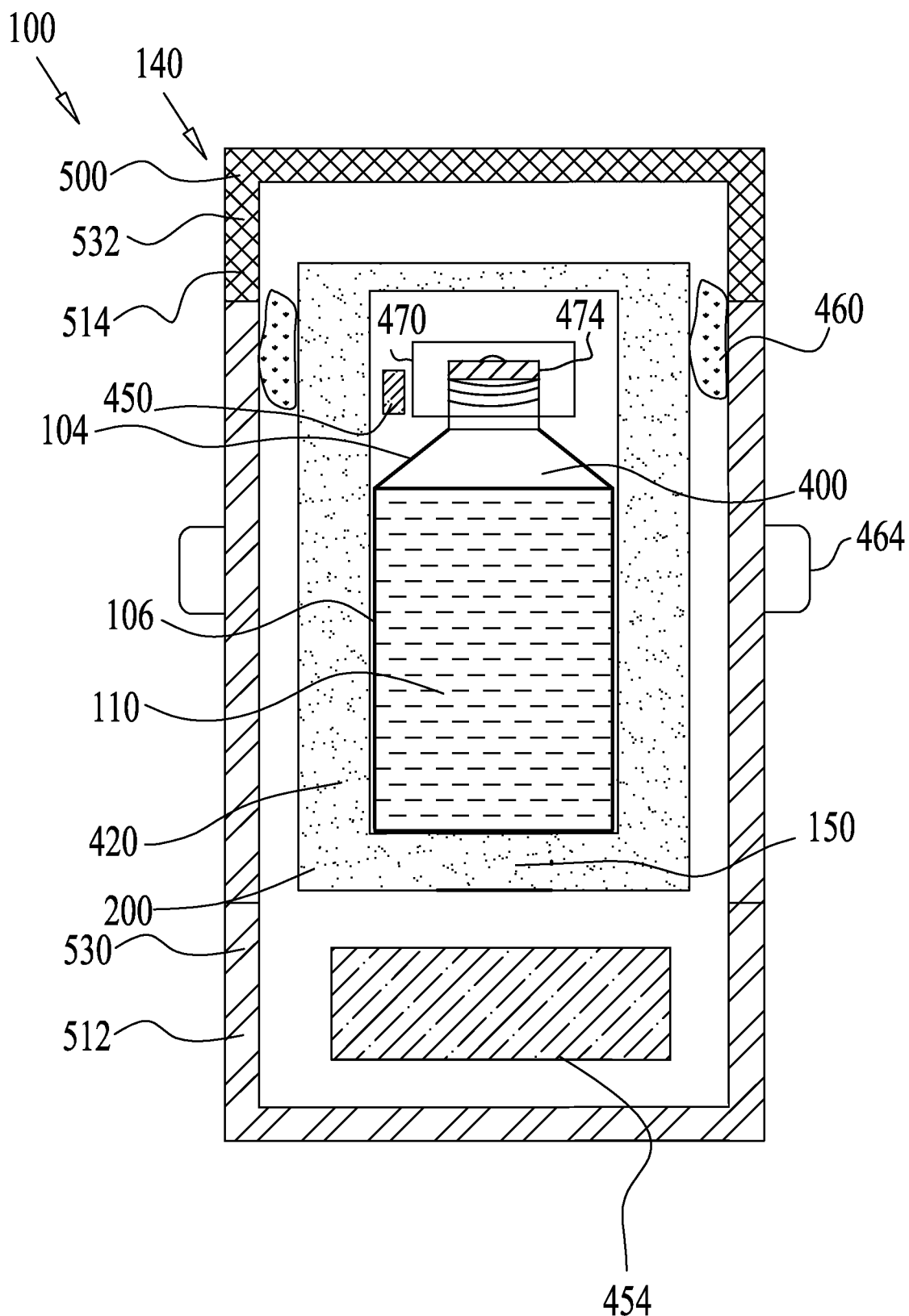
FIG. 11 is a schematic illustration of an exemplary substance control system according to some embodiments of the present disclosure.
Figure 12:
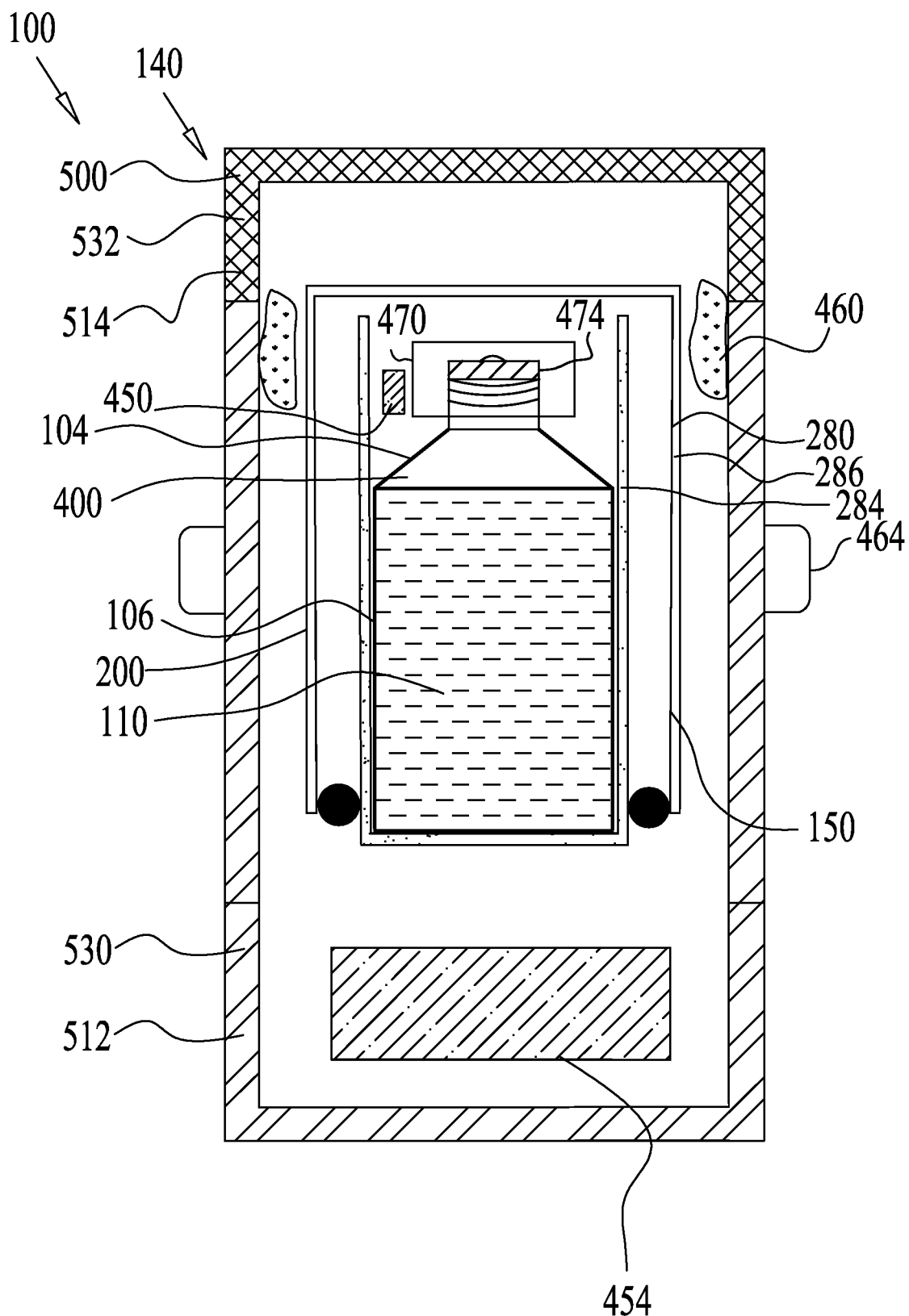
FIG. 12 is a schematic illustration of an exemplary substance control system according to some embodiments of the present disclosure.

FIGS. 11 and 12 each illustrate an exemplary substance control system 100 according to some embodiments. In the embodiment of FIGS. 11 and 12 the environmental control apparatus 140 may be configured as a tube 500 comprising a first portion 512 and a second portion 514.

As seen in FIGS. 11 and 12 the environmental control element 150 comprises passive temperature controlling elements, such as a layer of thermal insulation 200.

In some embodiments, as seen in FIG. 11, the first portion 512 and second portion 514 comprise the thermal insulation 200. The thermal insulation 200 may be formed in any suitable configuration, such as a layer of insulating material 520 at least partially underlying a cover 530 and 532 of respective first and second portions 512 and 514.

In some embodiments, as seen in FIG. 12, the thermal insulation 200 may comprise the insulating construction 280 including the two mutually insertable inner and outer insulating enclosures 284 and 286, as described in reference to FIG. 5. Thermal conductivity between the environmental control element 150 and the chamber 106 may be provided in any suitable manner.

In some embodiments, the environmental control apparatus 140 may comprise the phase change material formed as layer 450 underlying at least partially a layer of the thermal insulation 200.

In some embodiments, the phase change material layer 450 is obviated from the environmental control apparatus 140 of FIGS. 11 and 12 and the environmental control element 150 may comprise thermal insulation 200 only.

Covers 530 and/or 532 of the environmental control apparatus 140 may be formed of any suitable material, such as plastic. The covers 530 and/or 532 may be formed of an opaque material for preventing penetration of light therein.

Figure 13:
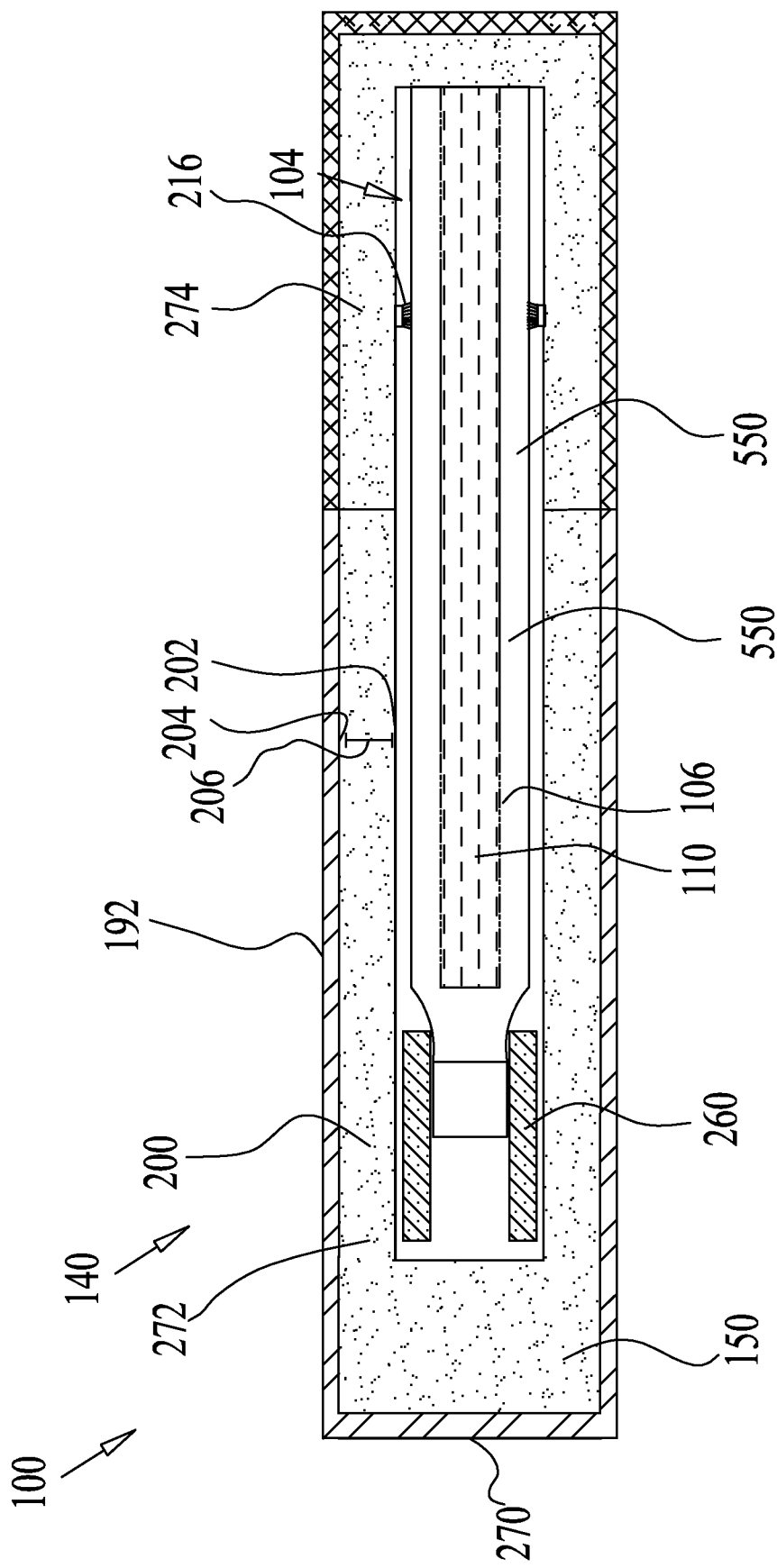
FIG. 13 is a schematic illustration of an exemplary substance control system according to some embodiments of the present disclosure.
Figure 14:
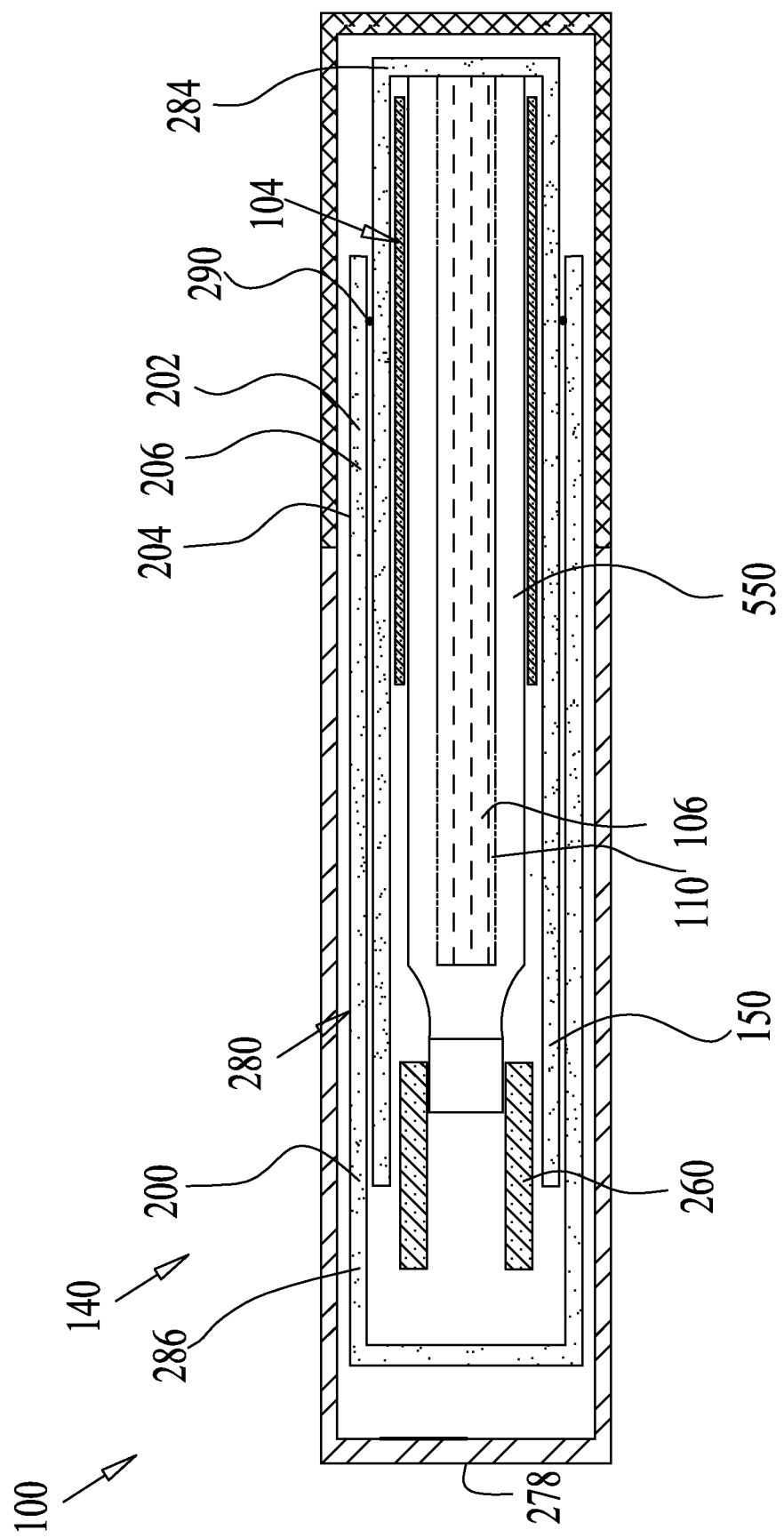
FIG. 14 is a schematic illustration of an exemplary substance control system according to some embodiments of the present disclosure.
Figure 15:
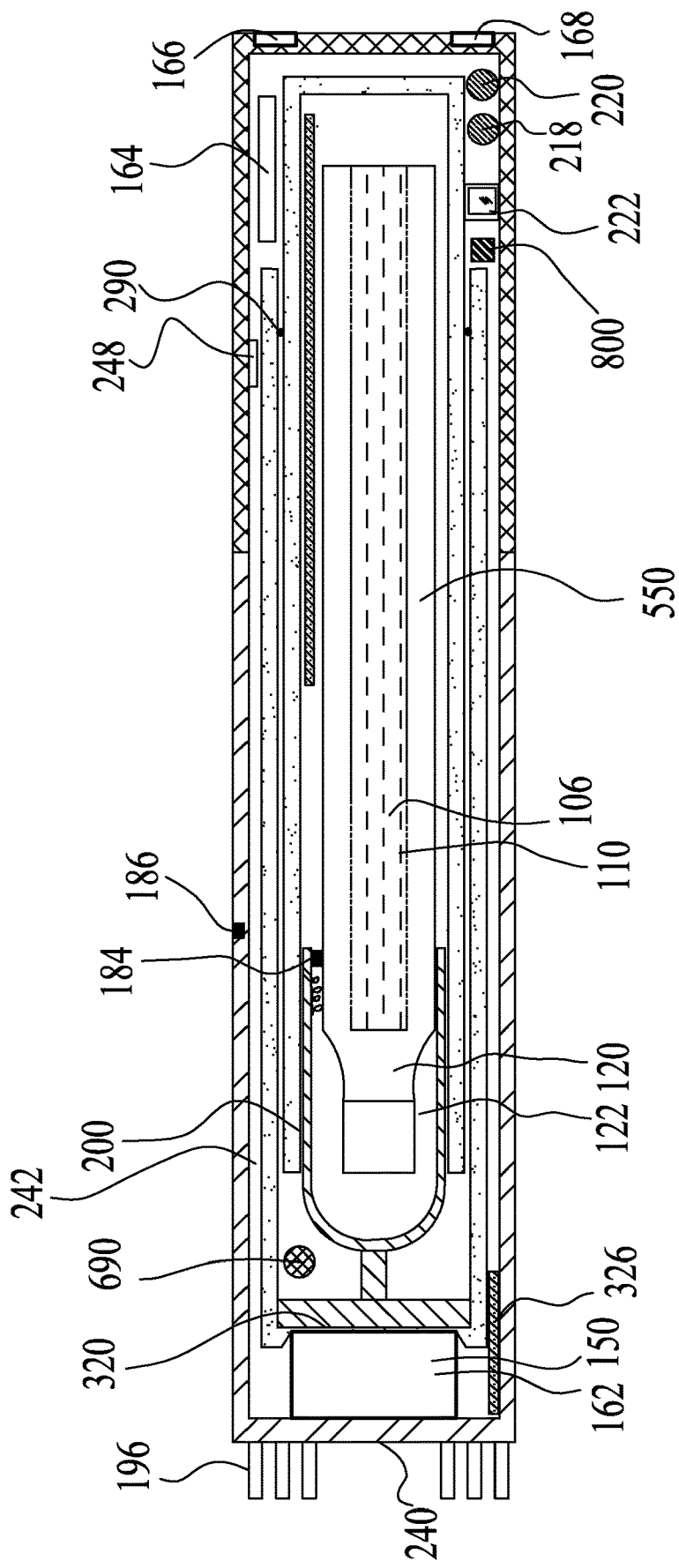
FIG. 15 is a schematic illustration of an exemplary substance control system according to some embodiments of the present disclosure.

FIGS. 13-15 illustrate an exemplary substance control system 100 according to some embodiments of the present disclosure. As seen in FIGS. 13-15, the container 104 comprises a cartridge 550 formed with the chamber 106 for containing a substance therein, such as a drug 110. An exemplary cartridge may be configured to be inserted into a refillable pen injector 108 of FIG. 1A.

The environmental conditions of the drug 110 within the cartridge 550 may be maintained and controlled by the environmental control apparatus 140 formed in any suitable configuration, as described throughout the disclosure. In the embodiment of FIG. 13, the environmental control apparatus 140 may be formed as the tube 270 (FIG. 4) configured and sized for enclosing the cartridge 550. In the embodiment of FIG. 14, the environmental control apparatus 140 may be formed as the tube 278 (FIG. 5) configured and sized for enclosing the cartridge 550. In the embodiment of FIG. 15, the environmental control apparatus 140 may be formed as the tube 300 (FIG. 6) configured and sized for enclosing the cartridge 550.

Figure 16:
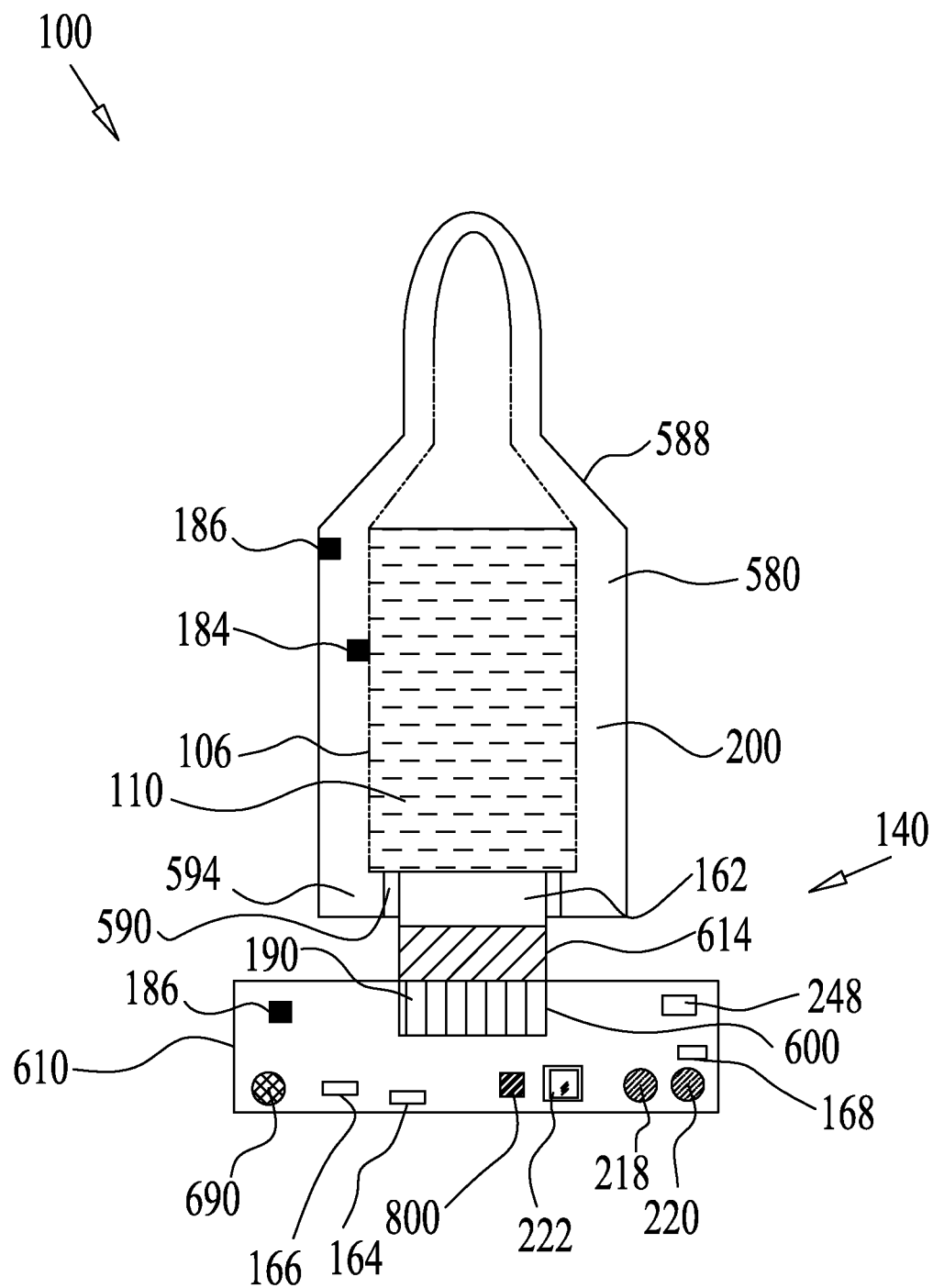
FIG. 16 is a schematic illustration of an exemplary substance control system according to some embodiments of the present disclosure.
Figure 17:
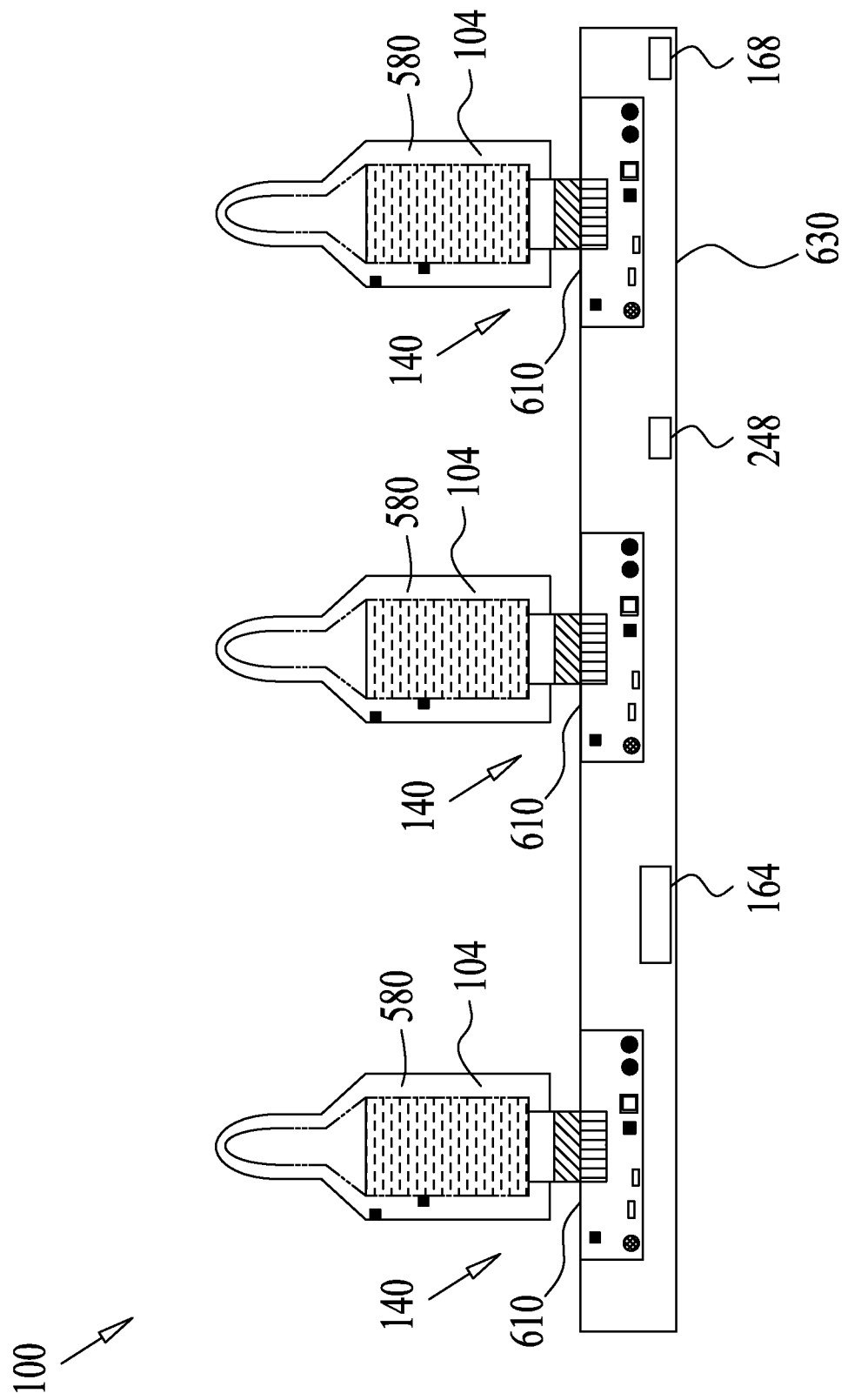
FIG. 17 is a schematic illustration of an exemplary substance control system according to some embodiments of the present disclosure.

FIGS. 16 and 17 illustrate an exemplary substance control system 100 according to some embodiments of the present disclosure. As seen in FIG. 16, the container 104 comprises a vial or ampule 580 including the chamber 106 containing a substance (e.g. the drug 110) therein. The ampule 580 comprises walls 588 formed of any suitable material for housing the chamber 106. Typically, the ampule 580 is configured as a disposable container.

In some embodiments, as seen in FIG. 16, the environmental control apparatus 140 comprises the ECM 162 including the TEC or any other active temperature controlling element. In some embodiments, the ECM 162 may comprise a metallic strip, for example. The walls 588 may be formed with thermal insulation 200, such as a thermal insulating material comprising glass, for example. The ECM 162 may be placed at any suitable location for thermal and/or mechanical contact with the chamber 106. As seen in FIG. 16, the ECM 162 is mounted within an aperture 590 formed within the wall 588, thereby excluding the thermal insulation 200 at the aperture 590 and allowing thermal contact between the ECM 162 and the chamber 106.

In the embodiment of FIG. 16 the ECM 162 is placed at a bottom portion 594 of the ampule wall 588, it being appreciated that the ECM 162 may be placed at the sides of wall 588.

The ECM 162 may be connected to a heat dissipater 190 comprising a heat sink element 600 placed at any suitable location, such as within a base 610. The ampule 580 may be mounted on base 610 and engaged therewith in any suitable manner such as by attachment means 614 which may be formed of a thermally conductive material as well as for attachment of the ECM 162 to the base 610, such as a magnet for example.

A power source, such as a battery 164 and the controller and electronics 166 may be embedded, or included in any suitable manner, within the base 610 as well as electrical communication between the battery 164 and the controller and electronics 166 and the ECM 162. Detectors 218, timers 220 and/or indicators 222 may be provided and placed on base 610.

At least one or more substance temperature sensors 184 may be provided in proximity to the chamber 106 and/or at least one or more ambient temperature sensors 186 may be provided in proximity to the ambient environment at any suitable location, such as on the wall 588 in proximity to the ambient environment, or on the base 610, for example.

The environmental control apparatus 140 may comprise communication means 248 for transmitting information therefrom to the device 250 and/or central database 252. The communication means 248 may be placed at any suitable location, such as within the base 610.

In some embodiments, the battery 164 may be rechargeable. Recharging may be performed via recharging port 168, or via inductance or other means which allow electrical charge generation. The recharging port 168 may be placed at any suitable location, such as within the base 610.

As seen in FIG. 16, the environmental control apparatus 140 comprises the ECS. The ECS includes the ECM 162 and base 610 which are configured for mechanically fitting the ampule 580.

In FIG. 16 a single ampule 580 and environmental control apparatus 140 are shown. Turning to FIG. 17, it is seen that the substance control system 100 may comprise an ampule holder or tray 630 for holding a plurality of ampules 580 therein. A plurality of environmental control apparatuses 140 including the ampules 580 and corresponding bases 610 may be mounted on the tray 630 or in some embodiments, the bases 610 may be embedded within the tray 630.

In some embodiments, the tray 630 may comprise a single recharging port 168 for recharging the battery 164 of the plurality of bases 610. In some embodiments, the tray 630 may comprise a single battery 164 used to provide power to each environmental control apparatus 140 and the tray 630 may further comprise electrical contacts with the ECM 162.

The active temperature controlling elements, such as the ECM 162 described in reference to FIGS. 1A-25, may be operated in any suitable manner. In some embodiments, the active temperature controlling element may operate substantially continuously during use of the environmental control apparatuses 140. In this continuous operational mode the ECM 162 is continuously operated to maintain the substance within the predetermined range (or below or above a predetermined threshold). The battery 164 or any other power source continuously operates as well, to provide power to the ECM 162 and the other electronics 166.

In some embodiments, the active temperature controlling element may operate selectively (i.e. a "thermostat" mode). In this selective operational mode the controller 166 may monitor the environmental condition (e.g. temperature) within the substance (e.g. drug 110) in a closed-loop circuit. Upon detection that the environmental condition deviated from the predetermined threshold or range, the ECM 162 is activated until the environmental condition returns to the predetermined threshold or range. Thereafter the ECM 162 may be deactivated until once again the environmental condition deviates from the predetermined threshold or range. During the selective operational mode the battery 164, or any other power source, can operate in response to the selective operation of the ECM, such that during time periods that the ECM 162 is inactive the electronics 166 may be inactive as well, or may operate with relatively low current. Thus this selective operational mode facilitates conservation of power. Yet, at time periods wherein the ECM 162 is inactive, heat may penetrate the chamber 106 via the ECM 162 and/or thermal transmitter 170, which is in thermal and/or mechanical contact with the ECM 162.

As seen in FIGS. 18A-19B, in order to prevent the heat penetration, a thermal switch 650 may be configured to selectively connect or disconnect the ECM 162 from chamber 106. The thermal switch 650 may comprise any suitable mechanism configured for selective contact in response to detection of deviation from the predetermined threshold or range. In some embodiments, as seen in FIGS. 18A-19B, the thermal switch 650 may comprise two adjacent first and second respective protrusions 654 and 658. The first protrusion 654 may extend from ECM 162 towards the second protrusion 658, which may extend from the thermal transmitter 170 or chamber 106. In the embodiment of FIGS. 18A and 18B, the first and second respective protrusions 654 and 658 may comprise magnetic properties. According to the direction of the electrical current of the electronics circuit, the protrusions 654 and 658 may be mutually attracted thereto. This attraction provides thermal contact between the ECM 162 and the thermal transmitter 170, upon activation of the ECM 162, as seen in FIG. 18A.

Whereupon the ECM 162 is inactive, the direction of the current may be directed to cause protrusions 654 and 658 to repel, thereby thermally disconnecting the ECM 162 from the thermal transmitter 170, as seen in FIG. 18B.

The protrusions 654 and 658 may be formed at least partially with magnetic properties or may comprise respective first and second magnetic strips 660 and 662 or other configurations. Any one of the first and second magnetic strips 660 and 662 may comprise a static magnet or an electromagnet paired with a corresponding electromagnet and/or the first and second magnetic strips 660 and 662 may comprise a ferromagnetic material.

Protrusions 654 and 658 may be configured of a flexible material allowing the protrusions 654 and 658 to contact each other upon attraction of the magnetic strips 660 and 662.

Turning to FIGS. 19A and 19B it is seen that the thermal switch 650 may comprise first and second respective protrusions 664 and 668 formed with an air gap 670 defined therebetween. On the first and/or second respective protrusions 664 and 668 there may be provided a suitable material that can expand and contract, such as a spring 680. Upon extension of the spring 680 the gap 670 fills, thereby connecting the ECM 162 to the thermal transmitter 170 or chamber 106, as seen in FIG. 19A. Upon contraction of the spring 680 the gap 670 vacates, thereby disconnecting the ECM 162 from the thermal transmitter 170 or chamber 106, as seen in FIG. 19B.

Further modes of operation and control of ECM 162 may be as follows: for example, in some embodiments, an electrical "gate", i.e., a transistor, is provided for supply of a current to an active temperature controlling element, such as a thermoelectric heat-pump, upon the temperature of the drug deviating from the predetermined threshold or range. Such a predetermined threshold or range may be established by the electrical parameters of the electrical circuit of electronics 166. This method may provide for a simple realization of a "gate" without a controller (which may be inexpensive and with lower power requirements). Any form of electrical circuit, analog or digital, may be used to control the power provided to the ECM 162 to effect a change in at least one environmental condition. Such circuits may utilize temperature sensors, such as sensors 184 and/or 186.

In some embodiments, the flow of power from the power source to the ECM 162 is determined based upon the temperature of the interior of the ECS sensed by the substance sensor 184.

In some embodiments, the ECM 162 may be configured to cool the drug 110 when the temperature inside the ECS is above the predetermined range to a temperature within the range. The ECM 162 may be further configured to heat the drug 110 when the temperature inside the ECS is below the predetermined range to a temperature within the predetermined range.

In some embodiments, the parameters of the electronic circuit may be chosen such that no current flows to the ECM 162 from the power source as long as the temperature of the of the substance within the chamber 106 is within the predetermined range or threshold. Whenever the temperature is out of this range or above or below the threshold, current is permitted to flow to cause the ECM 162 to effect a change in the temperature that is to increase or reduce the temperature until reaching the predetermined threshold or range, while the current provided to the ECM 162 is substantially reduced or shut off.

In any one of the environmental control apparatuses 140 described in reference to FIGS. 1A-25 comprising the active temperature controlling elements, such as the TEC, there may be provided an activation element 690 (FIG. 1A) to activate the ECM 162 upon detecting that the substance (e.g. drug 110) was inserted into the chamber 106. Thus, unnecessary use of the battery 164 is prevented.

In a non-limiting example, it was found that 0.33 W is sufficient power to activate the environmental control apparatus 140 comprising a tube similar to tube 240 of FIG. 2 for maintaining a substance of 3 cc of water at a required temperature of 8 C.°, while the environmental control apparatus 140 is placed at ambient temperature of 24 C.°. Accordingly, to operate the environmental control apparatus 140 for a period of 24 hours, the required energy will be: 0.33 W×3600 second×24 hours=28,512 Joules, which is less than the total energy provided by a standard 3.6-volt Lithium-ion battery, rated at 2,500 mAh as having a total energy of 32,400 Joules.

In some embodiments, any one of the environmental control apparatuses 140 described throughout the disclosure may comprise the controller 166 comprising a processor for controlling the ECM 162. The processor may include computer instructions comprising an algorithm operating thereon configured to control the ECM 162. In some embodiments, the algorithm may be configured to automatically control the temperature of the drug 110 contained within the DDSD, to be maintained within the predetermined range. In some embodiments, the algorithm may be configured to control the temperature while minimizing a thermal load created by the operation of the ECM 162.

Figure 20:
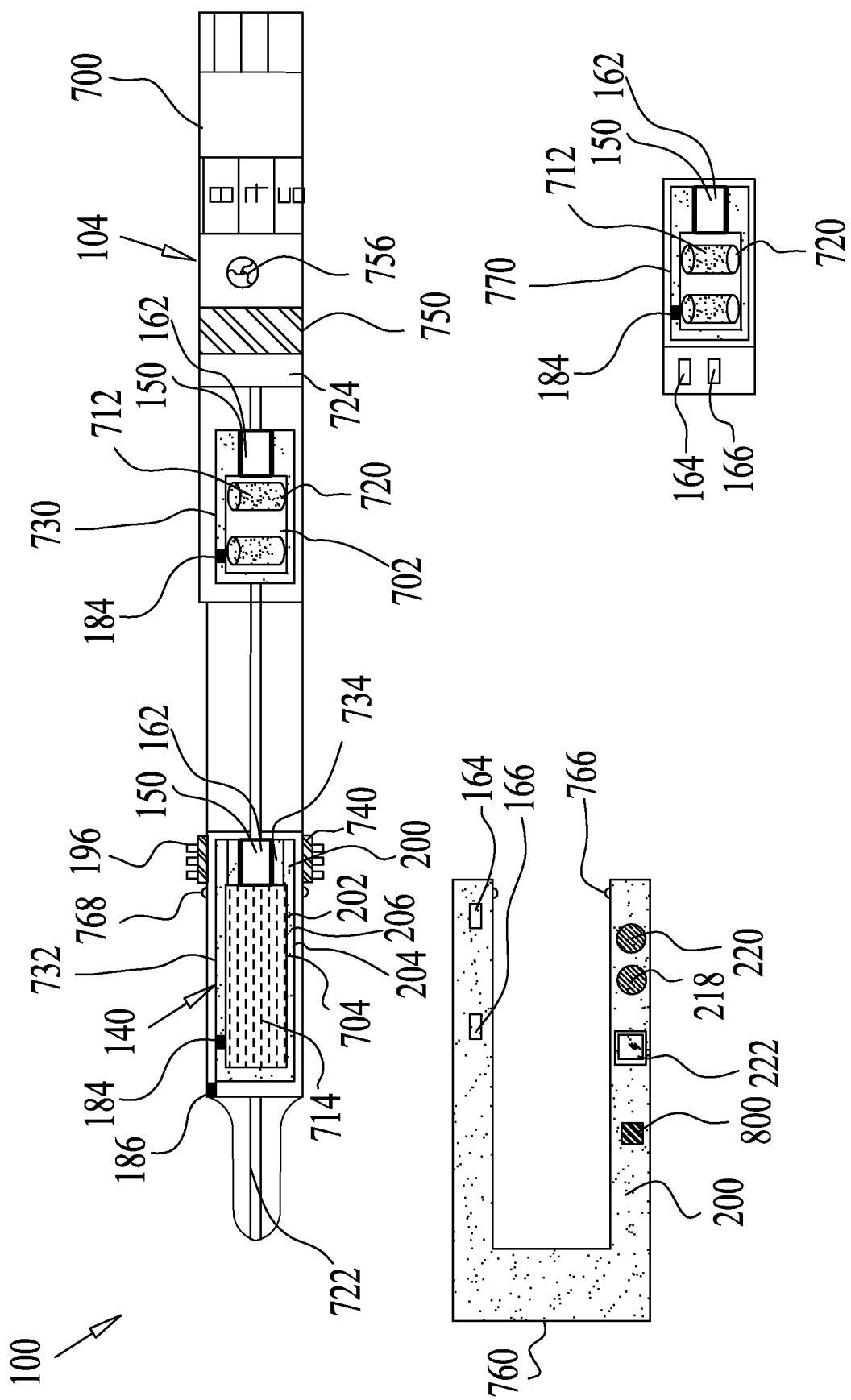
FIG. 20 is a schematic illustration of an exemplary substance control system according to some embodiments of the present disclosure.

FIG. 20 is a schematic illustration of an exemplary substance control system 100 according to some embodiments of the present disclosure. As seen in FIG. 20, the environmental control apparatus 140 may be configured to control and maintain the environmental condition of more than one substance and/or a substance at different phases. The container may comprise an injection pen 700 formed with at least two chambers 106 including a first storage chamber 702 and a second delivery chamber 704.

A first substance 712 may be contained in the first storage chamber 702 at a first phase and then, typically prior to delivery, or at any other suitable time, may be mixed with a second substance contained in the second delivery chamber 704. In a non-limiting example, the first substance 712 may comprise a drug 110 in powder form. The second substance 714 may comprise a mixing liquid or a mixing element for dissolving the powder when mixed therewith to provide a liquid drug preparation for delivery to a human or animal. In some embodiments, the second substance 714 may comprise a gas for gasifying the powder.

In a non-limiting example the drug 110 may be volatile when stored at a liquid phase. Therefore, the drug 110 may be first stored in a powder phase and prior to delivery, can be liquefied. Such a drug may include glucagon.

The first substance 712 and/or second substance 714 may be contained in a suitable receptacle, such as in plastic packets, for example. In some embodiments, the first substance 712 and/or second substance 714, when in powder form for example, may be encapsulated within a capsule 720. Capsule 720 may be formed of any suitable material. In some embodiments, the capsule 720 may be formed of a material with physical properties similar to aluminum, which does not interact or otherwise affect the drug 110. The capsule material may be formed of an opaque material for preventing penetration of light therein. The capsule 720 may also be formed of a heat conducting material such as, for example, a foil, and may be evacuated for air tight encapsulation and for preventing exposure to humidity.

In some embodiments, such as shown in FIG. 20, the capsules 720 may be stored within the first chamber 702 and the mixing liquid may be contained within the second chamber 704. The pen 700 may be prefilled with the capsules 720 and/or the mixing liquid, typically in a disposable pen.

In some embodiments, the pen 700 may be configured to receive the capsules 720 such as by providing an opening (not shown) to insert the capsules within the first chamber 702. The pen 700 may be additionally configured to receive the mixing liquid such as by providing an opening (not shown) to insert the mixing liquid within the second chamber 704, typically in a reusable pen. The capsules 720 may be pierced by a needle 722 of the injection pen and pushed by a plunger of a piston 724 into the second delivery chamber 704 to mix with the mixing liquid for dissolving the powder.

In some embodiments, the dissolved drug preparation may be introduced into an additional chamber (not shown) and may be delivered to the human or animal from the additional delivery chamber. Additional mixing of the powder and the mixing liquid and/or filtering may be performed within the additional chamber prior to delivery thereof.

In some embodiments, several drug capsules containing a drug in powdered form are placed within the first chamber 702. A single or a few capsules may be used at a particular time. A second capsule (or additional capsules) may be punctured and mixed with at least the mixing liquid whenever an additional dose of drug is required.

The injection pen 700 may be disposable or reusable. The environmental control apparatus 140 may be placed within the injection pen 700 around the first storage chamber 702 and/or the second delivery chamber 704, or in proximity thereto and may be configured to control and maintain the environmental conditions of the substance in the first storage chamber 702 and/or the second delivery chamber 704.

The environmental control apparatus 140 may comprise a first enclosure 730 enclosing the first chamber 702 and/or a second enclosure 732 enclosing the second chamber 704. The first enclosure 730 and/or second enclosure 732 (if provided) may include the ECM 162 comprising the TEC or any other active temperature controlling elements. The first enclosure 730 and/or second enclosure 732 may be formed of the thermal insulation 200. In some embodiments, the thermal insulation 200 may comprise the multi-layered material, formed of walls 202 and 204 with the evacuated gap 206 therebetween. The ECM 162 may be placed at any suitable location for thermal and/or mechanical contact with the first chamber 702. As seen in FIG. 20, the ECM 162 is mounted within an aperture 734 formed within the first enclosure 730 and/or second enclosure 732, thereby excluding the thermal insulation 200 at the aperture 734 and allowing thermal contact between the ECM 162 and the chamber 106.

At least one or more substance temperature sensors 184 may be provided in proximity to at least one of the first storage chamber 702 and/or the second delivery chamber 704 and/or at least one or more ambient temperature sensors 186 may be provided in proximity to the ambient environment at any suitable location, such as on the injection pen 700.

Heat may be dissipated by heat dissipater 190 forming at least a portion of a cover or ring 740 surrounding the pen injector 700. In some embodiments, heat dissipating fins 196 or any other heat dissipating element may be provided. In some embodiments, the heat dissipater 190 may comprise a heat sink element 750 placed within the pen injector 700. The heat may be removed from the ECM 162 via the piston 724 configured for thermal conduction for conducting heat to heat sink element 750. Additional methods for removing/adding heat from/to the first storage chamber 702 and/or the second delivery chamber 704 may be used, including, for example, micro-fans and/or heat sink elements. A micro-fan 756 may be placed within the pen 700.

In some embodiments, such as wherein all the first substance is directed from the first chamber 702 to the second chamber 704, the environmental control apparatus 140 may be configured to cease control by the ECM 162 of the first enclosure 730 and to activate the previously dormant ECM 162 of the second enclosure 732.

In embodiments wherein a portion of the first substance is directed from the first chamber 702 to the second chamber 704 and a portion remains within the first chamber 702, the environmental control apparatus 140 may be configured to continue control by ECM 162 of the first enclosure 730 and to activate the previously dormant ECM 162 of the second enclosure 732.

In some embodiments, the capsule 720 may be stored within an environmental control apparatus 140 external to the pen 700 and thereafter may be introduced into pen 700. Such an apparatus may be formed as an enclosure 770, similar to respective first or second enclosures 730 and 732 or as any one of the environmental control apparatuses 140 disclosed herein.

In some embodiments, the environmental condition in the first chamber 702 may be maintained at a different degree than the second chamber 704. For example, the temperature maintained within the first chamber 702 may be a storage temperature, which may be lower than the temperature maintained within the second chamber 704, maintained at a use temperature.

The battery 164 and the controller and electronics 166 may be embedded, or otherwise contained, within the first enclosure 730 or second enclosure 732 or within the injection pen 700, or within a cap 760 covering the injection pen 700, similar to the embodiment shown in FIG. 7. The cap 760 may comprise electrical contacts 766 for electronic communication with corresponding electrical contacts 768 of the first enclosure 730 and/or second enclosure 732. In some embodiments, the environmental control apparatus 140 and/or the pen 700 may comprise one or more detectors 218, timers 220 and/or indicators 222 placed in any suitable location, such as in the cap 760

In some embodiments, the environmental control apparatus 140 of any one of FIGS. 1A-25, may be configured to maintain the substance at different degrees of the environmental condition. In some embodiments, the substance (e.g. a drug 110) may be maintained at a first temperature or temperature range for a first time duration and thereafter maintained at a second temperature or temperature range for a second time duration. For example, the environmental control apparatus 140 may be configured to maintain the drug 110 at a storage temperature or range, wherein the drug 110 is in a storage state. Thereafter, prior to delivery of the drug, the drug temperature may be changed to a use temperature or range to bring the drug 110 to a use state thereof.

The indicator 222 may be configured to indicate to the user the current state of the drug 110, i.e. a storage state or use state.

The detection of use may be performed in any suitable manner, such as described in reference to FIG. 1A.

In some embodiments, a state switch 800 (FIG. 1A) may be provided and may be configured in any suitable configuration for effecting the shift from the storage temperature to the use temperature. In some embodiments, the shift may be reversible such that the temperature of the drug 110 may be shifted from use temperature back to storage temperature. In some embodiments, the environmental control apparatus 140 may be configured to affect the shift from the storage temperature to the use temperature and prevent reversal back to the previous storage temperature.

In some embodiments, the shift from the storage temperature to the use temperature may be performed manually by a user. In some embodiments, the shift from the storage temperature to the use temperature may be performed automatically upon detection of use by the detector 218. In some embodiments, the shift from the storage temperature to the use temperature may be based upon a predetermined program for setting the storage temperature range and the storage time span and the use temperature range and the use time span. The predetermined program may be governed by the controller 166.

In some embodiments, the ECS may be configured to control the environmental condition according to at least one of a first storage state configured to retain the drug 110 contained in the DDSD at the environmental condition within a first predetermined range, and a use state configured to retain the drug contained in the DDSD at the environmental condition within a second predetermined range. Prior to the first use of the DDSD, the environmental condition of the drug may be maintained at the storage state and after first use of the DDSD, the environmental condition of the drug may maintained at the use state. In some embodiments, the use state may be activated via the switch 800 or automatically upon the first use of the DDSD.

In a non-limiting example, the drug 110 may comprise insulin and may be delivered by an injection pen, such as injection pen 108 of FIG. 1A. The environmental control apparatus 140 may be configured to maintain the drug 110 at a storage temperature range of 2 C0 to 8 C.°, for a relatively long time span, such as a number of hours, days, months or even years. Thereafter, prior to delivery of the drug, the drug temperature may be changed to a use temperature in the range of 22 C.° to 24 C.° for a time span of minutes to a few hours.

In some embodiments, while in the storage state, activity of the controller and electronics 166 is reduced. Thus, unnecessary use of the battery 164 is prevented.

In some embodiments, a first environmental control apparatus 140 may be configured to maintain and control the substance at a storage state. Upon transition to a use state the container 104 may be removed from the first environmental control apparatus 140 and placed within a second environmental control apparatus 140, configured to maintain and control the substance at a use state.

Figure 21:
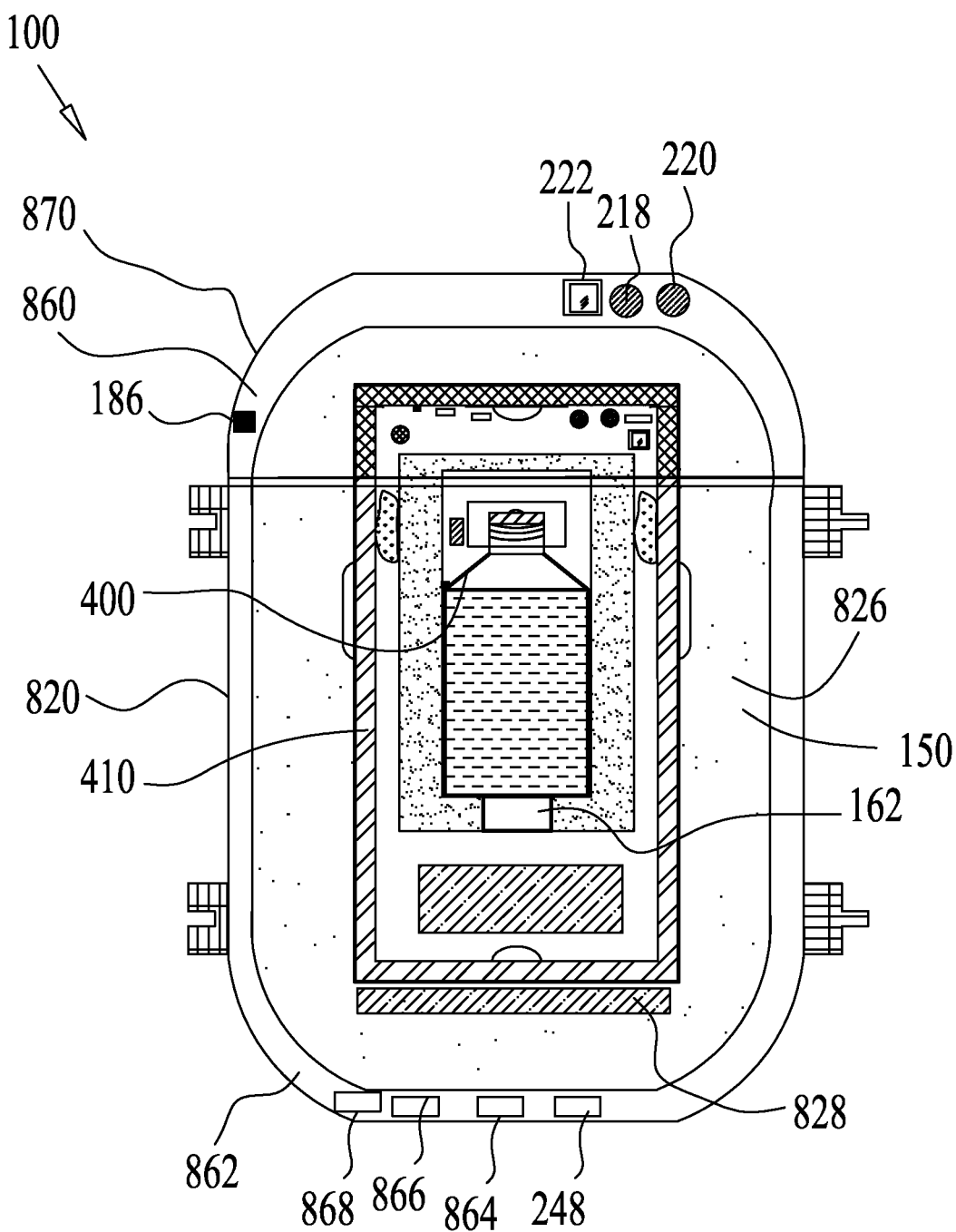
FIG. 21 is a schematic illustration of an exemplary substance control system according to some embodiments of the present disclosure.
Figure 22:
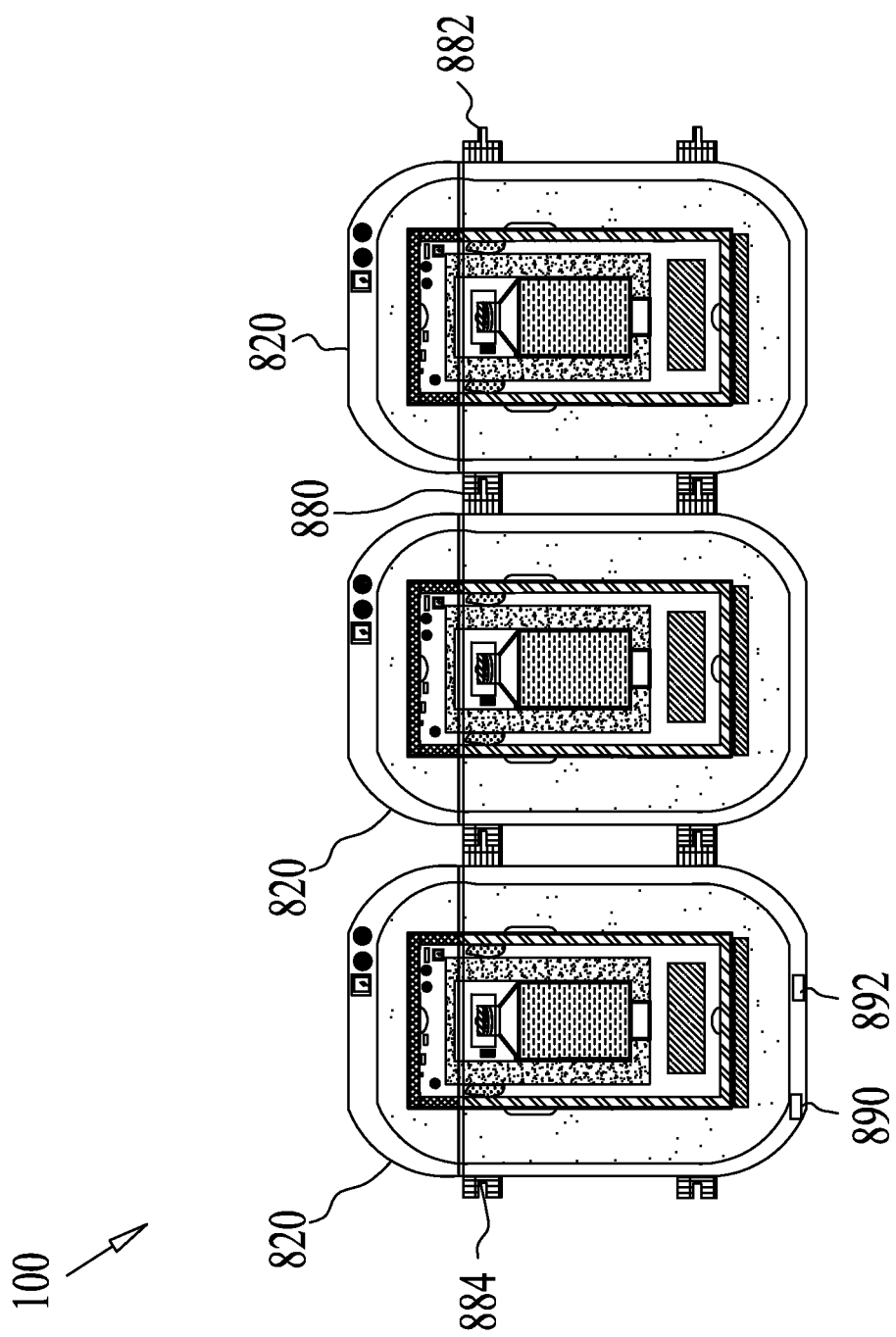
FIG. 22 is a schematic illustration of an exemplary substance control system according to some embodiments of the present disclosure.

FIGS. 21 and 22 are a schematic illustration of an exemplary substance control system 100 according to some embodiments of the present disclosure. As seen in FIG. 21, a casing 820 is provided for encasing the environmental control apparatus 140 and a container 104. In the embodiment of FIG. 21 the container 104 comprises the vial 400 and the environmental control apparatus 140 is formed of the tube 410 of FIG. 9, it being appreciated that the casing 820 may be used with any container 104 and environmental control apparatus 140.

The casing 820 may be formed as a carrying case, which may be transportable, and may be formed of a relatively small size for easy placement within a bag, handbag, backpack etc. The casing 820 may comprise the environmental control element 150, such as passive control elements, e.g. a material 826 formed of thermal insulation 200 configured in any suitable manner as described herein.

In some embodiments, the environmental control element 150 may additionally comprise an active control element, such as the ECM 162.

In some embodiments, the casing 820 may comprise a phase change layer 828 formed as layer 260 (FIG. 3) underlying at least partially a layer of the thermal insulation 826.

The container 104 may be encased in the casing 820 for a relatively long time period such as hours, days, weeks, months or years. In a non-limiting example, the substance within the container 104 may be maintained at a temperature which is significantly different than the ambient temperature outside the casing 820. In a non-limiting example, the drug can be maintained within the casing 820 at a temperature range of about 2 C.° to 8 C.°, while the ambient temperature can be around 25 C.° or the drug in the container 104 can be maintained at a temperature range of about 19 C.° to 25 C.° while the ambient temperature can be about minus 10 C.° to 50 C.°.

In some embodiments, the casing 820, encasing the container 104 and environmental control apparatus 140, may be placed in a refrigerator and may be used as a means of precaution in case the refrigerator is not powered, such as during a power out.

In some embodiments, the casing 820 may comprise at least one or more substance temperature sensors 184 provided in proximity to the chamber 106 or in thermal contact with the chamber 106. In some embodiments, the casing 820 may comprise at least one or more ambient temperature sensors 186 placed in proximity to the ambient environment at any suitable location, such as on a cover 860 of the casing 820.

The environmental control apparatus 140 may comprise communication means 248 for transmitting information therefrom to the device 250 and/or central database 252. The communication means 248 may be placed in any suitable location, such as at a base portion 862 of casing 820. The communication means may comprise a port and/or transceiver, such as a wireless transceiver or a wired transceiver.

A power source, such as a battery 864 (comprising battery 164 of FIG. 9) and the controller and electronics 866 (comprising controller and electronics 166 of FIG. 9) may be embedded within base portion 862, or included in any suitable manner, within the casing 820. There also may be included electrical communication between the battery 864 and the controller and electronics 866. In some embodiments, the battery 864 may provide power to the ECM 162 and controller and electronics 166 within the environmental control apparatus 140. The battery 864 may be provided in addition to battery 164 as a supplementary power source or the battery 864 may replace battery 164.

In some embodiments, the battery 864 may be rechargeable. Recharging may be performed via a recharging port 868, or via inductance or other means which allow electrical charge generation. The recharging port 868 may be placed at any suitable location, such as in base portion 862.

Heat may be dissipated by heat dissipater 190 forming at least a portion of the cover 860, which may be formed with a smooth surface or a surface configured with formations thereon (so as to function as a heat sink). Additional methods for removing heat from the ECM 162 may be used, including, for example, micro-fans and/or heat sink elements.

The casing 820 may be formed with a lid 870 for allowing insertion of the environmental control apparatus 140 and the container 104 therein and removal therefrom. The casing 820 may be air-tight.

The casing 820 may comprise one or more detectors 218, timers 220 and/or indicators 222.

In FIG. 21 a single casing 820 and environmental control apparatus 140 are shown. Turning to FIG. 22, it is seen that a plurality of casings 820 may be coupled to each other by any suitable means. In some embodiments, the casing 820 may be formed with attachment means 880 mounted on the cover 860. The attachment means 880 may comprise a protrusion 882 configured to mate with a recess 884 formed in a corresponding attachment means of an adjacent casing 820. In some embodiments, the attachment means may include an electrical attachment and/or a magnetic attachment or any other suitable configuration.

In some embodiments, the casing 820 may be configured to be stackable with additional casings 820.

The coupling of a plurality of casings 820 allows for portability of the plurality of containers 104 while maintaining the substance therein under the predetermined environmental conditions. In some embodiments, charging the power sources, e.g. the batteries 164 of the plurality of environmental control elements 140, may be facilitated simultaneously by a single or a few recharging means. In some embodiments, the recharging may be performed by a recharging port 890 configured to simultaneously recharge the power sources of the plurality of environmental control elements 140 and/or the plurality of casings 820. In some embodiments, the charging may be performed in any suitable manner, such as by wired electrical connections, by wireless connections such as by induction charging or any suitable manner.

In some embodiments, a single or a few power sources, e.g. a battery 892, may be provided to power the plurality of environmental control elements 140 and/or the plurality of casings 820.

Figure 23:
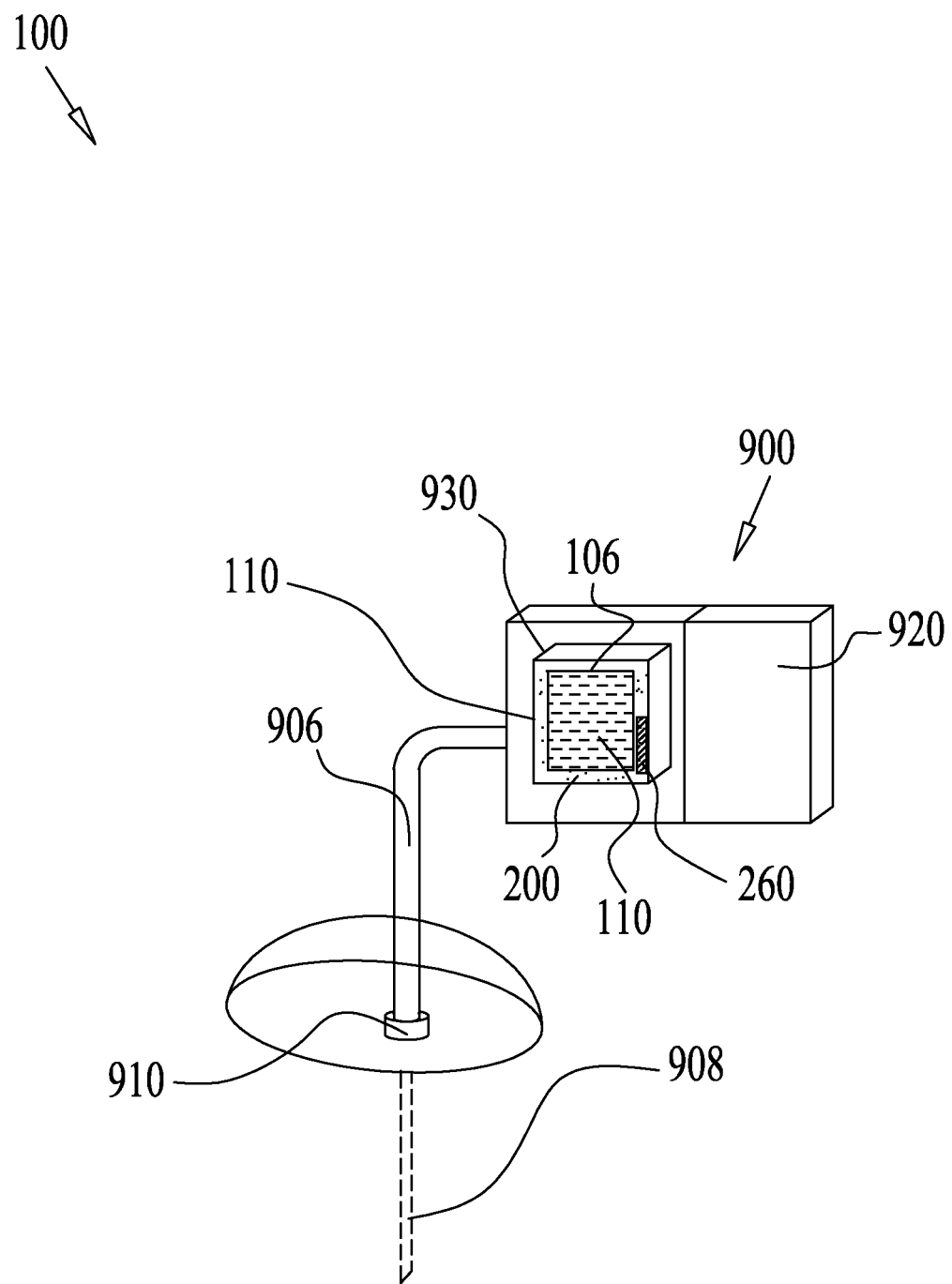
FIG. 23 is a schematic illustration of an exemplary substance control system according to some embodiments of the present disclosure.

FIG. 23 is a schematic illustration of an exemplary substance control system 100 according to some embodiments of the present disclosure. As seen in FIG. 23, the substance, comprising a drug 110, may be delivered by infusion. A drug infusion device 900 comprises a catheter 906 formed, on one end thereof, with a cannula 908, which can be inserted into a human or animal tissue. In some embodiments, a connector 910 can connect the catheter 906 to the tissue. Catheter 906 can be connected to the drug chamber 106 and to an infusion pump 920, provided for control of the drug delivery from the chamber 106.

In some embodiments, an environmental control apparatus 140 may be provided. As seen in FIG. 23, the environmental control apparatus 140 may comprise an enclosure 930, configured substantially as the enclosure 396 of FIG. 8. The enclosure 930 comprises the environmental control element 150 including any passive control element, such as the layer of thermal insulation 200 for shielding the chamber 106 from the ambient environmental conditions. The phase change material layer 260 may be provided and, at least partially, underlie the thermal insulation 200.

In some embodiments, the environmental control element 150 may comprise active control elements (e.g. ECM 162) and the enclosure 930 and/or the drug infusion device 900 may include a power source and the controller and electronics, as described herein in reference to the enclosure 356 of FIG. 7.

In some embodiments the drug infusion device 900 may comprise at least two chambers (not shown), where at least a first chamber contains the drug 110 in liquid form, while the second or more chambers, can contain a liquid, another drug, or liquid to be mixed with a drug powder. For example, one drug may be insulin while the other may be glucagon. The enclosure 930 may enclose the first chamber and/or second chamber for controlling and maintaining the environmental condition therein.

In some embodiments, the drug infusion device 900 may comprise a tubeless or patch pump like the OmniPod of InsuLet or a tubed pump such as the Medtronic Minimed Paradigm insulin pump.

In some embodiments, various components of the drug infusion device 900, such as one or more of the catheter 906, and pump 920, may be thermally insulated by the thermal insulation 200 described herein.

Figure 24:
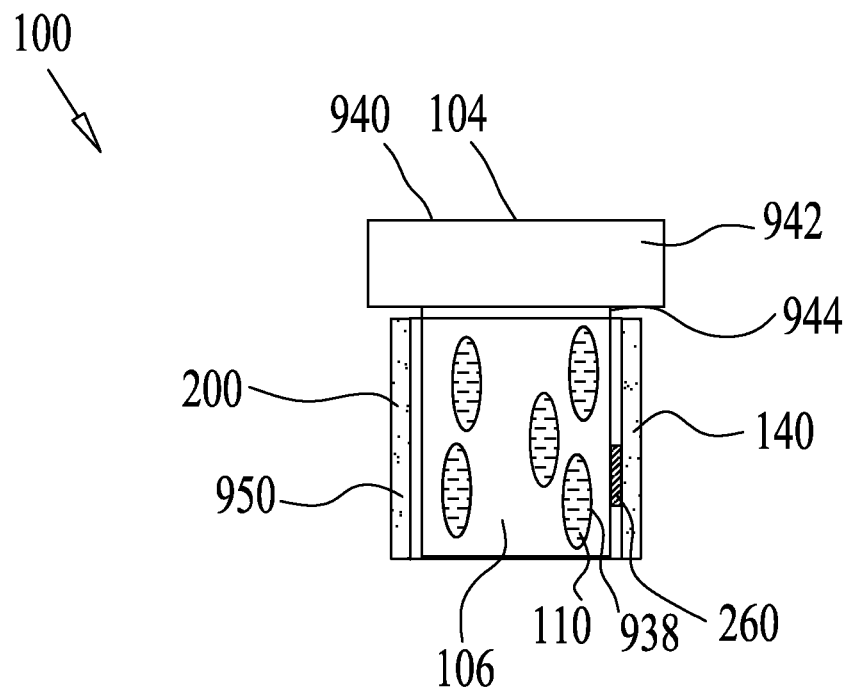
FIG. 24 is a schematic illustration of an exemplary substance control system according to some embodiments of the present disclosure.

FIG. 24 is a schematic illustration of an exemplary substance control system 100 according to some embodiments of the present disclosure. As seen in FIG. 24, the substance may comprise a drug 110 formed as pills 938 and the container 104 may comprise a standard pill dispenser 940, such as a tube or bottle, provided with a lid 942 and an opening 944. The chamber 106 may comprise the volume of the pill dispenser 940. In some embodiments, the environmental control apparatus 140 may be formed as a ring 950 configured to be slipped on the pill dispenser 940.

The ring 950 may comprise the environmental control element 150 including any passive control element, such as the layer of thermal insulation 200 for shielding the chamber 106 from the ambient environmental conditions. The phase change material layer 260 may be provided and, at least partially, underlie the thermal insulation 200.

In some embodiments, the environmental control element 150 may comprise active control elements (e.g. ECM 162) and the ring 950 and/or the pill dispenser 940 may include a power source and the controller and electronics, as described herein in reference to the enclosure 356 of FIG. 7.

In some embodiments, various components of the pill dispenser 940, such as the lid 942, may be thermally insulated by the thermal insulation 200 described herein.

Figure 25:
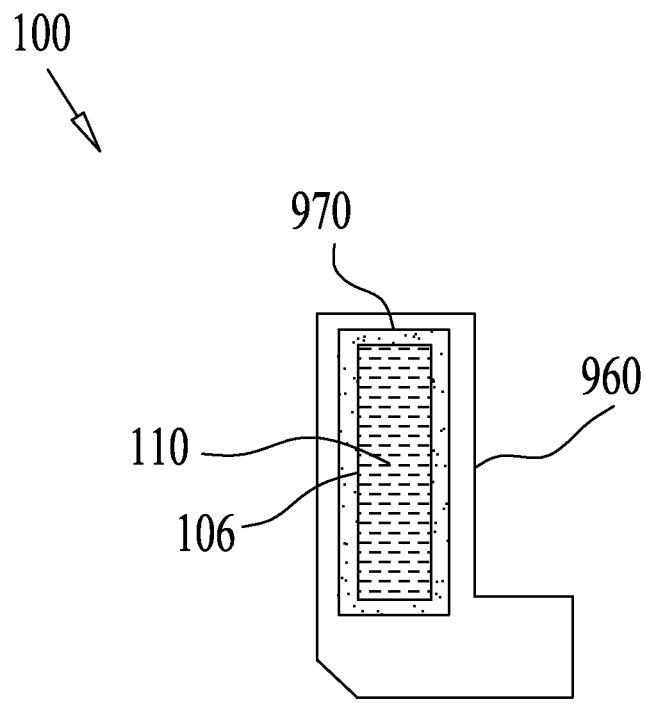
FIG. 25 is a schematic illustration of an exemplary substance control system according to some embodiments of the present disclosure.

FIG. 25 is a schematic illustration of an exemplary substance control system 100 according to some embodiments of the present disclosure. As seen in FIG. 25, the substance may comprise a drug 110 formed as a fluid or powder and the container 104 may comprise an inhalator 960. The inhalator 960 may comprise a drug chamber 106, which typically contains a pressurized drug.

In some embodiments, the inhalator 960 comprises a dispensing assembly configured to remove the drug from the chamber 106, generally upon pressing the chamber 106. The drug is delivered via an opening formed in the chamber 106 to an orifice (e.g. the mouth) of a user.

In some embodiments, an environmental control apparatus 140 may be provided. As seen in FIG. 25, the environmental control apparatus 140 may comprise an enclosure 970, configured substantially as the enclosure 396 of FIG. 8. The enclosure 970 comprises the environmental control element 150 including any passive control element, such as the layer of thermal insulation 200 for shielding the chamber 106 from the ambient environmental conditions. The phase change material layer 260 may be provided and, at least partially, underlie the thermal insulation 200.

In some embodiments, the environmental control element 150 may comprise active control elements (e.g. ECM 162) and the enclosure 970 and/or the drug inhalator 960 may include a power source and the controller and electronics, as described herein in reference to the enclosure 356 of FIG. 7.

In some embodiments, any one of the environmental control apparatuses 140 described in reference to FIGS. 1A-25 may include the dispensing assembly comprising an opening configured for allowing removal of the drug 110 from the chamber 106 and delivering thereof to the patient via an orifice provided with the patient (e.g. the user).

In some embodiments, any one of the environmental control apparatuses 140 described in reference to FIGS. 1A-25 may comprise means for controlling the environmental conditions of a substance. In some embodiments, a predetermined humidity threshold or range may be maintained and controlled, using any one of the environmental control elements 150 described herein in reference to temperature control. In some embodiments, the environmental control element 150 may comprise O-rings, sealants or any humidity absorbing element for maintaining and controlling the humidity of a substance.

In some embodiments, a predetermined pressure threshold or range may be maintained and controlled using an environmental control element 150 comprising a valve, insulation, O-rings or any element configured to prevent ambient pressure from entering the chamber 106.

In some embodiments, a predetermined light absorption threshold or range may be maintained and controlled using an environmental control element 150 comprising an opaque cover or any material configured for preventing light from penetrating the chamber 106.

In some embodiments, any one of the environmental control apparatuses described in reference to FIGS. 1A-25 may exclude the environmental control element 150 and may just include any one of the features described herein (e.g. detectors 218, timers 220 and/or indicators 222)

There are provided according to some embodiments of the present disclosure, systems and methods for calculating a quantity of the substance within the container 104 prior to or after delivery of the substance. The quantity may be measured in any suitable manner, such as the mass, weight, volume or units of the substance, for example.

According to one method, the quantity of the substance may be calculated by measurement of temperature changes, or other parameters related to the temperature change, within the substance over a predetermined time span. In some embodiments, the measurement of the temperature changes or the other parameters, may be performed using any one of the environmental control apparatuses 140 described in reference to FIGS. 1A-25.

In other words, the reading from the ambient temperature sensor 184 (such as from the interior of the ECS) and the reading from the ambient temperature sensor 186 may be used to determine the quantity of drug in the DDSD and the quantity of drug removed from the DDSD.

For example, the quantity calculating system for calculating the substance quantity may include a clock, counter or timer 220 (FIG. 1A) configured to record the passage of time span "t" (i.e. duration) during a predetermined temperature change "$\Delta T$" (e.g. heating and/or cooling) of the substance. The quantity calculating system may additionally comprise the substance temperature sensor 184 (FIG. 1A) for measuring the temperature changes within the substance and the ambient temperature sensor 186 for measuring the ambient temperature.

The initial quantity of the substance contained in the container 104 may be known, such as the weight, denoted by "$m_1$". The ambient temperature sensor 186 may be used to measure the initial ambient temperature "$T_{ai}$" while the initial time "$t_i$" is recorded. At the same time, at $t_i$, the substance temperature sensor 184 may measure the initial substance temperature "$T_{si}$".

These measurements may be repeated and recorded until the substance temperature changes by $\Delta T$. In other words, these measurements may be repeated until the current measured substance temperature, $T_s(t)$, has changed from the initial substance temperature, $T_{si}$, by $\Delta T$, such that at a final time "$t_f$" it is established that $T_s(t) - T_{si} = \Delta T$.

In some embodiments, to ensure the ambient temperature is substantially stable and constant during the repeated substance temperature measurement, the ambient temperature is measured and compared to the initial ambient temperature, $T_{ai}$. Whereupon the current ambient temperature $T_a(t)$ is identical or substantially similar to the initial ambient temperature $T_{ai}$ (with some allowed deviation) the respective data generated by the substance measurement $T_s(t)$, $T_{si}$, $\Delta T$, $t_i$ and $t_f$, will be recorded and utilized.

From these time recordings a first time span t, denoted by $t_1$, is found that: $t_1 = t_f - t_i$ which is the time it takes for the substance under constant heat flux to achieve the predetermined temperature change, $\Delta T$ at a first time span.

The substance temperature and ambient temperature measurements may be repeated and the time $t_1$ can further be averaged or recorded for different substantially constant ambient temperatures. The result may be a table or any other form demonstrating an empirical relationship between the time duration, t, it takes to achieve the predetermined substance temperature change, $\Delta T$, at a constant ambient temperature, and a series of constant ambient temperatures.

Following a change in the substance quantity, the measurements may be repeated as described hereinabove and a second time span $t_2$, wherein $t_2 = t_f - t_i$ is recorded at a respective constant ambient temperature.

In some embodiments, the recorded times $t_1$ and $t_2$ and the corresponding temperature measurements (e.g. $T_s(t)$, $T_{si}$, $\Delta T$) may be utilized to calculate the substance quantity in any suitable manner. In some embodiments, the averages of $t_1$ and $t_2$ may be calculated and the corresponding temperature measurements may be utilized for calculating the substance quantity, according to the following non-limiting exemplary algorithm or in any other suitable manner:

The amount of energy "Q" required to change the temperature of a substance by the predetermined temperature change $\Delta T$ is generally calculated by:

$$Q = mC_p \Delta T \qquad \text{Formula 1:}$$

Where m is the substance weight and $C_p$ is the substance specific heat capacity (specific heat).

Since it is established that: Q[joules]=Φ[watts]×t[sec]

The time for a substance to change its temperature by $\Delta T$ under constant heat flux Φ may be calculated by $$t = mC_p \Delta T / \Phi \qquad \text{Formula 2:}$$

Hence, a change in the substance weight, while the other parameters are constant, will result in a change of time span t it takes to achieve the same change in temperature $\Delta T$.

Whereupon the substance weight is reduced, which occurs following use of the substance, it will take a shorter time span t to achieve the specific temperature change $\Delta T$. The time span t can be found from $$t_1 = m_1 C_p \Delta T / \Phi, \; t_2 = m_2 C_p \Delta T / \Phi$$

since $t_2$ is shorter than $t_1$ it satisfies $t_2 = t_1 - \Delta t$ therefore $\Delta t$ can be expressed as:

$$\Delta t = t_1 - t_2 = (m_1 - m_2) C_p \Delta T / \Phi = \Delta m C_p \Delta T / \Phi$$

The ratio $t_2/t_1$ it is then:

$$t_2/t_1 = (t_1 - \Delta t)/t_1 = 1 - \Delta t/t_1 = 1 - ((\Delta m C_p \Delta T/\Phi) \times (\Phi/m_1 C_p \Delta T)) = 1 - \Delta m/m_1$$

from this: $\Delta m/m_1 = 1 - (t_2/t_1)$ or $$\Delta m = m_1(1 - (t_2/t_1)) = m_1((t_1 - t_2)/t_1)$$

Or finally $$\Delta m = m1 \frac{\Delta t}{t1},$$

where $\Delta t = t_1 - t_2$

Thus, the change in the substance quantity, such as the weight change $\Delta m$, may be calculated based on the initial quantity, such as the initial weight $m_1$, and temperature measurements at that time. The substance quantity may further be calculated based on the time span t, it takes to achieve the predetermined change in temperature $\Delta T$, during the initial substance quantity at time span $t_1$ and during a reduced substance quantity at time span $t_2$. This substance quantity calculation may be performed without prior calibration, yet wherein the heat flux can be considered to be constant during the temperature measurements.

In some embodiments, the substance quantity may be calculated according to the above algorithm wherein the net heat flux in the environmental control apparatus 140 can modify the substance temperature by the required temperature change $\Delta T$ within a finite time. Therefore a condition for the measurement may include:

$$|Ta - Ts| > \Delta T$$

Where Ta is the ambient temperature and Ts is the substance temperature. This condition may be fulfilled wherein the heat flux is constant during the time span t that it takes for the substance temperature to be modified by $\Delta T$. This same constant heat flux may occur also during the substance temperature change by $\Delta T$. This generally occurs since users may use the substance while there is no immediate change in the ambient temperatures. In practical terms, the time to achieve the $\Delta T$ change in the substance temperature, should be longer than the activation time of an active control element (e.g. the ECM 162) which is used to shift the substance temperature back from the current substance temperature $T_s(t)$ to the initial temperature $T_{si}$.

In some embodiments, the constancy of the heat flux Φ may be affected by the thermal insulation 200 of the container 104, by the ambient temperature and by the setting point (e.g. the initial substance temperature $T_{si}$) for activation.

The following is a non-limiting example of the algorithm described above. The results are shown in the graph of FIG. 26.

Figure 26:
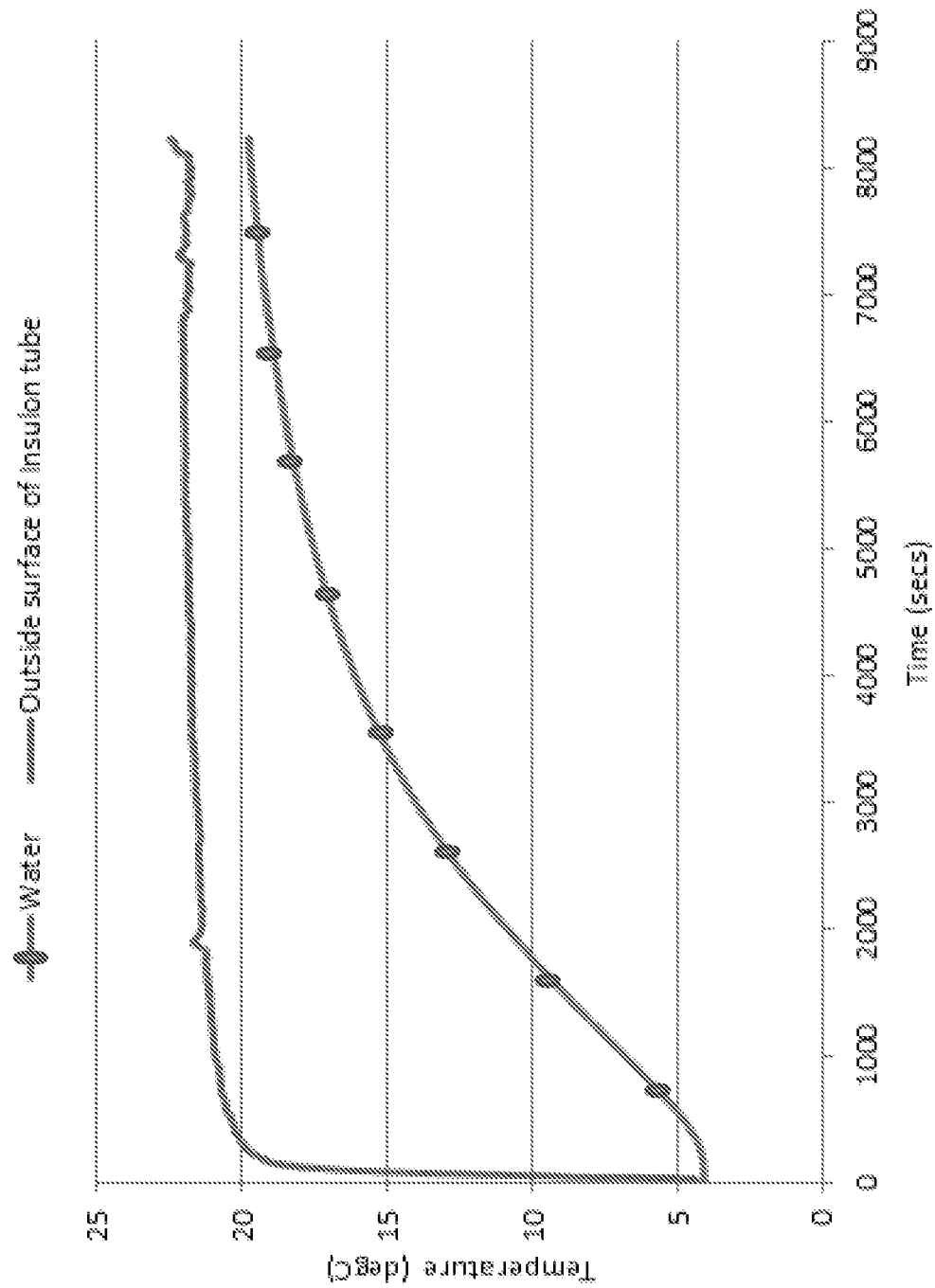
FIG. 26 is an exemplary graph showing the time span t it takes to effect a temperature change ΔT of water within the substance control system.

FIG. 26 is an exemplary graph showing the time t (in seconds) it takes for a temperature change ΔT of water, measured in IU volume, to shift by 3 C.°, assuming a drug reacts similarly to water. A volume of 3 cc of water (equaling 300 IU of insulin) was placed within a chamber 106. The container 104 was a syringe controlled by an environmental control apparatuses 140 configured generally as shown in FIG. 4, wherein the thermal insulation 200 comprises walls 202 and 204 formed of INSULON® and an evacuated gap 206 therebetween of about 0.6 millimeters The environmental control apparatus 140 was removed from refrigeration wherein the initial water temperature $T_{si}$ was about 4 C.° and was placed in an ambient environment with a temperature of about 22 C.°. Thus, the difference between the ambient environment temperature and the substance temperature ($T_a - T_s$) was about 18 C.°. It was found that a time span of 1074 seconds passed (t=1074) to shift the temperature ΔT by 3 C.°, i.e. from 4 C.° to about 7 C.°. The water temperature was measured by the temperature sensor 184 and the measured water temperature is depicted by the dotted line.

FIG. 26 additionally shows the temperature detected by the ambient sensor 186 placed in proximity to cover 190. The measured ambient temperature is depicted by the smooth line. It is seen that the ambient temperature changed almost instantly, while a time span of 1074 seconds passed within the water to shift the water temperature by 3 C.°. This is due to thermal insulation 200, the water heat capacity and volume.

Figure 27:
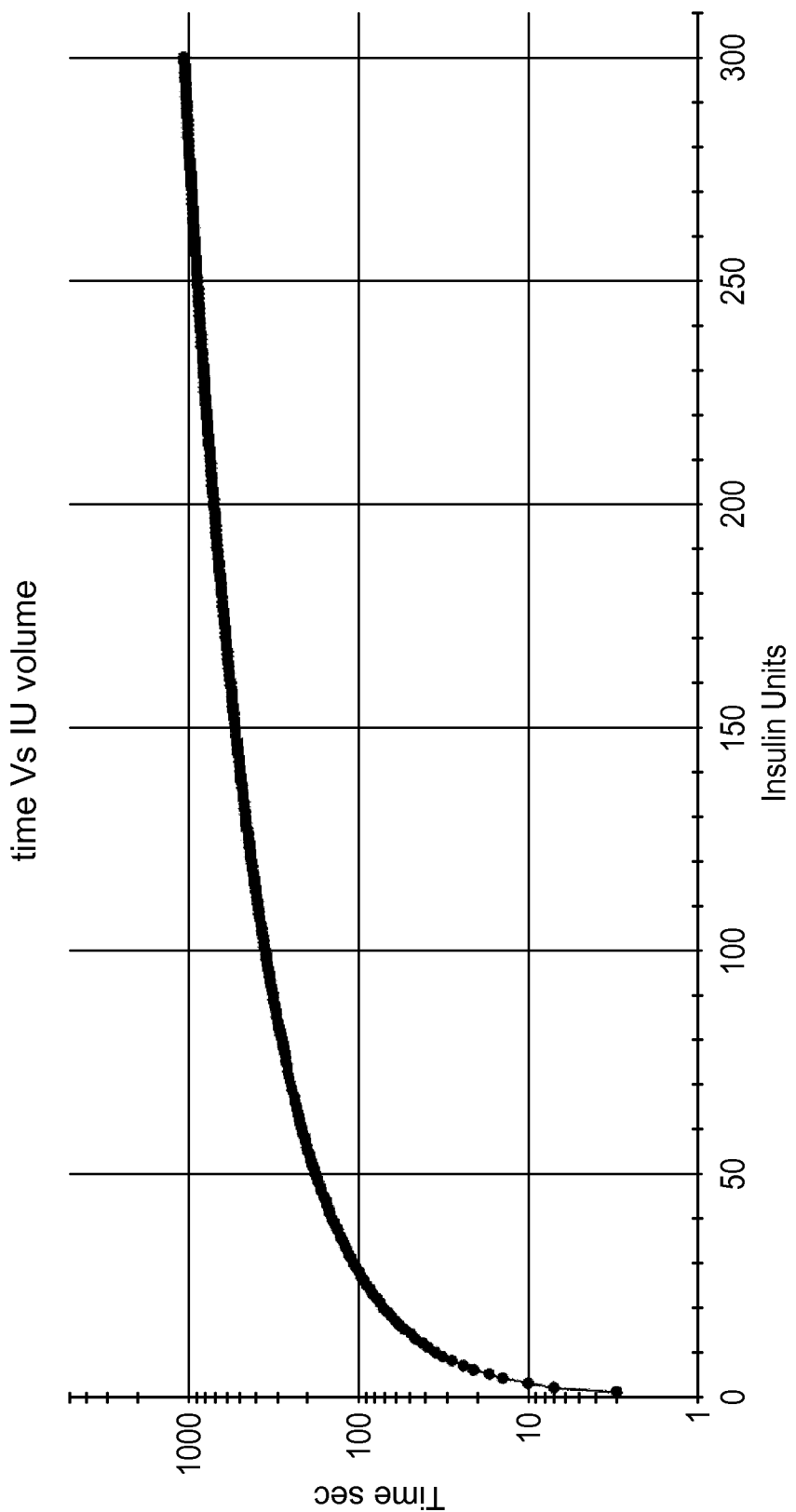
FIG. 27 is an exemplary graph showing the time t Vs. the calculated quantity of the water shown in the example of FIG. 26.

FIG. 27 is an exemplary graph depicting the relationship of t Vs. the calculated quantity of the water shown in the example of FIG. 26. In this example, the quantity comprises a volume and is measured in insulin units (IU). It is seen that at about 1074 seconds the water quantity is about 300 IU.

Figure 28:
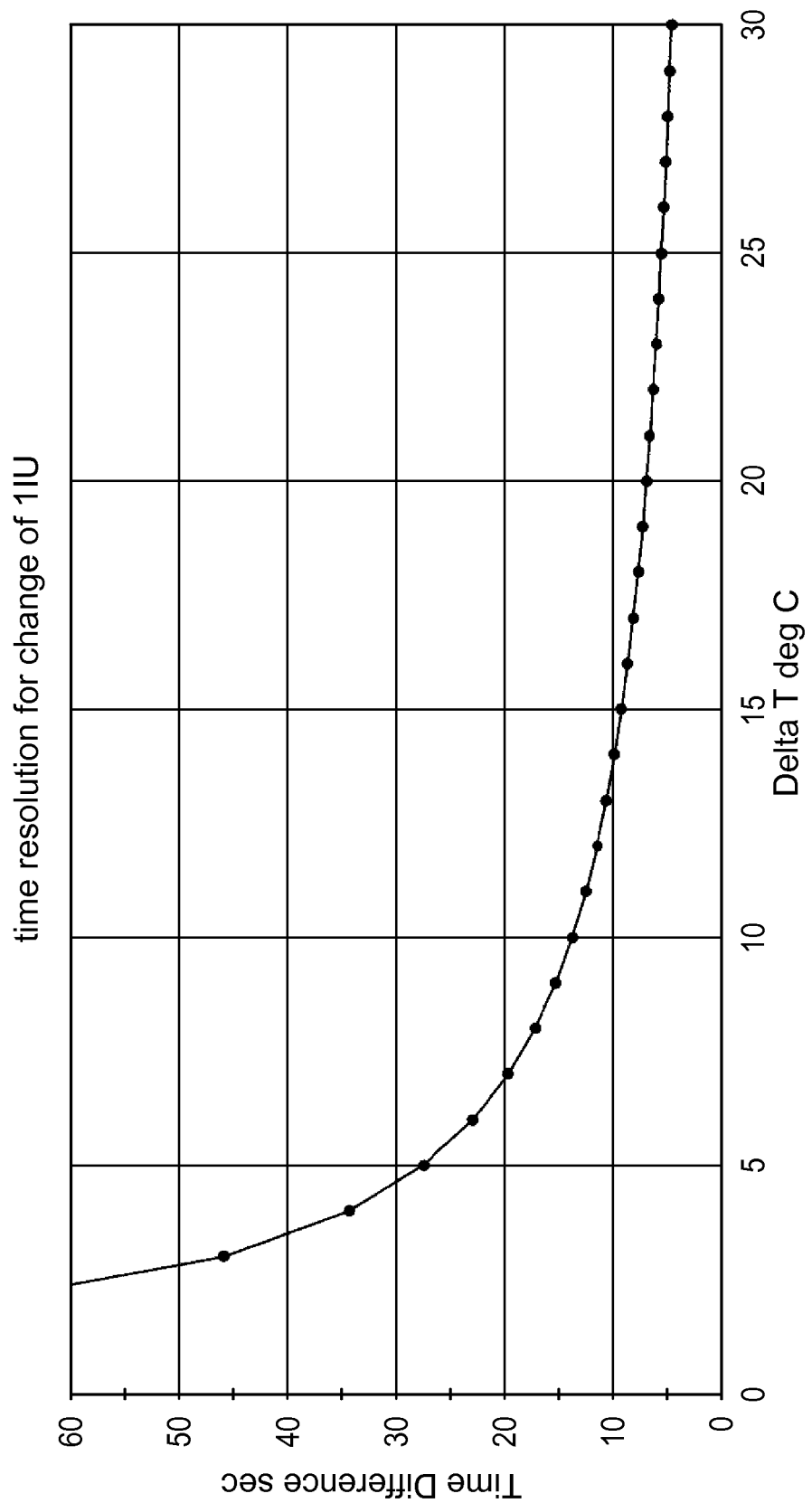
FIG. 28 is an exemplary graph depicting the time t Vs. changes in temperature ΔT, per 1 unit of Insulin as measured in the substance control system.

An exemplary graph depicting this relationship of the time span t Vs. ΔT is shown in FIG. 28 for a drug volume of 1 unit (IU) of Insulin, which is 0.01 milliliters. It can be seen that even for such a small substance quantity, the time at each different temperature of the substance is measurable with relatively high precision.

To enhance accuracy of the measured time, t Vs. changes in temperature, ΔT, the measurements may be performed repeatedly at various times and conditions of use, such as prior to use of the substance or after use of a portion of the substance, at various ambient environment temperatures, for example. The repeated measurements may be recorded and processed to generate an accurate calculation of the substance quantity.

Figure 29:
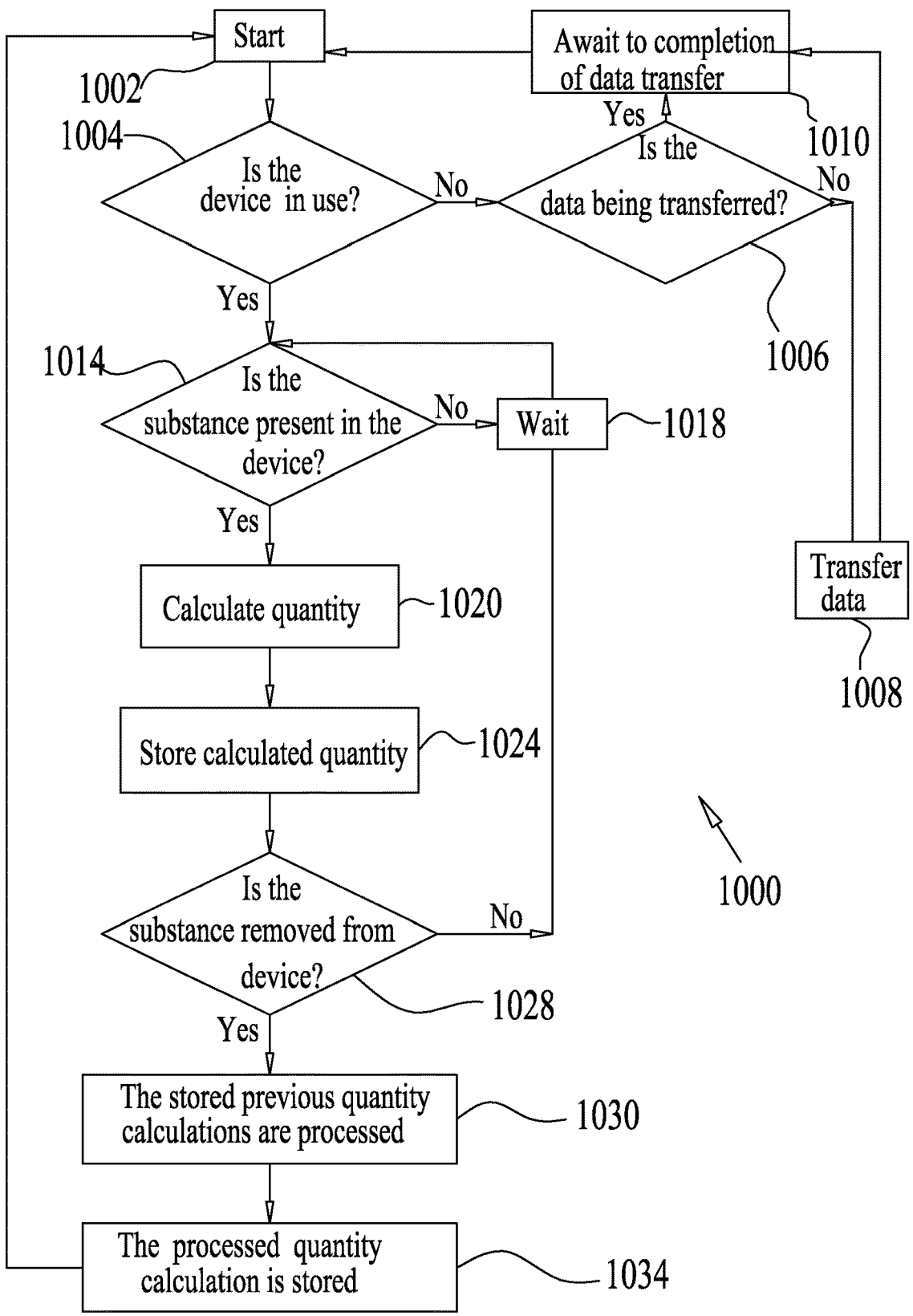
FIG. 29 is an exemplary flowchart illustrating a general process for executing an algorithm for repeated calculations of the substance quantity and processing thereof.
Figure 30:
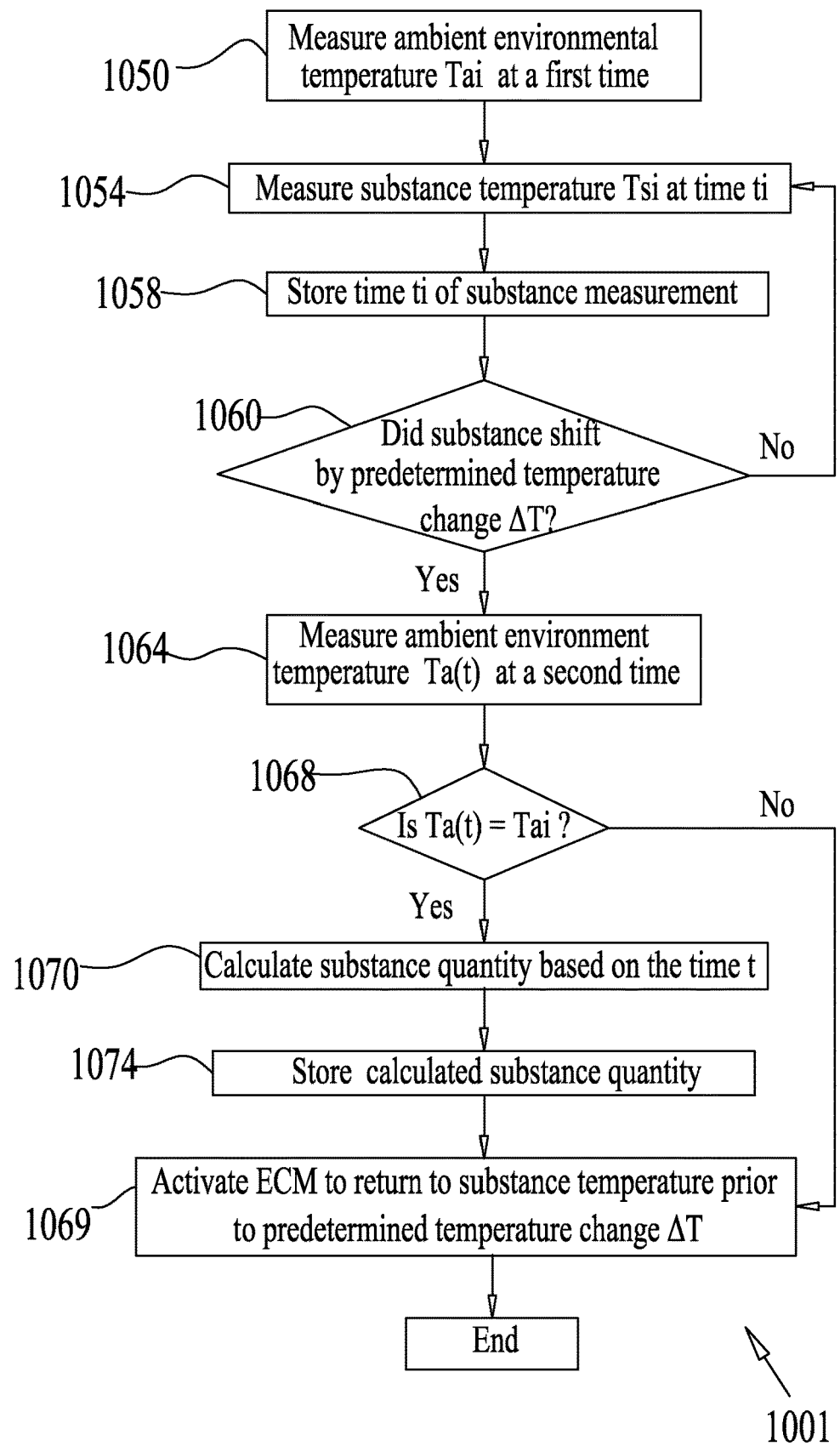
FIG. 30 an exemplary flowchart illustrating a process for executing an algorithm for a single or few calculations of the substance quantity.

FIGS. 29 and 30 are an exemplary flowchart showing a process of an algorithm for performing the repeated measurements of temperature and time to generate an accurate calculation of the substance quantity. FIG. 29 illustrates a general process 1000 for executing an algorithm for repeated calculations of the substance quantity and processing thereof and FIG. 30 illustrates a process 1001 for executing an algorithm for a single or few calculations of the substance quantity.

As seen in FIG. 29, following initiation of the algorithm at step 1002 it is verified at step 1004 whether the environmental control apparatus 140 (i.e. "device") is in use or docked or being recharged. If the environmental control apparatus 140 is docked, at step 1006 it is checked whether data is being transferred, such as to device 250 (FIG. 2) and/or central database 252. The data is transferred at step 1008 until completion at step 1010.

If at step 1004 the environmental control apparatus 140 is in use, it is thereafter verified whether the container 104 is present in the environmental control apparatus 140, as seen at step 1014, allowing a waiting period at step 1018 until the container 104 is placed within the environmental control apparatus 140. If the container 104 is placed within the environmental control apparatus 140 a single quantity of the substance is calculated at step 1020 as further described in reference to FIG. 30. Upon calculation of a single quantity the calculation is stored in any suitable memory device at step 1024.

If the container 104 is still maintained within the environmental control apparatus 140 the waiting period at step 1018 may be completed and the steps for calculating the substance quantity are repeated until the container 104 is removed from the environmental control apparatus 140. Once the container 104 is detected as being removed at step 1028, the previous calculations stored at step 1024 may be processed for obtaining an accurate quantity measurement at step 1030. The processing may include averaging the previous calculations, removal of noise or any other method for processing results.

The processed, accurate, or otherwise improved, resultant quantity is stored at step 1034 and the process 1000 may commence once again at step 1002.

Turning to FIG. 30 it is seen that at step 1050 the ambient environment temperature $T_{ai}$ may be measured at a first time (e.g. the initial time $t_i$), such as by ambient sensor 186. Thereafter, the initial temperature $T_{si}$ of the substance may be measured, such as by temperature sensor 184, as seen at step 1054. The time $t_i$ may be measured and stored at step 1058, as well as the measured ambient environment temperature $T_{ai}$ and the temperature $T_{si}$ of the substance. The time may be measured in any suitable manner, such as by timer 220.

At step 1060 it is verified whether the temperature of the substance shifted by the predetermined temperature change ΔT at time $t_f$. If the shift did not occur, the substance temperature may be measured, as seen in steps 1054 and 1058. If the shift was effected, the ambient environment temperature $T_a(t)$, may be measured at a second time (e.g. $t_f$ or any given time), in step 1064.

At step 1068 the measured ambient environment temperatures $T_{ai}$ and $T_a(t)$ may be compared and the process may proceed if it is verified that $T_{ai}$ is substantially as in $T_a(t)$, i.e. $T_a(t)=T_{ai}$. This is to ensure the ambient environment temperature is stable while measuring the substance temperature.

If $T_{ai}$ and $T_a(t)$ are dissimilar no calculation of the substance quantity is performed and the ECM 162 may be activated for returning the temperature of the substance to the original temperature, prior to the temperature change of ΔT. This may conclude the process 1001, as seen at step 1069.

If $T_{ai}$ is substantially as in $T_a(t)$ at step 1070 the substance quantity may be calculated based on the stored time span t, such as according to Formula 2 described above. At step 1074 the calculated substance quantity may be stored.

At step 1069 the ECM 162 may be activated for returning the temperature of the substance to the original temperature, prior to the temperature change of ΔT. This may conclude the process 1001.

In some embodiments, The ECM 162 may be activated only once the substance temperature shifts by the predetermined temperature variation ΔT.

The steps described in processes 1000 and 1001 may be interchangeable and some steps may be obviated.

It can be seen that by executing the algorithms of processes 1000 and 1001 the substance quantity calculation may be repeated several times to improve accuracy and record the amount of a substance which was previously used. Data can be recorded in a memory for later transfer by wired or wireless transmission to device 250 or to central database 252, such as described in reference to FIG. 2.

In addition to the substance quantity calculation system and method described in reference to FIGS. 26-30, the substance quantity calculation may be performed by other systems and methods, such as described as follows. In some embodiments, these systems and methods may be combined with the system and method described in reference to FIGS. 26-30.

In some embodiments, a substance quantity calculation system and method may comprise tracking the quantity of a dose of a delivered substance and then subtracting it from a known initial quantity of substance prior to delivery of the substance (e.g., when the chamber 106 is initially full).

In some embodiments, a substance quantity calculation system and method may include a measurement determined by at least one of sound (e.g., ultrasound), impedance, and photo-acoustic measurement. For example, wherein the container is an injection pen 108 (FIG. 1A) measuring the phase or time of flight of a wave in the chamber 106 can provide the distance from one side of the chamber 106 to the piston 118. Upon knowing the diameter of the chamber 106, the amount of substance therein can be determined based on the discovered distance and known diameter.

In some embodiments, a substance quantity calculation system and method may include detecting a length by phase measurement where a transponder is tuned over a frequency range to sending and receiving ultrasound waves to detect a maximum signal at a predetermined frequency. The wavelength corresponding to the maximum signal will relate to a distance between the transmitter and the receiver which is twice the length of the substance volume within the chamber 106. Thereby providing the length still occupied with the substance and enabling calculation of the remaining substance volume. Additionally, potential measurement of the impedance or other electrical properties of the substance, as well as the distance between the edges of the chamber 106.

In some embodiments, a substance quantity calculation system and method may include providing a charge-coupled device (CCD) for imaging the location of a plunger of the piston 118 prior to delivery of the substance and following delivery thereof. The delivered substance quantity can be calculated by the resultant distance moved by the plunger.

While the disclosure has been described with respect to a limited number of embodiments, it is to be realized that any combination of embodiments in whole or part can also be used and that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be an example and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure. Some embodiments may be distinguishable from the prior art for specifically lacking one or more features/elements/functionality (i.e., claims directed to such embodiments may include negative limitations).

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Any and all references to publications or other documents, including but not limited to, patents, patent applications, articles, webpages, books, etc., presented anywhere in the present application, are herein incorporated by reference in their entirety. Moreover, all definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is currently claimed:

1. A handheld, portable environmental control sleeve configured for receiving an end of a drug delivery device comprising:
    an environmental control element (ECE) comprising:
        an open end,
        an interior volume,
        thermal insulation material formed at least of a first exterior wall, and a second interior wall spaced away from the first exterior wall and defining an evacuated gap therebetween, wherein the second interior wall defines the interior volume of the ECE, and
        a phase change material arranged outside of the evacuated gap; and
    at least one of a power source, a processor, at least one electrical contact, at least one indicator, at least one switch, at least one temperature sensor, and a wireless transceiver,
    wherein:
        the interior volume of the ECE is configured to receive, via the open end, only a reservoir end of the drug delivery device, the reservoir end having a reservoir configured to contain a drug,
        the ECE further comprises mating means, arranged adjacent the open end and/or within the interior volume, and configured to mate with a corresponding feature of the reservoir end of the drug delivery device so as to removably retain only the reservoir end within the interior volume, and
        the ECE is configured to control the temperature of the drug contained within the reservoir end received within the interior volume within the at least one predetermined range.

2. The sleeve of claim 1, wherein the at least one predetermined range comprises at least two predetermined ranges.

3. The sleeve of claim 2, wherein:
    the at least two predetermined ranges comprise a first predetermined range and a second predetermined range, and
    the ECE is configured to switch from controlling the temperature of the drug contained within the reservoir to be within the first predetermined range to being within the second predetermined range.

4. The sleeve of claim 1, wherein the at least one temperature sensor is configured to sense a temperature inside the sleeve.

5. The sleeve of claim 1, wherein the ECE is configured to control the temperature of the drug contained within the reservoir at above and/or below the at least one predetermined range.

6. The sleeve of claim 1, wherein the ECE is configured to perform at least one of:
    cooling the drug contained within the reservoir when a temperature inside the sleeve is above the at least one predetermined range to a temperature within the at least one predetermined range, and
    heating the drug contained within the reservoir when a temperature inside the sleeve is below the at least one predetermined range to a temperature within the at least one predetermined range.

7. The sleeve of claim 1, wherein:
    the at least one predetermined range comprises a first predetermined ranges and a second predetermined range,
    the ECE is configured to control the temperature of the drug contained within the reservoir according to at least one of:
        a storage state configured to retain the drug contained within the reservoir within the first predetermined range, and
        a use state configured to retain the drug contained within the reservoir within the second predetermined range.

8. The sleeve of claim 1, wherein prior to a first use of the reservoir, the temperature of the drug contained within the reservoir is maintained at a storage state.

9. The sleeve of claim 1, wherein after a first use of the reservoir, the temperature of the drug contained within the reservoir is maintained at a use state.

10. The sleeve of claim 1, wherein the mating means comprises a recess configured to receive a protrusion on the reservoir end of the drug delivery device.

11. The sleeve of claim 1, wherein the mating means comprises a protrusion configured for receiving by a recess on the reservoir end of the drug delivery device.

12. The sleeve of claim 1, wherein the mating means comprises an interior volume shape of the interior volume configured to mechanically correspond and fit the reservoir end of the drug delivery device.

* * * * *